(12) United States Patent
Long

(10) Patent No.: US 9,375,268 B2
(45) Date of Patent: Jun. 28, 2016

(54) ELECTROPORATION ABLATION APPARATUS, SYSTEM, AND METHOD

(71) Applicant: Ethicon Endo-Surgery, Inc., Cincinnati, OH (US)

(72) Inventor: Gary L. Long, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 105 days.

(21) Appl. No.: 13/890,589

(22) Filed: May 9, 2013

(65) Prior Publication Data

US 2013/0261389 A1    Oct. 3, 2013

Related U.S. Application Data

(60) Continuation of application No. 12/694,452, filed on Jan. 27, 2010, now Pat. No. 8,449,538, which is a division of application No. 11/706,766, filed on Feb. 15, 2007, now Pat. No. 7,655,004.

(51) Int. Cl.
*A61B 18/14* (2006.01)
*A61N 1/32* (2006.01)
(Continued)

(52) U.S. Cl.
CPC ............ *A61B 18/1482* (2013.01); *A61B 1/018* (2013.01); *A61B 1/04* (2013.01); *A61B 1/06* (2013.01); *A61B 18/1492* (2013.01);
(Continued)

(58) Field of Classification Search
CPC ........... A61B 2018/00166; A61B 2018/00202; A61B 2018/1425; A61B 2018/1427; A61B 2018/143; A61B 18/1477

USPC ........................................................... 606/41
See application file for complete search history.

(56) References Cited

U.S. PATENT DOCUMENTS

| 645,576 A | 3/1900 | Telsa |
| 649,621 A | 5/1900 | Tesla |

(Continued)

FOREIGN PATENT DOCUMENTS

| AU | 666310 B2 | 2/1996 |
| DE | 3008120 A1 | 9/1980 |

(Continued)

OTHER PUBLICATIONS

Edd, et al., "In Vivo Results of a New Focal Tissue Ablation Technique: Irreversible Electroporation," IEEE Trans Biomed Eng, vol. 53, pp. 1409-1415, 2006.

(Continued)

*Primary Examiner* — Ronald Hupczey, Jr.

(57) ABSTRACT

A surgical instrument, such as an endoscopic or laparoscopic instrument, includes an ablation device. The ablation device includes an elongate relatively flexible member having a proximal end and a distal end, the flexible member includes at least a first working channel. A first and second electrode extends from a working channel at the distal end of the flexible member. The first and second electrodes are adapted to be endoscopically located in a tissue treatment region. The first and second electrodes are adapted to couple to an electrical waveform generator to receive an irreversible electroporation electrical waveform sufficient to ablate tissue located between the first and second electrodes. The waveform parameters of the irreversible electroporation electrical waveform are determined based on image information received from the tissue treatment region.

19 Claims, 12 Drawing Sheets

(51) Int. Cl.
    *A61B 1/018*     (2006.01)
    *A61B 1/04*     (2006.01)
    *A61B 1/06*     (2006.01)
    *A61N 1/30*     (2006.01)
    *A61B 18/00*     (2006.01)

(52) U.S. Cl.
    CPC ............... *A61N1/306* (2013.01); *A61N 1/327* (2013.01); *A61B 2018/00482* (2013.01); *A61B 2018/00577* (2013.01)

(56) References Cited

U.S. PATENT DOCUMENTS

| | | | |
|---|---|---|---|
| 787,412 | A | 4/1905 | Tesla |
| 1,039,354 | A | 9/1912 | Bonadio |
| 1,127,948 | A | 2/1915 | Wappler |
| 1,482,653 | A | 2/1924 | Lilly |
| 1,581,706 | A | 4/1926 | White |
| 1,581,707 | A | 4/1926 | White |
| 1,581,708 | A | 4/1926 | White |
| 1,581,709 | A | 4/1926 | White |
| 1,581,710 | A | 4/1926 | White |
| 1,625,602 | A | 4/1927 | Gould et al. |
| 1,916,722 | A | 7/1933 | Ende |
| 2,028,635 | A | 1/1936 | Wappler |
| 2,031,682 | A | 2/1936 | Wappler et al. |
| 2,113,246 | A | 4/1938 | Wappler |
| 2,137,710 | A | 11/1938 | Anderson |
| 2,155,365 | A | 4/1939 | Rankin |
| 2,191,858 | A | 2/1940 | Moore |
| 2,196,620 | A | 4/1940 | Attarian |
| 2,388,137 | A | 10/1945 | Graumlich |
| 2,451,077 | A | 10/1948 | Emsig |
| 2,493,108 | A | 1/1950 | Casey, Jr. |
| 2,504,152 | A | 4/1950 | Riker et al. |
| 2,938,382 | A | 5/1960 | De Graaf |
| 2,952,206 | A | 9/1960 | Becksted |
| 3,044,461 | A | 7/1962 | Murdock |
| 3,069,195 | A | 12/1962 | Buck |
| 3,070,088 | A | 12/1962 | Brahos |
| 3,170,471 | A | 2/1965 | Schnitzer |
| 3,435,824 | A | 4/1969 | Gamponia |
| 3,470,876 | A | 10/1969 | Barchilon |
| 3,481,325 | A | 12/1969 | Glassman |
| 3,595,239 | A | 7/1971 | Petersen |
| 3,669,487 | A | 6/1972 | Roberts et al. |
| 3,746,881 | A | 7/1973 | Fitch et al. |
| 3,799,672 | A | 3/1974 | Vurek |
| 3,854,473 | A | 12/1974 | Matsuo |
| 3,946,740 | A | 3/1976 | Bassett |
| 3,948,251 | A | 4/1976 | Hosono |
| 3,961,632 | A | 6/1976 | Moossun |
| 3,965,890 | A | 6/1976 | Gauthier |
| 3,994,301 | A | 11/1976 | Agris |
| 4,011,872 | A | 3/1977 | Komiya |
| 4,012,812 | A | 3/1977 | Black |
| 4,085,743 | A | 4/1978 | Yoon |
| 4,164,225 | A | 8/1979 | Johnson et al. |
| 4,170,997 | A | 10/1979 | Pinnow et al. |
| 4,174,715 | A | 11/1979 | Hasson |
| 4,178,920 | A | 12/1979 | Cawood, Jr. et al. |
| 4,207,873 | A | 6/1980 | Kruy |
| 4,235,238 | A | 11/1980 | Ogiu et al. |
| 4,258,716 | A | 3/1981 | Sutherland |
| 4,269,174 | A | 5/1981 | Adair |
| 4,278,077 | A | 7/1981 | Mizumoto |
| 4,281,646 | A | 8/1981 | Kinoshita |
| 4,285,344 | A | 8/1981 | Marshall |
| 4,311,143 | A | 1/1982 | Komiya |
| 4,329,980 | A | 5/1982 | Terada |
| 4,393,872 | A | 7/1983 | Reznik et al. |
| 4,396,021 | A | 8/1983 | Baumgartner |
| 4,406,656 | A | 9/1983 | Hattler et al. |
| 4,452,246 | A | 6/1984 | Bader et al. |
| 4,461,281 | A | 7/1984 | Carson |
| 4,491,132 | A | 1/1985 | Aikins |
| 4,492,232 | A | 1/1985 | Green |
| 4,527,331 | A | 7/1985 | Lasner et al. |
| 4,527,564 | A | 7/1985 | Eguchi et al. |
| 4,538,594 | A | 9/1985 | Boebel et al. |
| D281,104 | S | 10/1985 | Davison |
| 4,569,347 | A | 2/1986 | Frisbie |
| 4,580,551 | A | 4/1986 | Siegmund et al. |
| 4,646,722 | A | 3/1987 | Silverstein et al. |
| 4,653,476 | A | 3/1987 | Bonnet |
| 4,655,219 | A | 4/1987 | Petruzzi |
| 4,657,016 | A | 4/1987 | Garito et al. |
| 4,657,018 | A | 4/1987 | Hakky |
| 4,669,470 | A | 6/1987 | Brandfield |
| 4,671,477 | A | 6/1987 | Cullen |
| 4,677,982 | A | 7/1987 | Llinas et al. |
| 4,685,447 | A | 8/1987 | Iversen et al. |
| 4,711,240 | A | 12/1987 | Goldwasser et al. |
| 4,712,545 | A | 12/1987 | Honkanen |
| 4,721,116 | A | 1/1988 | Schintgen et al. |
| 4,727,600 | A | 2/1988 | Avakian |
| 4,733,662 | A | 3/1988 | DeSatnick et al. |
| D295,894 | S | 5/1988 | Sharkany et al. |
| 4,742,817 | A | 5/1988 | Kawashima et al. |
| 4,753,223 | A | 6/1988 | Bremer |
| 4,763,669 | A | 8/1988 | Jaeger |
| 4,770,188 | A | 9/1988 | Chikama |
| 4,790,624 | A | 12/1988 | Van Hoye et al. |
| 4,791,707 | A | 12/1988 | Tucker |
| 4,796,627 | A | 1/1989 | Tucker |
| 4,807,593 | A | 2/1989 | Ito |
| 4,815,450 | A | 3/1989 | Patel |
| 4,819,620 | A | 4/1989 | Okutsu |
| 4,823,794 | A | 4/1989 | Pierce |
| 4,829,999 | A | 5/1989 | Auth |
| 4,836,188 | A | 6/1989 | Berry |
| 4,846,573 | A | 7/1989 | Taylor et al. |
| 4,867,140 | A | 9/1989 | Hovis et al. |
| 4,869,238 | A | 9/1989 | Opie et al. |
| 4,869,459 | A | 9/1989 | Bourne |
| 4,873,979 | A | 10/1989 | Hanna |
| 4,880,015 | A | 11/1989 | Nierman |
| 4,904,048 | A | 2/1990 | Sogawa et al. |
| 4,911,148 | A | 3/1990 | Sosnowski et al. |
| 4,926,860 | A | 5/1990 | Stice et al. |
| 4,934,364 | A | 6/1990 | Green |
| 4,938,214 | A | 7/1990 | Specht et al. |
| 4,950,273 | A | 8/1990 | Briggs |
| 4,950,285 | A | 8/1990 | Wilk |
| 4,953,539 | A | 9/1990 | Nakamura et al. |
| 4,960,133 | A | 10/1990 | Hewson |
| 4,977,887 | A | 12/1990 | Gouda |
| 4,979,496 | A | 12/1990 | Komi |
| 4,979,950 | A | 12/1990 | Transue et al. |
| 4,984,581 | A | 1/1991 | Stice |
| 4,990,152 | A | 2/1991 | Yoon |
| 4,991,565 | A | 2/1991 | Takahashi et al. |
| 4,994,079 | A | 2/1991 | Genese et al. |
| 5,007,917 | A | 4/1991 | Evans |
| 5,010,876 | A | 4/1991 | Henley et al. |
| 5,020,514 | A | 6/1991 | Heckele |
| 5,020,535 | A | 6/1991 | Parker et al. |
| 5,025,778 | A | 6/1991 | Silverstein et al. |
| 5,026,379 | A | 6/1991 | Yoon |
| 5,033,169 | A | 7/1991 | Bindon |
| 5,037,433 | A | 8/1991 | Wilk et al. |
| 5,041,129 | A | 8/1991 | Hayhurst et al. |
| 5,046,513 | A | 9/1991 | Gatturna et al. |
| 5,050,585 | A | 9/1991 | Takahashi |
| 5,052,372 | A | 10/1991 | Shapiro |
| 5,065,516 | A | 11/1991 | Dulebohn |
| 5,066,295 | A | 11/1991 | Kozak et al. |
| 5,098,378 | A | 3/1992 | Piontek et al. |
| 5,108,421 | A | 4/1992 | Fowler |
| 5,123,913 | A | 6/1992 | Wilk et al. |
| 5,123,914 | A | 6/1992 | Cope |
| 5,133,727 | A | 7/1992 | Bales et al. |
| 5,147,374 | A | 9/1992 | Fernandez |
| 5,174,300 | A | 12/1992 | Bales et al. |

(56) References Cited

U.S. PATENT DOCUMENTS

| | | |
|---|---|---|
| 5,176,126 A | 1/1993 | Chikama |
| 5,190,050 A | 3/1993 | Nitzsche |
| 5,190,555 A | 3/1993 | Wetter et al. |
| 5,192,284 A | 3/1993 | Pleatman |
| 5,192,300 A | 3/1993 | Fowler |
| 5,197,963 A | 3/1993 | Parins |
| 5,201,752 A | 4/1993 | Brown et al. |
| 5,201,908 A | 4/1993 | Jones |
| 5,203,785 A | 4/1993 | Slater |
| 5,203,787 A | 4/1993 | Noblitt et al. |
| 5,209,747 A | 5/1993 | Knoepfler |
| 5,217,003 A | 6/1993 | Wilk |
| 5,217,453 A | 6/1993 | Wilk |
| 5,219,357 A | 6/1993 | Honkanen et al. |
| 5,219,358 A | 6/1993 | Bendel et al. |
| 5,222,362 A | 6/1993 | Maus et al. |
| 5,222,965 A | 6/1993 | Haughton |
| 5,234,437 A | 8/1993 | Sepetka |
| 5,234,453 A | 8/1993 | Smith et al. |
| 5,235,964 A | 8/1993 | Abenaim |
| 5,242,456 A | 9/1993 | Nash et al. |
| 5,245,460 A | 9/1993 | Allen et al. |
| 5,246,424 A | 9/1993 | Wilk |
| 5,257,999 A | 11/1993 | Slanetz, Jr. |
| 5,259,366 A | 11/1993 | Reydel et al. |
| 5,263,958 A | 11/1993 | deGuillebon et al. |
| 5,273,524 A | 12/1993 | Fox et al. |
| 5,275,607 A | 1/1994 | Lo et al. |
| 5,275,614 A | 1/1994 | Haber et al. |
| 5,275,616 A | 1/1994 | Fowler |
| 5,284,128 A | 2/1994 | Hart |
| 5,284,162 A | 2/1994 | Wilk |
| 5,287,845 A | 2/1994 | Faul et al. |
| 5,287,852 A | 2/1994 | Arkinstall |
| 5,290,299 A | 3/1994 | Fain et al. |
| 5,290,302 A | 3/1994 | Pericic |
| 5,295,977 A | 3/1994 | Cohen et al. |
| 5,297,536 A | 3/1994 | Wilk |
| 5,297,687 A | 3/1994 | Freed |
| 5,301,061 A | 4/1994 | Nakada et al. |
| 5,312,023 A | 5/1994 | Green et al. |
| 5,312,333 A | 5/1994 | Churinetz et al. |
| 5,312,351 A | 5/1994 | Gerrone |
| 5,312,416 A | 5/1994 | Spaeth et al. |
| 5,312,423 A | 5/1994 | Rosenbluth et al. |
| 5,318,589 A | 6/1994 | Lichtman |
| 5,320,636 A | 6/1994 | Slater |
| 5,324,261 A | 6/1994 | Amundson et al. |
| 5,325,845 A | 7/1994 | Adair |
| 5,330,471 A | 7/1994 | Eggers |
| 5,330,486 A | 7/1994 | Wilk |
| 5,330,488 A | 7/1994 | Goldrath |
| 5,330,496 A | 7/1994 | Alferness |
| 5,330,502 A | 7/1994 | Hassler et al. |
| 5,331,971 A | 7/1994 | Bales et al. |
| 5,334,168 A | 8/1994 | Hemmer |
| 5,334,198 A | 8/1994 | Hart et al. |
| 5,336,192 A | 8/1994 | Palestrant |
| 5,336,222 A | 8/1994 | Durgin, Jr. et al. |
| 5,339,805 A | 8/1994 | Parker |
| 5,341,815 A | 8/1994 | Cofone et al. |
| 5,342,396 A | 8/1994 | Cook |
| 5,344,428 A | 9/1994 | Griffiths |
| 5,345,927 A | 9/1994 | Bonutti |
| 5,348,259 A | 9/1994 | Blanco et al. |
| 5,350,391 A | 9/1994 | Iacovelli |
| 5,352,184 A | 10/1994 | Goldberg et al. |
| 5,352,222 A | 10/1994 | Rydell |
| 5,354,302 A | 10/1994 | Ko |
| 5,354,311 A | 10/1994 | Kambin et al. |
| 5,356,381 A | 10/1994 | Ensminger et al. |
| 5,356,408 A | 10/1994 | Rydell |
| 5,360,428 A | 11/1994 | Hutchinson, Jr. |
| 5,364,408 A | 11/1994 | Gordon |
| 5,364,410 A | 11/1994 | Failla et al. |
| 5,366,466 A | 11/1994 | Christian et al. |
| 5,366,467 A | 11/1994 | Lynch et al. |
| 5,368,605 A | 11/1994 | Miller, Jr. |
| 5,370,647 A | 12/1994 | Graber et al. |
| 5,370,679 A | 12/1994 | Atlee, III |
| 5,374,273 A | 12/1994 | Nakao et al. |
| 5,374,275 A | 12/1994 | Bradley et al. |
| 5,374,277 A | 12/1994 | Hassler |
| 5,374,953 A | 12/1994 | Sasaki et al. |
| 5,376,077 A | 12/1994 | Gomringer |
| 5,377,695 A | 1/1995 | An Haack |
| 5,383,877 A | 1/1995 | Clarke |
| 5,383,888 A | 1/1995 | Zvenyatsky et al. |
| 5,386,817 A | 2/1995 | Jones |
| 5,387,259 A | 2/1995 | Davidson |
| 5,391,174 A | 2/1995 | Weston |
| 5,392,789 A | 2/1995 | Slater et al. |
| 5,395,386 A | 3/1995 | Slater |
| 5,397,332 A | 3/1995 | Kammerer et al. |
| 5,401,248 A | 3/1995 | Bencini |
| 5,403,311 A | 4/1995 | Abele et al. |
| 5,403,328 A | 4/1995 | Shallman |
| 5,403,342 A | 4/1995 | Tovey et al. |
| 5,403,348 A | 4/1995 | Bonutti |
| 5,405,073 A | 4/1995 | Porter |
| 5,405,359 A | 4/1995 | Pierce |
| 5,409,478 A | 4/1995 | Gerry et al. |
| 5,417,699 A | 5/1995 | Klein et al. |
| 5,423,821 A | 6/1995 | Pasque |
| 5,431,635 A | 7/1995 | Yoon |
| 5,433,721 A | 7/1995 | Hooven et al. |
| 5,433,735 A | 7/1995 | Zanakis et al. |
| 5,439,471 A | 8/1995 | Kerr |
| 5,439,478 A | 8/1995 | Palmer |
| 5,441,059 A | 8/1995 | Dannan |
| 5,441,494 A | 8/1995 | Ortiz |
| 5,441,498 A | 8/1995 | Perkins |
| 5,441,499 A | 8/1995 | Fritzsch |
| 5,443,463 A | 8/1995 | Stern et al. |
| 5,445,638 A | 8/1995 | Rydell et al. |
| 5,445,648 A | 8/1995 | Cook |
| 5,449,021 A | 9/1995 | Chikama |
| 5,454,827 A | 10/1995 | Aust et al. |
| 5,456,667 A | 10/1995 | Ham et al. |
| 5,456,684 A | 10/1995 | Schmidt et al. |
| 5,458,131 A | 10/1995 | Wilk |
| 5,458,583 A | 10/1995 | McNeely et al. |
| 5,460,168 A | 10/1995 | Masubuchi et al. |
| 5,460,629 A | 10/1995 | Shlain et al. |
| 5,462,561 A | 10/1995 | Voda |
| 5,465,731 A | 11/1995 | Bell et al. |
| 5,467,763 A | 11/1995 | McMahon et al. |
| 5,468,250 A | 11/1995 | Paraschac et al. |
| 5,470,308 A | 11/1995 | Edwards et al. |
| 5,470,320 A | 11/1995 | Tiefenbrun et al. |
| 5,472,441 A | 12/1995 | Edwards et al. |
| 5,478,347 A | 12/1995 | Aranyi |
| 5,478,352 A | 12/1995 | Fowler |
| 5,480,404 A | 1/1996 | Kammerer et al. |
| 5,482,029 A | 1/1996 | Sekiguchi et al. |
| 5,482,054 A | 1/1996 | Slater et al. |
| 5,484,451 A | 1/1996 | Akopov et al. |
| 5,489,256 A | 2/1996 | Adair |
| 5,496,347 A | 3/1996 | Hashiguchi et al. |
| 5,499,990 A | 3/1996 | Schülken et al. |
| 5,499,992 A | 3/1996 | Meade et al. |
| 5,499,997 A | 3/1996 | Sharpe et al. |
| 5,500,012 A | 3/1996 | Brucker et al. |
| 5,501,692 A | 3/1996 | Riza |
| 5,503,616 A | 4/1996 | Jones |
| 5,505,686 A | 4/1996 | Willis et al. |
| 5,507,755 A | 4/1996 | Gresl et al. |
| 5,511,564 A | 4/1996 | Wilk |
| 5,514,157 A | 5/1996 | Nicholas et al. |
| 5,518,501 A | 5/1996 | Oneda et al. |
| 5,522,829 A | 6/1996 | Michalos |
| 5,522,830 A | 6/1996 | Aranyi |
| 5,527,321 A | 6/1996 | Hinchliffe |
| 5,533,418 A | 7/1996 | Wu et al. |

(56) References Cited

U.S. PATENT DOCUMENTS

| | | |
|---|---|---|
| 5,536,248 A | 7/1996 | Weaver et al. |
| 5,538,509 A | 7/1996 | Dunlap et al. |
| 5,540,648 A | 7/1996 | Yoon |
| 5,549,637 A | 8/1996 | Crainich |
| 5,554,151 A | 9/1996 | Hinchliffe |
| 5,555,883 A | 9/1996 | Avitall |
| 5,558,133 A | 9/1996 | Bortoli et al. |
| 5,562,693 A | 10/1996 | Devlin et al. |
| 5,569,243 A | 10/1996 | Kortenbach et al. |
| 5,569,298 A | 10/1996 | Schnell |
| 5,571,090 A | 11/1996 | Sherts |
| 5,573,540 A | 11/1996 | Yoon |
| 5,578,030 A | 11/1996 | Levin |
| 5,582,611 A | 12/1996 | Tsuruta et al. |
| 5,582,617 A | 12/1996 | Klieman et al. |
| 5,584,845 A | 12/1996 | Hart |
| 5,590,660 A | 1/1997 | MacAulay et al. |
| 5,591,179 A | 1/1997 | Edelstein |
| 5,591,205 A | 1/1997 | Fowler |
| 5,593,420 A | 1/1997 | Eubanks, Jr. et al. |
| 5,595,562 A | 1/1997 | Grier |
| 5,597,378 A | 1/1997 | Jervis |
| 5,601,573 A | 2/1997 | Fogelberg et al. |
| 5,601,574 A | 2/1997 | Stefanchik et al. |
| 5,601,588 A | 2/1997 | Tonomura et al. |
| 5,601,602 A | 2/1997 | Fowler |
| 5,604,531 A | 2/1997 | Iddan et al. |
| 5,607,386 A | 3/1997 | Flam |
| 5,607,389 A | 3/1997 | Edwards et al. |
| 5,607,406 A | 3/1997 | Hernandez et al. |
| 5,607,450 A | 3/1997 | Zvenyatsky et al. |
| 5,609,601 A | 3/1997 | Kolesa et al. |
| 5,613,975 A | 3/1997 | Christy |
| 5,613,977 A | 3/1997 | Weber et al. |
| 5,614,943 A | 3/1997 | Nakamura et al. |
| 5,616,117 A | 4/1997 | Dinkler et al. |
| 5,618,303 A | 4/1997 | Marlow et al. |
| 5,620,415 A | 4/1997 | Lucey et al. |
| 5,624,399 A | 4/1997 | Ackerman |
| 5,624,431 A | 4/1997 | Gerry et al. |
| 5,626,578 A | 5/1997 | Tihon |
| 5,626,587 A | 5/1997 | Bishop et al. |
| 5,628,732 A | 5/1997 | Antoon, Jr. et al. |
| 5,630,782 A | 5/1997 | Adair |
| 5,630,795 A | 5/1997 | Kuramoto et al. |
| 5,643,283 A | 7/1997 | Younker |
| 5,643,292 A | 7/1997 | Hart |
| 5,643,294 A | 7/1997 | Tovey et al. |
| 5,644,798 A | 7/1997 | Shah |
| 5,645,083 A | 7/1997 | Essig et al. |
| 5,645,519 A | 7/1997 | Lee et al. |
| 5,645,565 A | 7/1997 | Rudd et al. |
| 5,649,372 A | 7/1997 | Souza |
| 5,653,677 A | 8/1997 | Okada et al. |
| 5,653,690 A | 8/1997 | Booth et al. |
| 5,653,722 A | 8/1997 | Kieturakis |
| 5,657,755 A | 8/1997 | Desai |
| 5,662,621 A | 9/1997 | Lafontaine |
| 5,662,663 A | 9/1997 | Shallman |
| 5,667,527 A | 9/1997 | Cook |
| 5,669,875 A | 9/1997 | van Eerdenburg |
| 5,681,276 A | 10/1997 | Lundquist |
| 5,681,279 A | 10/1997 | Roper et al. |
| 5,681,324 A | 10/1997 | Kammerer et al. |
| 5,681,330 A | 10/1997 | Hughett et al. |
| 5,685,820 A | 11/1997 | Riek et al. |
| 5,690,606 A | 11/1997 | Slotman |
| 5,690,656 A | 11/1997 | Cope et al. |
| 5,690,660 A | 11/1997 | Kauker et al. |
| 5,695,448 A | 12/1997 | Kimura et al. |
| 5,695,505 A | 12/1997 | Yoon |
| 5,695,511 A | 12/1997 | Cano et al. |
| 5,700,275 A | 12/1997 | Bell et al. |
| 5,702,438 A | 12/1997 | Avitall |
| 5,704,892 A | 1/1998 | Adair |
| 5,709,708 A | 1/1998 | Thal |
| 5,711,921 A | 1/1998 | Langford |
| 5,716,326 A | 2/1998 | Dannan |
| 5,716,375 A | 2/1998 | Fowler |
| 5,725,542 A | 3/1998 | Yoon |
| 5,728,094 A | 3/1998 | Edwards |
| 5,730,740 A | 3/1998 | Wales et al. |
| 5,735,849 A | 4/1998 | Baden et al. |
| 5,741,234 A | 4/1998 | Aboul-Hosn |
| 5,741,278 A | 4/1998 | Stevens |
| 5,741,285 A | 4/1998 | McBrayer et al. |
| 5,741,429 A | 4/1998 | Donadio, III et al. |
| 5,743,456 A | 4/1998 | Jones et al. |
| 5,746,759 A | 5/1998 | Meade et al. |
| 5,749,826 A | 5/1998 | Faulkner |
| 5,749,881 A | 5/1998 | Sackier et al. |
| 5,749,889 A | 5/1998 | Bacich et al. |
| 5,752,951 A | 5/1998 | Yanik |
| 5,755,731 A | 5/1998 | Grinberg |
| 5,759,150 A | 6/1998 | Konou et al. |
| 5,759,151 A | 6/1998 | Sturges |
| 5,762,604 A | 6/1998 | Kieturakis |
| 5,766,167 A | 6/1998 | Eggers et al. |
| 5,766,170 A | 6/1998 | Eggers |
| 5,766,205 A | 6/1998 | Zvenyatsky et al. |
| 5,769,849 A | 6/1998 | Eggers |
| 5,776,188 A | 7/1998 | Shepherd et al. |
| 5,779,701 A | 7/1998 | McBrayer et al. |
| 5,779,716 A | 7/1998 | Cano et al. |
| 5,779,720 A | 7/1998 | Walder-Utz et al. |
| 5,779,727 A | 7/1998 | Orejola |
| 5,782,859 A | 7/1998 | Nicholas et al. |
| 5,782,861 A | 7/1998 | Cragg et al. |
| 5,782,866 A | 7/1998 | Wenstrom, Jr. |
| 5,791,022 A | 8/1998 | Bohman |
| 5,792,113 A | 8/1998 | Kramer et al. |
| 5,792,153 A | 8/1998 | Swain et al. |
| 5,792,165 A | 8/1998 | Klieman et al. |
| 5,797,835 A | 8/1998 | Green |
| 5,797,928 A | 8/1998 | Kogasaka |
| 5,797,939 A | 8/1998 | Yoon |
| 5,797,941 A | 8/1998 | Schulze et al. |
| 5,797,959 A | 8/1998 | Castro et al. |
| 5,797,960 A | 8/1998 | Stevens et al. |
| 5,800,449 A | 9/1998 | Wales |
| 5,800,451 A | 9/1998 | Buess et al. |
| 5,803,903 A | 9/1998 | Athas et al. |
| 5,807,395 A | 9/1998 | Mulier et al. |
| 5,808,665 A | 9/1998 | Green |
| 5,810,805 A * | 9/1998 | Sutcu ............... A61B 18/1442 606/45 |
| 5,810,806 A | 9/1998 | Ritchart et al. |
| 5,810,849 A | 9/1998 | Kontos |
| 5,810,865 A | 9/1998 | Koscher et al. |
| 5,810,876 A | 9/1998 | Kelleher |
| 5,810,877 A | 9/1998 | Roth et al. |
| 5,813,976 A | 9/1998 | Filipi et al. |
| 5,814,026 A | 9/1998 | Yoon |
| 5,814,058 A | 9/1998 | Carlson et al. |
| 5,817,061 A | 10/1998 | Goodwin et al. |
| 5,817,107 A | 10/1998 | Schaller |
| 5,817,119 A | 10/1998 | Klieman et al. |
| 5,818,527 A | 10/1998 | Yamaguchi et al. |
| 5,819,736 A | 10/1998 | Avny et al. |
| 5,823,947 A | 10/1998 | Yoon et al. |
| 5,824,071 A | 10/1998 | Nelson et al. |
| 5,827,190 A | 10/1998 | Palcic et al. |
| 5,827,276 A | 10/1998 | LeVeen et al. |
| 5,827,281 A | 10/1998 | Levin |
| 5,827,299 A | 10/1998 | Thomason et al. |
| 5,827,323 A | 10/1998 | Klieman et al. |
| 5,830,221 A | 11/1998 | Stein et al. |
| 5,830,231 A | 11/1998 | Geiges, Jr. |
| 5,833,603 A | 11/1998 | Kovacs et al. |
| 5,833,700 A | 11/1998 | Fogelberg et al. |
| 5,833,703 A | 11/1998 | Manushakian |
| 5,833,715 A | 11/1998 | Vachon et al. |
| 5,836,960 A | 11/1998 | Kolesa et al. |
| 5,843,017 A | 12/1998 | Yoon |

(56) References Cited

U.S. PATENT DOCUMENTS

| | | | |
|---|---|---|---|
| 5,843,121 A | 12/1998 | Yoon |
| 5,849,022 A | 12/1998 | Sakashita et al. |
| 5,853,374 A | 12/1998 | Hart et al. |
| 5,855,569 A | 1/1999 | Komi |
| 5,855,585 A | 1/1999 | Kontos |
| 5,860,913 A | 1/1999 | Yamaya et al. |
| 5,860,995 A | 1/1999 | Berkelaar |
| 5,868,762 A | 2/1999 | Cragg et al. |
| 5,873,849 A | 2/1999 | Bernard |
| 5,876,411 A | 3/1999 | Kontos |
| 5,882,331 A | 3/1999 | Sasaki |
| 5,882,344 A | 3/1999 | Stouder, Jr. |
| 5,893,846 A | 4/1999 | Bales et al. |
| 5,893,874 A | 4/1999 | Bourque et al. |
| 5,893,875 A | 4/1999 | O'Connor et al. |
| 5,897,487 A | 4/1999 | Ouchi |
| 5,899,919 A | 5/1999 | Eubanks, Jr. et al. |
| 5,902,238 A | 5/1999 | Golden et al. |
| 5,902,254 A | 5/1999 | Magram |
| 5,904,702 A | 5/1999 | Ek et al. |
| 5,906,625 A | 5/1999 | Bito et al. |
| 5,908,420 A | 6/1999 | Parins et al. |
| 5,908,429 A | 6/1999 | Yoon |
| 5,911,737 A | 6/1999 | Lee et al. |
| 5,916,146 A | 6/1999 | Allotta et al. |
| 5,916,147 A | 6/1999 | Boury |
| 5,921,892 A | 7/1999 | Easton |
| 5,921,993 A | 7/1999 | Yoon |
| 5,921,997 A | 7/1999 | Fogelberg et al. |
| 5,922,008 A | 7/1999 | Gimpelson |
| 5,925,052 A | 7/1999 | Simmons |
| 5,928,255 A | 7/1999 | Meade et al. |
| 5,928,266 A | 7/1999 | Kontos |
| 5,936,536 A | 8/1999 | Morris |
| 5,938,661 A | 8/1999 | Hahnen |
| 5,941,815 A | 8/1999 | Chang |
| 5,944,718 A | 8/1999 | Austin et al. |
| 5,951,547 A | 9/1999 | Gough et al. |
| 5,951,549 A | 9/1999 | Richardson et al. |
| 5,954,720 A | 9/1999 | Wilson et al. |
| 5,954,731 A * | 9/1999 | Yoon .............................. 606/144 |
| 5,957,936 A | 9/1999 | Yoon et al. |
| 5,957,943 A | 9/1999 | Vaitekunas |
| 5,957,953 A | 9/1999 | DiPoto et al. |
| 5,964,782 A | 10/1999 | Lafontaine et al. |
| 5,970,581 A | 10/1999 | Chadwick et al. |
| 5,971,995 A | 10/1999 | Rousseau |
| 5,972,002 A | 10/1999 | Bark et al. |
| 5,976,074 A | 11/1999 | Moriyama |
| 5,976,075 A | 11/1999 | Beane et al. |
| 5,976,130 A | 11/1999 | McBrayer et al. |
| 5,976,131 A | 11/1999 | Guglielmi et al. |
| 5,980,539 A | 11/1999 | Kontos |
| 5,980,556 A | 11/1999 | Giordano et al. |
| 5,984,938 A | 11/1999 | Yoon |
| 5,984,939 A | 11/1999 | Yoon |
| 5,984,950 A | 11/1999 | Cragg et al. |
| 5,989,182 A | 11/1999 | Hori et al. |
| 5,993,447 A * | 11/1999 | Blewett .............. A61B 18/1477 600/105 |
| 5,993,474 A | 11/1999 | Ouchi |
| 5,995,875 A | 11/1999 | Blewett et al. |
| 5,997,555 A | 12/1999 | Kontos |
| 6,001,120 A | 12/1999 | Levin |
| 6,004,269 A | 12/1999 | Crowley et al. |
| 6,004,330 A | 12/1999 | Middleman et al. |
| 6,007,566 A | 12/1999 | Wenstrom, Jr. |
| 6,010,515 A | 1/2000 | Swain et al. |
| 6,012,494 A | 1/2000 | Balazs |
| 6,016,452 A | 1/2000 | Kasevich |
| 6,017,356 A | 1/2000 | Frederick et al. |
| 6,019,770 A | 2/2000 | Christoudias |
| 6,024,708 A | 2/2000 | Bales et al. |
| 6,024,747 A | 2/2000 | Kontos |
| 6,027,522 A | 2/2000 | Palmer |
| 6,030,365 A | 2/2000 | Laufer |
| 6,030,384 A | 2/2000 | Nezhat |
| 6,030,634 A | 2/2000 | Wu et al. |
| 6,033,399 A | 3/2000 | Gines |
| 6,033,401 A | 3/2000 | Edwards et al. |
| 6,036,640 A | 3/2000 | Corace et al. |
| 6,036,685 A | 3/2000 | Mueller |
| 6,050,992 A | 4/2000 | Nichols |
| 6,053,927 A | 4/2000 | Hamas |
| 6,053,937 A | 4/2000 | Edwards et al. |
| 6,059,719 A | 5/2000 | Yamamoto et al. |
| 6,066,160 A | 5/2000 | Colvin et al. |
| 6,068,603 A | 5/2000 | Suzuki |
| 6,068,629 A | 5/2000 | Haissaguerre et al. |
| 6,071,233 A | 6/2000 | Ishikawa et al. |
| 6,074,408 A | 6/2000 | Freeman |
| 6,086,530 A | 7/2000 | Mack |
| 6,090,105 A | 7/2000 | Zepeda et al. |
| 6,090,108 A | 7/2000 | McBrayer et al. |
| 6,090,129 A | 7/2000 | Ouchi |
| 6,096,046 A | 8/2000 | Weiss |
| 6,102,909 A | 8/2000 | Chen et al. |
| 6,102,926 A | 8/2000 | Tartaglia et al. |
| 6,106,473 A | 8/2000 | Violante et al. |
| 6,106,521 A * | 8/2000 | Blewett et al. .................. 606/41 |
| 6,109,852 A | 8/2000 | Shahinpoor et al. |
| 6,110,154 A | 8/2000 | Shimomura et al. |
| 6,110,183 A | 8/2000 | Cope |
| 6,113,593 A | 9/2000 | Tu et al. |
| 6,117,144 A | 9/2000 | Nobles et al. |
| 6,117,158 A | 9/2000 | Measamer et al. |
| 6,123,718 A | 9/2000 | Tu et al. |
| 6,131,790 A | 10/2000 | Piraka |
| 6,139,555 A | 10/2000 | Hart et al. |
| 6,141,037 A | 10/2000 | Upton et al. |
| 6,146,391 A | 11/2000 | Cigaina |
| 6,148,222 A | 11/2000 | Ramsey, III |
| 6,149,653 A | 11/2000 | Deslauriers |
| 6,149,662 A | 11/2000 | Pugliesi et al. |
| 6,152,871 A | 11/2000 | Foley et al. |
| 6,152,920 A | 11/2000 | Thompson et al. |
| 6,156,006 A | 12/2000 | Brosens et al. |
| 6,159,200 A | 12/2000 | Verdura et al. |
| 6,165,175 A | 12/2000 | Wampler et al. |
| 6,165,184 A | 12/2000 | Verdura et al. |
| 6,168,570 B1 | 1/2001 | Ferrera |
| 6,168,605 B1 | 1/2001 | Measamer et al. |
| 6,169,269 B1 | 1/2001 | Maynard |
| 6,170,130 B1 | 1/2001 | Hamilton et al. |
| 6,173,872 B1 | 1/2001 | Cohen |
| 6,179,776 B1 | 1/2001 | Adams et al. |
| 6,179,832 B1 | 1/2001 | Jones et al. |
| 6,179,837 B1 | 1/2001 | Hooven |
| 6,183,420 B1 | 2/2001 | Douk et al. |
| 6,190,353 B1 | 2/2001 | Makower et al. |
| 6,190,383 B1 | 2/2001 | Schmaltz et al. |
| 6,190,384 B1 | 2/2001 | Ouchi |
| 6,190,399 B1 | 2/2001 | Palmer et al. |
| 6,203,533 B1 | 3/2001 | Ouchi |
| 6,206,872 B1 | 3/2001 | Lafond et al. |
| 6,206,877 B1 | 3/2001 | Kese et al. |
| 6,206,904 B1 | 3/2001 | Ouchi |
| 6,210,409 B1 | 4/2001 | Ellman et al. |
| 6,214,007 B1 | 4/2001 | Anderson |
| 6,214,028 B1 | 4/2001 | Yoon et al. |
| 6,216,043 B1 | 4/2001 | Swanson et al. |
| 6,228,096 B1 | 5/2001 | Marchand |
| 6,231,506 B1 | 5/2001 | Hu et al. |
| 6,234,958 B1 | 5/2001 | Snoke et al. |
| 6,240,312 B1 | 5/2001 | Alfano et al. |
| 6,245,079 B1 | 6/2001 | Nobles et al. |
| 6,246,914 B1 | 6/2001 | de la Rama et al. |
| 6,258,064 B1 | 7/2001 | Smith et al. |
| 6,261,242 B1 | 7/2001 | Roberts et al. |
| 6,264,664 B1 | 7/2001 | Avellanet |
| 6,270,497 B1 | 8/2001 | Sekino et al. |
| 6,270,505 B1 | 8/2001 | Yoshida et al. |
| 6,277,136 B1 | 8/2001 | Bonutti |
| 6,283,963 B1 | 9/2001 | Regula |

(56) References Cited

U.S. PATENT DOCUMENTS

| | | |
|---|---|---|
| 6,287,304 B1 | 9/2001 | Eggers et al. |
| 6,293,909 B1 | 9/2001 | Chu et al. |
| 6,293,952 B1 | 9/2001 | Brosens et al. |
| 6,296,630 B1 | 10/2001 | Altman et al. |
| 6,314,963 B1 | 11/2001 | Vaska et al. |
| 6,322,578 B1 | 11/2001 | Houle et al. |
| 6,325,534 B1 | 12/2001 | Hawley et al. |
| 6,326,177 B1 | 12/2001 | Schoenbach et al. |
| 6,328,730 B1 | 12/2001 | Harkrider, Jr. |
| 6,350,267 B1 | 2/2002 | Stefanchik |
| 6,350,278 B1 | 2/2002 | Lenker et al. |
| 6,352,503 B1 | 3/2002 | Matsui et al. |
| 6,352,541 B1 | 3/2002 | Kienzle et al. |
| 6,352,543 B1 | 3/2002 | Cole |
| 6,355,013 B1 | 3/2002 | van Muiden |
| 6,355,035 B1 | 3/2002 | Manushakian |
| 6,361,534 B1 | 3/2002 | Chen et al. |
| 6,364,879 B1 | 4/2002 | Chen et al. |
| 6,368,340 B2 | 4/2002 | Malecki et al. |
| 6,371,956 B1 | 4/2002 | Wilson et al. |
| 6,379,366 B1 | 4/2002 | Fleischman et al. |
| 6,383,195 B1 | 5/2002 | Richard |
| 6,383,197 B1 | 5/2002 | Conlon et al. |
| 6,387,671 B1 | 5/2002 | Rubinsky et al. |
| 6,391,029 B1 | 5/2002 | Hooven et al. |
| 6,398,708 B1 | 6/2002 | Hastings et al. |
| 6,402,735 B1 | 6/2002 | Langevin |
| 6,402,746 B1 | 6/2002 | Whayne et al. |
| 6,406,440 B1 | 6/2002 | Stefanchik |
| 6,409,727 B1 | 6/2002 | Bales et al. |
| 6,409,733 B1 | 6/2002 | Conlon et al. |
| 6,419,639 B2 | 7/2002 | Walther et al. |
| 6,419,641 B1 | 7/2002 | Mark et al. |
| 6,427,089 B1 | 7/2002 | Knowlton |
| 6,431,500 B1 | 8/2002 | Jacobs et al. |
| 6,436,107 B1 | 8/2002 | Wang et al. |
| 6,443,970 B1 | 9/2002 | Schulze et al. |
| 6,443,988 B2 | 9/2002 | Felt et al. |
| 6,447,511 B1 | 9/2002 | Slater |
| 6,447,523 B1 | 9/2002 | Middleman et al. |
| 6,454,783 B1 | 9/2002 | Piskun |
| 6,454,785 B2 | 9/2002 | De Hoyos Garza |
| 6,458,074 B1 | 10/2002 | Matsui et al. |
| 6,458,076 B1 | 10/2002 | Pruitt |
| 6,464,701 B1 | 10/2002 | Hooven et al. |
| 6,464,702 B2 | 10/2002 | Schulze et al. |
| 6,470,218 B1 | 10/2002 | Behl |
| 6,475,104 B1 | 11/2002 | Lutz et al. |
| 6,485,411 B1 | 11/2002 | Konstorum et al. |
| 6,489,745 B1 | 12/2002 | Koreis |
| 6,491,626 B1 | 12/2002 | Stone et al. |
| 6,491,627 B1 | 12/2002 | Komi |
| 6,491,691 B1 | 12/2002 | Morley et al. |
| 6,493,590 B1 | 12/2002 | Wessman et al. |
| 6,494,893 B2 | 12/2002 | Dubrul et al. |
| 6,500,176 B1 | 12/2002 | Truckai et al. |
| 6,503,192 B1 | 1/2003 | Ouchi |
| 6,506,190 B1 | 1/2003 | Walshe |
| 6,508,827 B1 | 1/2003 | Manhes |
| 6,514,239 B2 | 2/2003 | Shimmura et al. |
| 6,517,534 B1 | 2/2003 | McGovern et al. |
| 6,520,954 B2 | 2/2003 | Ouchi |
| 6,526,320 B2 | 2/2003 | Mitchell |
| 6,527,782 B2 | 3/2003 | Hogg et al. |
| 6,530,880 B2 | 3/2003 | Pagliuca |
| 6,530,922 B2 | 3/2003 | Cosman et al. |
| 6,535,764 B2 | 3/2003 | Imran et al. |
| 6,537,200 B2 | 3/2003 | Leysieffer et al. |
| 6,543,456 B1 | 4/2003 | Freeman |
| 6,551,270 B1 | 4/2003 | Bimbo et al. |
| 6,551,356 B2 | 4/2003 | Rousseau |
| 6,554,766 B2 | 4/2003 | Maeda et al. |
| 6,554,823 B2 | 4/2003 | Palmer et al. |
| 6,554,829 B2 | 4/2003 | Schulze et al. |
| 6,558,384 B2 | 5/2003 | Mayenberger |
| 6,562,034 B2 | 5/2003 | Edwards et al. |
| 6,562,035 B1 | 5/2003 | Levin |
| 6,562,052 B2 | 5/2003 | Nobles et al. |
| 6,569,120 B1 | 5/2003 | Green et al. |
| 6,569,159 B1 | 5/2003 | Edwards et al. |
| 6,572,629 B2 | 6/2003 | Kalloo et al. |
| 6,572,635 B1 | 6/2003 | Bonutti |
| 6,575,988 B2 | 6/2003 | Rousseau |
| 6,579,311 B1 | 6/2003 | Makower |
| 6,581,889 B2 | 6/2003 | Carpenter et al. |
| 6,585,642 B2 | 7/2003 | Christopher |
| 6,585,717 B1 | 7/2003 | Wittenberger et al. |
| 6,587,750 B2 | 7/2003 | Gerbi et al. |
| 6,592,559 B1 | 7/2003 | Pakter et al. |
| 6,592,603 B2 | 7/2003 | Lasner |
| 6,594,971 B1 | 7/2003 | Addy et al. |
| 6,602,262 B2 | 8/2003 | Griego et al. |
| 6,605,105 B1 | 8/2003 | Cuschieri et al. |
| 6,610,072 B1 | 8/2003 | Christy et al. |
| 6,610,074 B2 | 8/2003 | Santilli |
| 6,613,038 B2 | 9/2003 | Bonutti et al. |
| 6,613,068 B2 | 9/2003 | Ouchi |
| 6,616,632 B2 | 9/2003 | Sharp et al. |
| 6,620,193 B1 | 9/2003 | Lau et al. |
| 6,623,448 B2 | 9/2003 | Slater |
| 6,626,919 B1 | 9/2003 | Swanstrom |
| 6,632,171 B2 | 10/2003 | Iddan et al. |
| 6,632,229 B1 | 10/2003 | Yamanouchi |
| 6,632,234 B2 | 10/2003 | Kieturakis et al. |
| 6,638,275 B1 | 10/2003 | McGaffigan et al. |
| 6,638,286 B1 | 10/2003 | Burbank et al. |
| 6,645,225 B1 | 11/2003 | Atkinson |
| 6,652,518 B2 | 11/2003 | Wellman et al. |
| 6,652,521 B2 | 11/2003 | Schulze |
| 6,652,545 B2 | 11/2003 | Shipp et al. |
| 6,652,551 B1 | 11/2003 | Heiss |
| 6,656,194 B1 | 12/2003 | Gannoe et al. |
| 6,663,641 B1 | 12/2003 | Kovac et al. |
| 6,663,655 B2 | 12/2003 | Ginn et al. |
| 6,666,854 B1 | 12/2003 | Lange |
| 6,672,338 B1 | 1/2004 | Esashi et al. |
| 6,673,058 B2 | 1/2004 | Snow |
| 6,673,087 B1 | 1/2004 | Chang et al. |
| 6,673,092 B1 | 1/2004 | Bacher |
| 6,676,685 B2 | 1/2004 | Pedros et al. |
| 6,679,882 B1 | 1/2004 | Kornerup |
| 6,685,628 B2 | 2/2004 | Vu |
| 6,685,724 B1 | 2/2004 | Haluck |
| 6,692,445 B2 | 2/2004 | Roberts et al. |
| 6,692,462 B2 | 2/2004 | Mackenzie et al. |
| 6,692,493 B2 | 2/2004 | McGovern et al. |
| 6,699,180 B2 | 3/2004 | Kobayashi |
| 6,699,256 B2 | 3/2004 | Logan et al. |
| 6,699,263 B2 | 3/2004 | Cope |
| 6,706,018 B2 | 3/2004 | Westlund et al. |
| 6,708,066 B2 | 3/2004 | Herbst et al. |
| 6,709,188 B2 | 3/2004 | Ushimaru |
| 6,709,445 B2 | 3/2004 | Boebel et al. |
| 6,716,226 B2 | 4/2004 | Sixto, Jr. et al. |
| 6,731,875 B1 | 5/2004 | Kartalopoulos |
| 6,736,822 B2 | 5/2004 | McClellan et al. |
| 6,740,030 B2 | 5/2004 | Martone et al. |
| 6,740,082 B2 | 5/2004 | Shadduck |
| 6,743,166 B2 | 6/2004 | Berci et al. |
| 6,743,226 B2 | 6/2004 | Cosman et al. |
| 6,743,239 B1 | 6/2004 | Kuehn et al. |
| 6,743,240 B2 | 6/2004 | Smith et al. |
| 6,749,560 B1 | 6/2004 | Konstorum et al. |
| 6,749,609 B1 | 6/2004 | Lunsford et al. |
| 6,752,768 B2 | 6/2004 | Burdorff et al. |
| 6,752,811 B2 | 6/2004 | Chu et al. |
| 6,752,822 B2 | 6/2004 | Jespersen |
| 6,758,857 B2 | 7/2004 | Cioanta et al. |
| 6,761,685 B2 | 7/2004 | Adams et al. |
| 6,761,718 B2 | 7/2004 | Madsen |
| 6,761,722 B2 | 7/2004 | Cole et al. |
| 6,767,356 B2 | 7/2004 | Kanner et al. |
| 6,773,434 B2 | 8/2004 | Ciarrocca |
| 6,776,165 B2 | 8/2004 | Jin |

(56) References Cited

U.S. PATENT DOCUMENTS

| | | |
|---|---|---|
| 6,776,787 B2 | 8/2004 | Phung et al. |
| 6,780,151 B2 | 8/2004 | Grabover et al. |
| 6,780,352 B2 | 8/2004 | Jacobson |
| 6,783,491 B2 | 8/2004 | Saadat et al. |
| 6,786,382 B1 | 9/2004 | Hoffman |
| 6,786,864 B2 | 9/2004 | Matsuura et al. |
| 6,786,905 B2 | 9/2004 | Swanson et al. |
| 6,788,977 B2 | 9/2004 | Fenn et al. |
| 6,790,173 B2 | 9/2004 | Saadat et al. |
| 6,790,217 B2 | 9/2004 | Schulze et al. |
| 6,795,728 B2 | 9/2004 | Chornenky et al. |
| 6,800,056 B2 | 10/2004 | Tartaglia et al. |
| 6,808,491 B2 | 10/2004 | Kortenbach et al. |
| 6,817,974 B2 | 11/2004 | Cooper et al. |
| 6,818,007 B1 | 11/2004 | Dampney et al. |
| 6,824,548 B2 | 11/2004 | Smith et al. |
| 6,830,545 B2 | 12/2004 | Bendall |
| 6,836,688 B2 | 12/2004 | Ingle et al. |
| 6,837,847 B2 | 1/2005 | Ewers et al. |
| 6,840,246 B2 | 1/2005 | Downing |
| 6,840,938 B1 | 1/2005 | Morley et al. |
| 6,843,794 B2 | 1/2005 | Sixto, Jr. et al. |
| 6,861,250 B1 | 3/2005 | Cole et al. |
| 6,866,627 B2 | 3/2005 | Nozue |
| 6,866,628 B2 | 3/2005 | Goodman et al. |
| 6,869,394 B2 | 3/2005 | Ishibiki |
| 6,878,106 B1 | 4/2005 | Herrmann |
| 6,878,110 B2 | 4/2005 | Yang et al. |
| 6,881,213 B2 | 4/2005 | Ryan et al. |
| 6,881,216 B2 | 4/2005 | Di Caprio et al. |
| 6,884,213 B2 | 4/2005 | Raz et al. |
| 6,887,255 B2 | 5/2005 | Shimm |
| 6,889,089 B2 | 5/2005 | Behl et al. |
| 6,890,295 B2 | 5/2005 | Michels et al. |
| 6,896,683 B1 | 5/2005 | Gadberry et al. |
| 6,896,692 B2 | 5/2005 | Ginn et al. |
| 6,899,710 B2 | 5/2005 | Hooven |
| 6,908,427 B2 | 6/2005 | Fleener et al. |
| 6,908,476 B2 | 6/2005 | Jud et al. |
| 6,913,613 B2 | 7/2005 | Schwarz et al. |
| 6,916,284 B2 | 7/2005 | Moriyama |
| 6,918,871 B2 | 7/2005 | Schulze |
| 6,918,906 B2 | 7/2005 | Long |
| 6,918,908 B2 | 7/2005 | Bonner et al. |
| 6,926,723 B1 | 8/2005 | Mulhauser et al. |
| 6,926,725 B2 | 8/2005 | Cooke et al. |
| 6,932,810 B2 | 8/2005 | Ryan |
| 6,932,824 B1 | 8/2005 | Roop et al. |
| 6,932,827 B2 | 8/2005 | Cole |
| 6,932,834 B2 | 8/2005 | Lizardi et al. |
| 6,936,003 B2 | 8/2005 | Iddan |
| 6,939,290 B2 | 9/2005 | Iddan |
| 6,939,292 B2 | 9/2005 | Mizuno |
| 6,939,327 B2 | 9/2005 | Hall et al. |
| 6,942,613 B2 | 9/2005 | Ewers et al. |
| 6,944,490 B1 | 9/2005 | Chow |
| 6,945,472 B2 | 9/2005 | Wuttke et al. |
| 6,945,979 B2 | 9/2005 | Kortenbach et al. |
| 6,949,096 B2 | 9/2005 | Davison et al. |
| 6,955,641 B2 | 10/2005 | Lubock |
| 6,955,683 B2 | 10/2005 | Bonutti |
| 6,958,035 B2 | 10/2005 | Friedman et al. |
| 6,960,162 B2 | 11/2005 | Saadat et al. |
| 6,960,163 B2 | 11/2005 | Ewers et al. |
| 6,960,183 B2 | 11/2005 | Nicolette |
| 6,962,587 B2 | 11/2005 | Johnson et al. |
| 6,964,662 B2 | 11/2005 | Kidooka |
| 6,966,909 B2 | 11/2005 | Marshall et al. |
| 6,966,919 B2 | 11/2005 | Sixto, Jr. et al. |
| 6,967,462 B1 | 11/2005 | Landis |
| 6,971,988 B2 | 12/2005 | Orban, III |
| 6,972,017 B2 | 12/2005 | Smith et al. |
| 6,974,411 B2 | 12/2005 | Belson |
| 6,976,992 B2 | 12/2005 | Sachatello et al. |
| 6,984,203 B2 | 1/2006 | Tartaglia et al. |
| 6,984,205 B2 | 1/2006 | Gazdzinski |
| 6,986,738 B2 | 1/2006 | Glukhovsky et al. |
| 6,986,774 B2 | 1/2006 | Middleman et al. |
| 6,988,987 B2 | 1/2006 | Ishikawa et al. |
| 6,989,028 B2 | 1/2006 | Lashinski et al. |
| 6,991,602 B2 | 1/2006 | Nakazawa et al. |
| 6,991,627 B2 | 1/2006 | Madhani et al. |
| 6,991,631 B2 | 1/2006 | Woloszko et al. |
| 6,994,706 B2 | 2/2006 | Chornenky et al. |
| 6,994,708 B2 | 2/2006 | Manzo |
| 6,997,870 B2 | 2/2006 | Couvillon, Jr. |
| 6,997,931 B2 | 2/2006 | Sauer et al. |
| 7,000,818 B2 | 2/2006 | Shelton, IV et al. |
| 7,001,329 B2 | 2/2006 | Kobayashi et al. |
| 7,001,341 B2 | 2/2006 | Gellman et al. |
| 7,008,375 B2 | 3/2006 | Weisel |
| 7,008,419 B2 | 3/2006 | Shadduck |
| 7,009,634 B2 | 3/2006 | Iddan et al. |
| 7,010,340 B2 | 3/2006 | Scarantino et al. |
| 7,011,669 B2 | 3/2006 | Kimblad |
| 7,018,373 B2 | 3/2006 | Suzuki |
| 7,020,531 B1 | 3/2006 | Colliou et al. |
| 7,025,580 B2 | 4/2006 | Heagy et al. |
| 7,025,721 B2 | 4/2006 | Cohen et al. |
| 7,029,435 B2 | 4/2006 | Nakao |
| 7,029,438 B2 | 4/2006 | Morin et al. |
| 7,029,450 B2 | 4/2006 | Gellman |
| 7,032,600 B2 | 4/2006 | Fukuda et al. |
| 7,035,680 B2 | 4/2006 | Partridge et al. |
| 7,037,290 B2 | 5/2006 | Gardeski et al. |
| 7,041,052 B2 | 5/2006 | Saadat et al. |
| 7,052,454 B2 | 5/2006 | Taylor |
| 7,052,489 B2 | 5/2006 | Griego et al. |
| 7,056,330 B2 | 6/2006 | Gayton |
| 7,060,024 B2 | 6/2006 | Long et al. |
| 7,060,025 B2 | 6/2006 | Long et al. |
| 7,063,697 B2 | 6/2006 | Slater |
| 7,063,715 B2 | 6/2006 | Onuki et al. |
| 7,066,879 B2 | 6/2006 | Fowler et al. |
| 7,066,936 B2 | 6/2006 | Ryan |
| 7,070,559 B2 | 7/2006 | Adams et al. |
| 7,070,602 B2 | 7/2006 | Smith et al. |
| 7,076,305 B2 | 7/2006 | Imran et al. |
| 7,083,618 B2 | 8/2006 | Couture et al. |
| 7,083,620 B2 | 8/2006 | Jahns et al. |
| 7,083,629 B2 | 8/2006 | Weller et al. |
| 7,083,635 B2 | 8/2006 | Ginn |
| 7,087,010 B2 | 8/2006 | Ootawara et al. |
| 7,087,071 B2 | 8/2006 | Nicholas et al. |
| 7,088,923 B2 | 8/2006 | Haruyama |
| 7,090,673 B2 | 8/2006 | Dycus et al. |
| 7,090,683 B2 | 8/2006 | Brock et al. |
| 7,090,685 B2 | 8/2006 | Kortenbach et al. |
| 7,093,518 B2 | 8/2006 | Gmeilbauer |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,105,000 B2 | 9/2006 | McBrayer |
| 7,105,005 B2 | 9/2006 | Blake |
| 7,108,696 B2 | 9/2006 | Daniel et al. |
| 7,108,703 B2 | 9/2006 | Danitz et al. |
| 7,112,208 B2 | 9/2006 | Morris et al. |
| 7,115,092 B2 | 10/2006 | Park et al. |
| 7,115,124 B1 | 10/2006 | Xiao |
| 7,117,703 B2 | 10/2006 | Kato et al. |
| 7,118,531 B2 | 10/2006 | Krill |
| 7,118,578 B2 | 10/2006 | West, Jr. et al. |
| 7,118,587 B2 | 10/2006 | Dycus et al. |
| 7,128,708 B2 | 10/2006 | Saadat et al. |
| 7,130,697 B2 | 10/2006 | Chornenky et al. |
| RE39,415 E | 11/2006 | Bales et al. |
| 7,131,978 B2 | 11/2006 | Sancoff et al. |
| 7,131,979 B2 | 11/2006 | DiCarlo et al. |
| 7,131,980 B1 | 11/2006 | Field et al. |
| 7,137,980 B2 | 11/2006 | Buysse et al. |
| 7,137,981 B2 | 11/2006 | Long |
| 7,146,984 B2 | 12/2006 | Stack et al. |
| 7,147,650 B2 | 12/2006 | Lee |
| 7,150,097 B2 | 12/2006 | Sremcich et al. |

(56) References Cited

U.S. PATENT DOCUMENTS

| | | |
|---|---|---|
| 7,150,655 B2 | 12/2006 | Mastrototaro et al. |
| 7,150,750 B2 | 12/2006 | Damarati |
| 7,152,488 B2 | 12/2006 | Hedrich et al. |
| 7,153,321 B2 | 12/2006 | Andrews |
| 7,156,845 B2 | 1/2007 | Mulier et al. |
| 7,160,296 B2 | 1/2007 | Pearson et al. |
| 7,163,525 B2 | 1/2007 | Franer |
| 7,169,104 B2 | 1/2007 | Ueda et al. |
| 7,172,714 B2 | 2/2007 | Jacobson |
| 7,175,591 B2 | 2/2007 | Kaladelfos |
| 7,179,254 B2 | 2/2007 | Pendekanti et al. |
| 7,186,265 B2 | 3/2007 | Sharkawy et al. |
| 7,188,627 B2 | 3/2007 | Nelson et al. |
| 7,195,612 B2 | 3/2007 | Van Sloten et al. |
| 7,195,631 B2 | 3/2007 | Dumbauld |
| 7,204,820 B2 | 4/2007 | Akahoshi |
| 7,207,997 B2 | 4/2007 | Shipp et al. |
| 7,208,005 B2 | 4/2007 | Frecker et al. |
| 7,211,089 B2 | 5/2007 | Kear et al |
| 7,211,092 B2 | 5/2007 | Hughett |
| 7,220,227 B2 | 5/2007 | Sasaki et al. |
| 7,223,271 B2 | 5/2007 | Muramatsu et al. |
| 7,223,272 B2 | 5/2007 | Francere et al. |
| 7,229,438 B2 | 6/2007 | Young |
| 7,232,414 B2 | 6/2007 | Gonzalez |
| 7,232,445 B2 | 6/2007 | Kortenbach et al. |
| 7,235,089 B1 | 6/2007 | McGuckin, Jr. |
| 7,241,290 B2 | 7/2007 | Doyle et al. |
| 7,244,228 B2 | 7/2007 | Lubowski |
| 7,250,027 B2 | 7/2007 | Barry |
| 7,252,660 B2 | 8/2007 | Kunz |
| 7,255,675 B2 | 8/2007 | Gertner et al. |
| 7,261,725 B2 | 8/2007 | Binmoeller |
| 7,270,663 B2 | 9/2007 | Nakao |
| 7,288,075 B2 | 10/2007 | Parihar et al. |
| 7,291,127 B2 | 11/2007 | Eidenschink |
| 7,294,139 B1 | 11/2007 | Gengler |
| 7,301,250 B2 | 11/2007 | Cassel |
| 7,306,597 B2 | 12/2007 | Manzo |
| 7,308,828 B2 | 12/2007 | Hashimoto |
| 7,311,107 B2 | 12/2007 | Harel et al. |
| 7,318,802 B2 | 1/2008 | Suzuki et al. |
| 7,320,695 B2 | 1/2008 | Carroll |
| 7,322,934 B2 | 1/2008 | Miyake et al. |
| 7,323,006 B2 | 1/2008 | Andreas et al. |
| 7,329,256 B2 | 2/2008 | Johnson et al. |
| 7,329,257 B2 | 2/2008 | Kanehira et al. |
| 7,329,383 B2 | 2/2008 | Stinson |
| 7,335,220 B2 | 2/2008 | Khosravi et al. |
| 7,341,554 B2 | 3/2008 | Sekine et al. |
| 7,344,536 B1 | 3/2008 | Lunsford et al. |
| 7,352,387 B2 | 4/2008 | Yamamoto |
| 7,364,582 B2 | 4/2008 | Lee |
| 7,371,215 B2 | 5/2008 | Colliou et al. |
| 7,381,216 B2 | 6/2008 | Buzzard et al. |
| 7,390,324 B2 | 6/2008 | Whalen et al. |
| 7,393,322 B2 | 7/2008 | Wenchell |
| 7,402,162 B2 | 7/2008 | Ouchi |
| 7,404,791 B2 | 7/2008 | Linares et al. |
| 7,410,483 B2 | 8/2008 | Danitz et al. |
| 7,413,563 B2 | 8/2008 | Corcoran et al. |
| 7,416,554 B2 | 8/2008 | Lam et al. |
| 7,422,590 B2 | 9/2008 | Kupferschmid et al. |
| 7,435,229 B2 | 10/2008 | Wolf |
| 7,435,257 B2 | 10/2008 | Lashinski et al. |
| 7,441,507 B2 | 10/2008 | Teraura et al. |
| 7,442,166 B2 | 10/2008 | Huang et al. |
| 7,452,327 B2 | 11/2008 | Durgin et al. |
| 7,455,208 B2 | 11/2008 | Wales et al. |
| 7,455,675 B2 | 11/2008 | Schur et al. |
| 7,468,066 B2 | 12/2008 | Vargas et al. |
| 7,476,237 B2 | 1/2009 | Taniguchi et al. |
| 7,479,104 B2 | 1/2009 | Lau et al. |
| 7,485,093 B2 | 2/2009 | Glukhovsky |
| 7,488,295 B2 | 2/2009 | Burbank et al. |
| 7,494,499 B2 | 2/2009 | Nagase et al. |
| 7,497,867 B2 | 3/2009 | Lasner et al. |
| 7,498,950 B1 | 3/2009 | Ertas et al. |
| 7,507,200 B2 | 3/2009 | Okada |
| 7,507,239 B2 | 3/2009 | Shadduck |
| 7,510,107 B2 | 3/2009 | Timm et al. |
| 7,511,733 B2 | 3/2009 | Takizawa et al. |
| 7,515,953 B2 | 4/2009 | Madar et al. |
| 7,520,876 B2 | 4/2009 | Ressemann et al. |
| 7,524,281 B2 | 4/2009 | Chu et al. |
| 7,524,302 B2 | 4/2009 | Tower |
| 7,534,228 B2 | 5/2009 | Williams |
| 7,540,872 B2 | 6/2009 | Schechter et al. |
| 7,542,807 B2 | 6/2009 | Bertolero et al. |
| 7,544,203 B2 | 6/2009 | Chin et al. |
| 7,548,040 B2 | 6/2009 | Lee et al. |
| 7,549,564 B2 | 6/2009 | Boudreaux |
| 7,549,991 B2 | 6/2009 | Lu et al. |
| 7,549,998 B2 | 6/2009 | Braun |
| 7,553,278 B2 | 6/2009 | Kucklick |
| 7,553,298 B2 | 6/2009 | Hunt et al. |
| 7,559,452 B2 | 7/2009 | Wales et al. |
| 7,559,887 B2 | 7/2009 | Dannan |
| 7,559,916 B2 | 7/2009 | Smith et al. |
| 7,560,006 B2 | 7/2009 | Rakos et al. |
| 7,561,907 B2 | 7/2009 | Fuimaono et al. |
| 7,561,916 B2 | 7/2009 | Hunt et al. |
| 7,565,201 B2 | 7/2009 | Blackmore et al. |
| 7,566,334 B2 | 7/2009 | Christian et al. |
| 7,575,144 B2 | 8/2009 | Ortiz et al. |
| 7,575,548 B2 | 8/2009 | Takemoto et al. |
| 7,579,550 B2 | 8/2009 | Dayton et al. |
| 7,582,096 B2 | 9/2009 | Gellman et al. |
| 7,588,177 B2 | 9/2009 | Racenet |
| 7,588,557 B2 | 9/2009 | Nakao |
| 7,591,781 B2 | 9/2009 | Hirata |
| 7,597,229 B2 | 10/2009 | Boudreaux et al. |
| 7,604,150 B2 | 10/2009 | Boudreaux |
| 7,608,083 B2 | 10/2009 | Lee et al. |
| 7,611,479 B2 | 11/2009 | Cragg et al. |
| 7,615,002 B2 | 11/2009 | Rothweiler et al. |
| 7,615,005 B2 | 11/2009 | Stefanchik et al. |
| 7,618,398 B2 | 11/2009 | Holman et al. |
| 7,621,936 B2 | 11/2009 | Cragg et al. |
| 7,632,250 B2 | 12/2009 | Smith et al. |
| 7,635,373 B2 | 12/2009 | Ortiz |
| 7,637,903 B2 | 12/2009 | Lentz et al. |
| 7,648,519 B2 | 1/2010 | Lee et al. |
| 7,650,742 B2 | 1/2010 | Ushijima |
| 7,651,483 B2 | 1/2010 | Byrum et al. |
| 7,651,509 B2 | 1/2010 | Bojarski et al. |
| 7,653,438 B2 | 1/2010 | Deem et al. |
| 7,654,431 B2 | 2/2010 | Hueil et al. |
| 7,655,004 B2 | 2/2010 | Long |
| 7,662,089 B2 | 2/2010 | Okada et al. |
| 7,666,180 B2 | 2/2010 | Holsten et al. |
| 7,666,203 B2 | 2/2010 | Chanduszko et al. |
| 7,670,282 B2 | 3/2010 | Mathis |
| 7,670,336 B2 | 3/2010 | Young et al. |
| 7,674,259 B2 | 3/2010 | Shadduck |
| 7,678,043 B2 | 3/2010 | Gilad |
| 7,680,543 B2 | 3/2010 | Azure |
| 7,684,599 B2 | 3/2010 | Horn et al. |
| 7,684,851 B2 | 3/2010 | Miyake et al. |
| 7,686,826 B2 | 3/2010 | Lee et al. |
| 7,697,970 B2 | 4/2010 | Uchiyama et al. |
| 7,699,835 B2 | 4/2010 | Lee et al. |
| 7,699,864 B2 | 4/2010 | Kick et al. |
| 7,713,189 B2 | 5/2010 | Hanke |
| 7,713,270 B2 | 5/2010 | Suzuki |
| 7,721,742 B2 | 5/2010 | Kalloo et al. |
| 7,736,374 B2 | 6/2010 | Vaughan et al. |
| 7,744,615 B2 | 6/2010 | Couture |
| 7,749,161 B2 | 7/2010 | Beckman et al. |
| 7,751,866 B2 | 7/2010 | Aoki et al. |
| 7,753,901 B2 | 7/2010 | Piskun et al. |
| 7,753,933 B2 | 7/2010 | Ginn et al. |
| 7,758,577 B2 | 7/2010 | Nobis et al. |
| 7,762,949 B2 | 7/2010 | Nakao |

(56) References Cited

U.S. PATENT DOCUMENTS

| | | | |
|---|---|---|---|
| 7,762,998 | B2 | 7/2010 | Birk et al. |
| 7,763,012 | B2 | 7/2010 | Petrick et al. |
| 7,765,010 | B2 | 7/2010 | Chornenky et al. |
| 7,766,896 | B2 | 8/2010 | Kornkven Volk et al. |
| 7,770,584 | B2 | 8/2010 | Danek et al. |
| 7,771,416 | B2 | 8/2010 | Spivey et al. |
| 7,771,437 | B2 | 8/2010 | Hogg et al. |
| 7,780,683 | B2 | 8/2010 | Roue et al. |
| 7,780,691 | B2 | 8/2010 | Stefanchik |
| 7,784,663 | B2 | 8/2010 | Shelton, IV |
| 7,794,409 | B2 | 9/2010 | Damarati |
| 7,794,447 | B2 | 9/2010 | Dann et al. |
| 7,794,458 | B2 | 9/2010 | McIntyre et al. |
| 7,794,475 | B2 | 9/2010 | Hess et al. |
| 7,798,386 | B2 | 9/2010 | Schall et al. |
| 7,815,565 | B2 | 10/2010 | Stefanchik et al. |
| 7,815,566 | B2 | 10/2010 | Stefanchik et al. |
| 7,815,659 | B2 | 10/2010 | Conlon et al. |
| 7,815,662 | B2 | 10/2010 | Spivey et al. |
| 7,819,836 | B2 | 10/2010 | Levine et al. |
| 7,828,186 | B2 | 11/2010 | Wales |
| 7,833,156 | B2 | 11/2010 | Williams et al. |
| 7,833,238 | B2 | 11/2010 | Nakao |
| 7,837,615 | B2 | 11/2010 | Le et al. |
| 7,842,028 | B2 | 11/2010 | Lee |
| 7,842,068 | B2 | 11/2010 | Ginn |
| 7,846,171 | B2 | 12/2010 | Kullas et al. |
| 7,850,660 | B2 | 12/2010 | Uth et al. |
| 7,857,183 | B2 | 12/2010 | Shelton, IV |
| 7,862,546 | B2 | 1/2011 | Conlon et al. |
| 7,862,553 | B2 | 1/2011 | Ewaschuk |
| 7,867,216 | B2 | 1/2011 | Wahr et al. |
| 7,871,371 | B2 | 1/2011 | Komiya et al. |
| 7,879,004 | B2 | 2/2011 | Seibel et al. |
| 7,883,458 | B2 | 2/2011 | Hamel |
| 7,887,530 | B2 | 2/2011 | Zemlok et al. |
| 7,887,558 | B2 | 2/2011 | Lin et al. |
| 7,892,220 | B2 | 2/2011 | Faller et al. |
| 7,896,804 | B2 | 3/2011 | Uchimura et al. |
| 7,896,887 | B2 | 3/2011 | Rimbaugh et al. |
| 7,905,828 | B2 | 3/2011 | Brock et al. |
| 7,909,809 | B2 | 3/2011 | Scopton et al. |
| 7,914,513 | B2 | 3/2011 | Voorhees, Jr. |
| 7,918,785 | B2 | 4/2011 | Okada et al. |
| 7,918,869 | B2 | 4/2011 | Saadat et al. |
| 7,922,743 | B2 | 4/2011 | Heinrich et al. |
| 7,927,271 | B2 | 4/2011 | Dimitriou et al. |
| 7,931,624 | B2 | 4/2011 | Smith et al. |
| 7,937,143 | B2 | 5/2011 | Demarais et al. |
| 7,945,332 | B2 | 5/2011 | Schechter |
| 7,947,000 | B2 | 5/2011 | Vargas et al. |
| 7,953,326 | B2 | 5/2011 | Farr et al. |
| 7,955,298 | B2 | 6/2011 | Carroll et al. |
| 7,959,627 | B2 * | 6/2011 | Utley ........... A61B 18/1492 606/41 |
| 7,959,629 | B2 | 6/2011 | Young et al. |
| 7,963,975 | B2 | 6/2011 | Criscuolo |
| 7,965,180 | B2 | 6/2011 | Koyama |
| 7,967,808 | B2 | 6/2011 | Fitzgerald et al. |
| 7,969,473 | B2 | 6/2011 | Kotoda |
| 7,972,330 | B2 | 7/2011 | Alejandro et al. |
| 7,976,458 | B2 | 7/2011 | Stefanchik et al. |
| 7,976,552 | B2 | 7/2011 | Suzuki |
| 7,985,239 | B2 | 7/2011 | Suzuki |
| 7,988,618 | B2 | 8/2011 | Mikkaichi et al. |
| 7,988,685 | B2 | 8/2011 | Ziaie et al. |
| 8,021,362 | B2 | 9/2011 | Deem et al. |
| 8,029,504 | B2 | 10/2011 | Long |
| 8,034,046 | B2 | 10/2011 | Eidenschink |
| 8,037,591 | B2 | 10/2011 | Spivey et al. |
| 8,048,067 | B2 | 11/2011 | Davalos et al. |
| 8,048,108 | B2 | 11/2011 | Sibbitt et al. |
| 8,052,699 | B1 | 11/2011 | Sherwinter |
| 8,057,510 | B2 | 11/2011 | Ginn et al. |
| 8,062,306 | B2 | 11/2011 | Nobis et al. |
| 8,062,311 | B2 | 11/2011 | Litscher et al. |
| 8,066,632 | B2 | 11/2011 | Dario et al. |
| 8,066,702 | B2 | 11/2011 | Rittman, III et al. |
| 8,070,759 | B2 | 12/2011 | Stefanchik et al. |
| 8,070,804 | B2 | 12/2011 | Hyde et al. |
| 8,075,572 | B2 | 12/2011 | Stefanchik et al. |
| 8,075,587 | B2 | 12/2011 | Ginn |
| 8,088,062 | B2 | 1/2012 | Zwolinski |
| 8,096,459 | B2 | 1/2012 | Ortiz et al. |
| 8,096,941 | B2 | 1/2012 | Fowler et al. |
| 8,100,922 | B2 | 1/2012 | Griffith |
| 8,109,872 | B2 | 2/2012 | Kennedy, II et al. |
| 8,114,072 | B2 | 2/2012 | Long et al. |
| 8,114,119 | B2 | 2/2012 | Spivey et al. |
| 8,118,821 | B2 | 2/2012 | Mouw |
| 8,118,834 | B1 | 2/2012 | Goraltchouk et al. |
| 8,131,371 | B2 | 3/2012 | Demarals et al. |
| 8,147,424 | B2 | 4/2012 | Kassab et al. |
| 8,157,813 | B2 | 4/2012 | Ko et al. |
| 8,157,834 | B2 | 4/2012 | Conlon |
| 8,172,772 | B2 | 5/2012 | Zwolinski et al. |
| 8,182,414 | B2 | 5/2012 | Handa et al. |
| 8,187,166 | B2 | 5/2012 | Kuth et al. |
| 8,200,334 | B1 | 6/2012 | Min et al. |
| 8,206,295 | B2 | 6/2012 | Kaul |
| 8,211,125 | B2 | 7/2012 | Spivey |
| 8,216,224 | B2 | 7/2012 | Morris et al. |
| 8,221,310 | B2 | 7/2012 | Saadat et al. |
| 8,241,204 | B2 | 8/2012 | Spivey |
| 8,251,068 | B2 | 8/2012 | Schnell |
| 8,252,057 | B2 | 8/2012 | Fox |
| 8,262,563 | B2 | 9/2012 | Bakos et al. |
| 8,262,655 | B2 | 9/2012 | Ghabrial et al. |
| 8,262,680 | B2 | 9/2012 | Swain et al. |
| 8,267,854 | B2 | 9/2012 | Asada et al. |
| 8,303,581 | B2 | 11/2012 | Arts et al. |
| 8,308,738 | B2 | 11/2012 | Nobis et al. |
| 8,317,806 | B2 | 11/2012 | Coe et al. |
| 8,317,814 | B2 | 11/2012 | Karasawa et al. |
| 8,328,836 | B2 | 12/2012 | Conlon et al. |
| 8,337,394 | B2 | 12/2012 | Vakharia |
| 8,337,492 | B2 | 12/2012 | Kunis et al. |
| 8,343,041 | B2 | 1/2013 | Byers et al. |
| 8,353,487 | B2 | 1/2013 | Trusty et al. |
| 8,357,170 | B2 | 1/2013 | Stefanchik |
| 8,359,093 | B2 | 1/2013 | Wariar |
| 8,361,066 | B2 | 1/2013 | Long et al. |
| 8,361,112 | B2 | 1/2013 | Carroll, II et al. |
| 8,403,926 | B2 | 3/2013 | Nobis et al. |
| 8,409,200 | B2 | 4/2013 | Holcomb et al. |
| 8,425,505 | B2 | 4/2013 | Long |
| 8,430,811 | B2 | 4/2013 | Hess et al. |
| 8,449,452 | B2 | 5/2013 | Iddan et al. |
| 8,449,538 | B2 | 5/2013 | Long |
| 8,454,594 | B2 | 6/2013 | Demarais et al. |
| 8,475,359 | B2 | 7/2013 | Asada et al. |
| 8,480,657 | B2 | 7/2013 | Bakos |
| 8,480,689 | B2 | 7/2013 | Spivey et al. |
| 8,485,968 | B2 | 7/2013 | Weimer et al. |
| 8,496,574 | B2 | 7/2013 | Trusty et al. |
| 8,500,697 | B2 | 8/2013 | Kurth et al. |
| 8,506,564 | B2 | 8/2013 | Long et al. |
| 8,523,939 | B1 | 9/2013 | Hausen |
| 8,529,563 | B2 | 9/2013 | Long et al. |
| 8,545,396 | B2 | 10/2013 | Cover et al. |
| 8,568,410 | B2 | 10/2013 | Vakharia et al. |
| 8,579,897 | B2 | 11/2013 | Vakharia et al. |
| 8,608,652 | B2 | 12/2013 | Voegele et al. |
| 8,623,011 | B2 | 1/2014 | Spivey |
| 8,636,648 | B2 | 1/2014 | Gazdzinski |
| 8,636,730 | B2 | 1/2014 | Keppel |
| 8,652,150 | B2 | 2/2014 | Swain et al. |
| 8,668,686 | B2 | 3/2014 | Govari et al. |
| 8,679,003 | B2 | 3/2014 | Spivey |
| 8,727,967 | B2 | 5/2014 | Weitzner |
| 8,747,401 | B2 | 6/2014 | Gonzalez et al. |
| 8,753,335 | B2 | 6/2014 | Moshe et al. |
| 8,771,173 | B2 | 7/2014 | Fonger et al. |
| 8,771,260 | B2 | 7/2014 | Conlon et al. |

(56) References Cited

U.S. PATENT DOCUMENTS

| | | |
|---|---|---|
| 8,828,031 B2 | 9/2014 | Fox et al. |
| 8,880,185 B2 | 11/2014 | Hastings et al. |
| 8,888,792 B2 | 11/2014 | Harris et al. |
| 8,906,035 B2 | 12/2014 | Zwolinski et al. |
| 2001/0023333 A1 | 9/2001 | Wise et al. |
| 2002/0022771 A1 | 2/2002 | Diokno et al. |
| 2002/0022857 A1 | 2/2002 | Goldsteen et al. |
| 2002/0023353 A1 | 2/2002 | Ting-Kung |
| 2002/0029055 A1 | 3/2002 | Bonutti |
| 2002/0042562 A1 | 4/2002 | Meron et al. |
| 2002/0049439 A1 | 4/2002 | Mulier et al. |
| 2002/0068945 A1 | 6/2002 | Sixto, Jr. et al. |
| 2002/0078967 A1 | 6/2002 | Sixto, Jr. et al. |
| 2002/0082516 A1 | 6/2002 | Stefanchik |
| 2002/0082551 A1 | 6/2002 | Yachia et al. |
| 2002/0095164 A1 | 7/2002 | Andreas et al. |
| 2002/0107530 A1 | 8/2002 | Sauer et al. |
| 2002/0133115 A1 | 9/2002 | Gordon et al. |
| 2002/0138086 A1 | 9/2002 | Sixto, Jr. et al. |
| 2002/0147456 A1 | 10/2002 | Diduch et al. |
| 2002/0165592 A1 | 11/2002 | Glukhovsky et al. |
| 2002/0173805 A1 | 11/2002 | Matsuno et al. |
| 2002/0183591 A1 | 12/2002 | Matsuura et al. |
| 2003/0014090 A1 | 1/2003 | Abrahamson |
| 2003/0018373 A1 | 1/2003 | Eckhardt et al. |
| 2003/0023255 A1 | 1/2003 | Miles et al. |
| 2003/0036679 A1 | 2/2003 | Kortenbach et al. |
| 2003/0069602 A1 | 4/2003 | Jacobs et al. |
| 2003/0078471 A1 | 4/2003 | Foley et al. |
| 2003/0083681 A1 | 5/2003 | Moutafis et al. |
| 2003/0114731 A1 | 6/2003 | Cadeddu et al. |
| 2003/0114732 A1 | 6/2003 | Webler et al. |
| 2003/0120257 A1 | 6/2003 | Houston et al. |
| 2003/0124009 A1 | 7/2003 | Ravi et al. |
| 2003/0130564 A1 | 7/2003 | Martone et al. |
| 2003/0130656 A1 | 7/2003 | Levin |
| 2003/0139646 A1 | 7/2003 | Sharrow et al. |
| 2003/0158521 A1 | 8/2003 | Ameri |
| 2003/0167062 A1 | 9/2003 | Gambale et al. |
| 2003/0171651 A1 | 9/2003 | Page et al. |
| 2003/0176880 A1 | 9/2003 | Long et al. |
| 2003/0187351 A1 | 10/2003 | Franck et al. |
| 2003/0216611 A1 | 11/2003 | Vu |
| 2003/0216615 A1 | 11/2003 | Ouchi |
| 2003/0220545 A1 | 11/2003 | Ouchi |
| 2003/0225312 A1 | 12/2003 | Suzuki et al. |
| 2003/0225332 A1 | 12/2003 | Okada et al. |
| 2003/0229269 A1 | 12/2003 | Humphrey |
| 2003/0229371 A1 | 12/2003 | Whitworth |
| 2003/0236549 A1 | 12/2003 | Bonadio et al. |
| 2004/0002683 A1 | 1/2004 | Nicholson et al. |
| 2004/0024414 A1 | 2/2004 | Downing |
| 2004/0034369 A1 | 2/2004 | Sauer et al. |
| 2004/0054322 A1 | 3/2004 | Vargas |
| 2004/0098007 A1 | 5/2004 | Heiss |
| 2004/0101456 A1 | 5/2004 | Kuroshima et al. |
| 2004/0104999 A1 | 6/2004 | Okada |
| 2004/0116948 A1 | 6/2004 | Sixto, Jr. et al. |
| 2004/0127940 A1 | 7/2004 | Ginn et al. |
| 2004/0133077 A1 | 7/2004 | Obenchain et al. |
| 2004/0133089 A1 | 7/2004 | Kilcoyne et al. |
| 2004/0136779 A1 | 7/2004 | Bhaskar |
| 2004/0138525 A1 | 7/2004 | Saadat et al. |
| 2004/0138529 A1 | 7/2004 | Wiltshire et al. |
| 2004/0138587 A1 | 7/2004 | Lyons, IV |
| 2004/0161451 A1 | 8/2004 | Pierce et al. |
| 2004/0167545 A1 | 8/2004 | Sadler et al. |
| 2004/0176699 A1 | 9/2004 | Walker et al. |
| 2004/0186350 A1 | 9/2004 | Brenneman et al. |
| 2004/0193009 A1 | 9/2004 | Jaffe et al. |
| 2004/0193146 A1 | 9/2004 | Lee et al. |
| 2004/0193186 A1 | 9/2004 | Kortenbach et al. |
| 2004/0193188 A1 | 9/2004 | Francese |
| 2004/0193189 A1 | 9/2004 | Kortenbach et al. |
| 2004/0193200 A1 | 9/2004 | Dworschak et al. |
| 2004/0199052 A1 | 10/2004 | Banik et al. |
| 2004/0199159 A1 | 10/2004 | Lee et al. |
| 2004/0206859 A1 | 10/2004 | Chong et al. |
| 2004/0210245 A1 | 10/2004 | Erickson et al. |
| 2004/0215058 A1 | 10/2004 | Zirps et al. |
| 2004/0225183 A1 | 11/2004 | Michlitsch et al. |
| 2004/0225186 A1 | 11/2004 | Horne, Jr. et al. |
| 2004/0225323 A1 | 11/2004 | Nagase et al. |
| 2004/0230095 A1 | 11/2004 | Stefanchik et al. |
| 2004/0230096 A1 | 11/2004 | Stefanchik et al. |
| 2004/0230161 A1 | 11/2004 | Zeiner |
| 2004/0243108 A1 | 12/2004 | Suzuki |
| 2004/0249246 A1 | 12/2004 | Campos |
| 2004/0249367 A1 | 12/2004 | Saadat et al. |
| 2004/0249394 A1 | 12/2004 | Morris et al. |
| 2004/0249443 A1 | 12/2004 | Shanley et al. |
| 2004/0254572 A1 | 12/2004 | McIntyre et al. |
| 2004/0260198 A1 | 12/2004 | Rothberg et al. |
| 2004/0260315 A1 | 12/2004 | Dell et al. |
| 2004/0260337 A1 | 12/2004 | Freed |
| 2005/0004515 A1 | 1/2005 | Hart et al. |
| 2005/0033265 A1 | 2/2005 | Engel et al. |
| 2005/0033277 A1 | 2/2005 | Clague et al. |
| 2005/0033319 A1 | 2/2005 | Gambale et al. |
| 2005/0033333 A1 | 2/2005 | Smith et al. |
| 2005/0043690 A1 | 2/2005 | Todd |
| 2005/0049616 A1 | 3/2005 | Rivera et al. |
| 2005/0059963 A1 | 3/2005 | Phan et al. |
| 2005/0059964 A1 | 3/2005 | Fitz |
| 2005/0065397 A1 | 3/2005 | Saadat et al. |
| 2005/0065509 A1 | 3/2005 | Coldwell et al. |
| 2005/0065517 A1 | 3/2005 | Chin |
| 2005/0070754 A1 | 3/2005 | Nobis et al. |
| 2005/0070763 A1 | 3/2005 | Nobis et al. |
| 2005/0070764 A1 | 3/2005 | Nobis et al. |
| 2005/0070947 A1 | 3/2005 | Franer et al. |
| 2005/0080413 A1 | 4/2005 | Canady |
| 2005/0080435 A1 | 4/2005 | Smith et al. |
| 2005/0085693 A1 | 4/2005 | Belson et al. |
| 2005/0085832 A1 | 4/2005 | Sancoff et al. |
| 2005/0090837 A1 | 4/2005 | Sixto, Jr. et al. |
| 2005/0090838 A1 | 4/2005 | Sixto, Jr. et al. |
| 2005/0096502 A1 | 5/2005 | Khalili |
| 2005/0101837 A1 | 5/2005 | Kalloo et al. |
| 2005/0101838 A1 | 5/2005 | Camillocci et al. |
| 2005/0101984 A1 | 5/2005 | Chanduszko et al. |
| 2005/0107663 A1 | 5/2005 | Saadat et al. |
| 2005/0107664 A1 | 5/2005 | Kalloo et al. |
| 2005/0110881 A1 | 5/2005 | Glukhovsky et al. |
| 2005/0113847 A1 | 5/2005 | Gadberry et al. |
| 2005/0119613 A1 | 6/2005 | Moenning et al. |
| 2005/0124855 A1 | 6/2005 | Jaffe et al. |
| 2005/0125010 A1 | 6/2005 | Smith et al. |
| 2005/0131279 A1 | 6/2005 | Boulais et al. |
| 2005/0131457 A1 | 6/2005 | Douglas et al. |
| 2005/0137454 A1 | 6/2005 | Saadat et al. |
| 2005/0143647 A1 | 6/2005 | Minai et al. |
| 2005/0143690 A1 | 6/2005 | High |
| 2005/0143774 A1 | 6/2005 | Polo |
| 2005/0143803 A1 | 6/2005 | Watson et al. |
| 2005/0149087 A1 | 7/2005 | Ahlberg et al. |
| 2005/0149096 A1 | 7/2005 | Hilal et al. |
| 2005/0159648 A1 | 7/2005 | Freed |
| 2005/0165272 A1 | 7/2005 | Okada et al. |
| 2005/0165378 A1 | 7/2005 | Heinrich et al. |
| 2005/0165411 A1 | 7/2005 | Orban, III |
| 2005/0165429 A1 | 7/2005 | Douglas et al. |
| 2005/0182429 A1 | 8/2005 | Yamanouchi |
| 2005/0192478 A1 | 9/2005 | Williams et al. |
| 2005/0192598 A1 | 9/2005 | Johnson et al. |
| 2005/0192602 A1 | 9/2005 | Manzo |
| 2005/0192654 A1 | 9/2005 | Chanduszko et al. |
| 2005/0209624 A1 | 9/2005 | Vijay |
| 2005/0215858 A1 | 9/2005 | Vail, III |
| 2005/0216036 A1 | 9/2005 | Nakao |
| 2005/0216050 A1 | 9/2005 | Sepetka et al. |
| 2005/0228224 A1 | 10/2005 | Okada et al. |
| 2005/0228406 A1 | 10/2005 | Bose |
| 2005/0234297 A1 | 10/2005 | Devierre et al. |

(56) References Cited

U.S. PATENT DOCUMENTS

| | | |
|---|---|---|
| 2005/0240249 A1 | 10/2005 | Tu et al. |
| 2005/0250983 A1 | 11/2005 | Tremaglio et al. |
| 2005/0250987 A1 | 11/2005 | Ewers et al. |
| 2005/0250990 A1 | 11/2005 | Le et al. |
| 2005/0250993 A1 | 11/2005 | Jaeger |
| 2005/0251166 A1 | 11/2005 | Vaughan et al. |
| 2005/0251176 A1 | 11/2005 | Swanstrom et al. |
| 2005/0261674 A1 | 11/2005 | Nobis et al. |
| 2005/0267492 A1 | 12/2005 | Poncet et al. |
| 2005/0272975 A1 | 12/2005 | McWeeney et al. |
| 2005/0272977 A1 | 12/2005 | Saadat et al. |
| 2005/0273084 A1 | 12/2005 | Hinman et al. |
| 2005/0274935 A1 | 12/2005 | Nelson |
| 2005/0277945 A1 | 12/2005 | Saadat et al. |
| 2005/0277951 A1 | 12/2005 | Smith et al. |
| 2005/0277952 A1 | 12/2005 | Arp et al. |
| 2005/0277954 A1 | 12/2005 | Smith et al. |
| 2005/0277955 A1 | 12/2005 | Palmer et al. |
| 2005/0277956 A1 | 12/2005 | Francese et al. |
| 2005/0277957 A1 | 12/2005 | Kuhns et al. |
| 2005/0283118 A1 | 12/2005 | Uth et al. |
| 2005/0283119 A1 | 12/2005 | Uth et al. |
| 2005/0288555 A1 | 12/2005 | Binmoeller |
| 2006/0004406 A1 | 1/2006 | Wehrstein et al. |
| 2006/0004409 A1 | 1/2006 | Nobis et al. |
| 2006/0004410 A1 | 1/2006 | Nobis et al. |
| 2006/0015009 A1 | 1/2006 | Jaffe et al. |
| 2006/0015131 A1 | 1/2006 | Kierce et al. |
| 2006/0020167 A1 | 1/2006 | Sitzmann |
| 2006/0020247 A1 | 1/2006 | Kagan et al. |
| 2006/0025654 A1 | 2/2006 | Suzuki et al. |
| 2006/0025781 A1 | 2/2006 | Young et al. |
| 2006/0025812 A1 | 2/2006 | Shelton, IV |
| 2006/0025819 A1 | 2/2006 | Nobis et al. |
| 2006/0036267 A1 | 2/2006 | Saadat et al. |
| 2006/0041188 A1 | 2/2006 | Dirusso et al. |
| 2006/0058582 A1 | 3/2006 | Maahs et al. |
| 2006/0058776 A1 | 3/2006 | Bilsbury |
| 2006/0064083 A1 | 3/2006 | Khalaj et al. |
| 2006/0069396 A1 | 3/2006 | Meade et al. |
| 2006/0069424 A1 | 3/2006 | Acosta et al. |
| 2006/0069425 A1 | 3/2006 | Hillis et al. |
| 2006/0069429 A1 | 3/2006 | Spence et al. |
| 2006/0074413 A1 | 4/2006 | Behzadian |
| 2006/0079890 A1 | 4/2006 | Guerra |
| 2006/0089528 A1 | 4/2006 | Tartaglia et al. |
| 2006/0095031 A1 | 5/2006 | Ormsby |
| 2006/0095060 A1 | 5/2006 | Mayenberger et al. |
| 2006/0100687 A1 | 5/2006 | Fahey et al. |
| 2006/0106423 A1 | 5/2006 | Weisel et al. |
| 2006/0111209 A1 | 5/2006 | Hinman et al. |
| 2006/0111210 A1 | 5/2006 | Hinman et al. |
| 2006/0111703 A1 | 5/2006 | Kunis et al. |
| 2006/0111704 A1 | 5/2006 | Brenneman et al. |
| 2006/0129166 A1 | 6/2006 | Lavelle |
| 2006/0135962 A1 | 6/2006 | Kick et al. |
| 2006/0135971 A1 | 6/2006 | Swanstrom et al. |
| 2006/0135984 A1 | 6/2006 | Kramer et al. |
| 2006/0142644 A1 | 6/2006 | Mulac et al. |
| 2006/0142652 A1 | 6/2006 | Keenan |
| 2006/0142790 A1 | 6/2006 | Gertner |
| 2006/0142798 A1 | 6/2006 | Holman et al. |
| 2006/0149129 A1 | 7/2006 | Watts et al. |
| 2006/0149131 A1 | 7/2006 | Or |
| 2006/0149132 A1 | 7/2006 | Iddan |
| 2006/0149135 A1 | 7/2006 | Paz |
| 2006/0161190 A1 | 7/2006 | Gadberry et al. |
| 2006/0167416 A1 | 7/2006 | Mathis et al. |
| 2006/0167482 A1 | 7/2006 | Swain et al. |
| 2006/0178560 A1 | 8/2006 | Saadat et al. |
| 2006/0183975 A1 | 8/2006 | Saadat et al. |
| 2006/0184161 A1 | 8/2006 | Maahs et al. |
| 2006/0189844 A1 | 8/2006 | Tien |
| 2006/0189845 A1 | 8/2006 | Maahs et al. |
| 2006/0190027 A1 | 8/2006 | Downey |
| 2006/0195084 A1 | 8/2006 | Slater |
| 2006/0200005 A1 | 9/2006 | Bjork et al. |
| 2006/0200121 A1 | 9/2006 | Mowery |
| 2006/0200169 A1 | 9/2006 | Sniffin |
| 2006/0200170 A1 | 9/2006 | Aranyi |
| 2006/0200199 A1 | 9/2006 | Bonutti et al. |
| 2006/0217665 A1 | 9/2006 | Prosek |
| 2006/0217697 A1 | 9/2006 | Lau et al. |
| 2006/0217742 A1 | 9/2006 | Messerly et al. |
| 2006/0217743 A1 | 9/2006 | Messerly et al. |
| 2006/0229639 A1 | 10/2006 | Whitfield |
| 2006/0229640 A1 | 10/2006 | Whitfield |
| 2006/0237022 A1 | 10/2006 | Chen et al. |
| 2006/0237023 A1 | 10/2006 | Cox et al. |
| 2006/0241570 A1 | 10/2006 | Wilk |
| 2006/0247500 A1 | 11/2006 | Voegele et al. |
| 2006/0247576 A1 | 11/2006 | Poncet |
| 2006/0247663 A1 | 11/2006 | Schwartz et al. |
| 2006/0247673 A1 | 11/2006 | Voegele et al. |
| 2006/0253004 A1 | 11/2006 | Frisch et al. |
| 2006/0253039 A1 | 11/2006 | McKenna et al. |
| 2006/0258907 A1 | 11/2006 | Stefanchik et al. |
| 2006/0258908 A1 | 11/2006 | Stefanchik et al. |
| 2006/0258910 A1 | 11/2006 | Stefanchik et al. |
| 2006/0258954 A1 | 11/2006 | Timberlake et al. |
| 2006/0258955 A1 | 11/2006 | Hoffman et al. |
| 2006/0259010 A1 | 11/2006 | Stefanchik et al. |
| 2006/0259073 A1 | 11/2006 | Miyamoto et al. |
| 2006/0264752 A1* | 11/2006 | Rubinsky et al. ............. 600/439 |
| 2006/0264904 A1 | 11/2006 | Kerby et al. |
| 2006/0264930 A1 | 11/2006 | Nishimura |
| 2006/0270902 A1 | 11/2006 | Igarashi et al. |
| 2006/0271042 A1 | 11/2006 | Latterell et al. |
| 2006/0271102 A1 | 11/2006 | Bosshard et al. |
| 2006/0276835 A1 | 12/2006 | Uchida |
| 2006/0281970 A1 | 12/2006 | Stokes et al. |
| 2006/0282106 A1 | 12/2006 | Cole et al. |
| 2006/0285732 A1 | 12/2006 | Horn et al. |
| 2006/0287644 A1 | 12/2006 | Inganas et al. |
| 2006/0287666 A1 | 12/2006 | Saadat et al. |
| 2006/0293626 A1 | 12/2006 | Byrum et al. |
| 2007/0000550 A1 | 1/2007 | Osinski |
| 2007/0002135 A1 | 1/2007 | Glukhovsky |
| 2007/0005019 A1 | 1/2007 | Okishige |
| 2007/0010801 A1 | 1/2007 | Chen et al. |
| 2007/0015965 A1 | 1/2007 | Cox et al. |
| 2007/0016225 A1 | 1/2007 | Nakao |
| 2007/0027469 A1 | 2/2007 | Smith et al. |
| 2007/0032700 A1 | 2/2007 | Fowler et al. |
| 2007/0032701 A1 | 2/2007 | Fowler et al. |
| 2007/0043261 A1 | 2/2007 | Watanabe et al. |
| 2007/0049800 A1 | 3/2007 | Boulais |
| 2007/0049902 A1 | 3/2007 | Griffin et al. |
| 2007/0049968 A1 | 3/2007 | Sibbitt et al. |
| 2007/0051375 A1 | 3/2007 | Milliman |
| 2007/0060880 A1 | 3/2007 | Gregorich et al. |
| 2007/0066869 A1 | 3/2007 | Hoffman |
| 2007/0067017 A1 | 3/2007 | Trapp |
| 2007/0073102 A1 | 3/2007 | Matsuno et al. |
| 2007/0073269 A1 | 3/2007 | Becker |
| 2007/0078439 A1 | 4/2007 | Grandt et al. |
| 2007/0079924 A1 | 4/2007 | Saadat et al. |
| 2007/0083195 A1 | 4/2007 | Werneth et al. |
| 2007/0088370 A1 | 4/2007 | Kahle et al. |
| 2007/0100375 A1 | 5/2007 | Mikkaichi et al. |
| 2007/0100376 A1 | 5/2007 | Mikkaichi et al. |
| 2007/0106113 A1 | 5/2007 | Ravo |
| 2007/0106118 A1 | 5/2007 | Moriyama |
| 2007/0106317 A1 | 5/2007 | Shelton, IV et al. |
| 2007/0112251 A1 | 5/2007 | Nakhuda |
| 2007/0112331 A1 | 5/2007 | Weber et al. |
| 2007/0112342 A1* | 5/2007 | Pearson et al. .................. 606/34 |
| 2007/0112383 A1 | 5/2007 | Conlon et al. |
| 2007/0112385 A1 | 5/2007 | Conlon |
| 2007/0112417 A1 | 5/2007 | Shanley et al. |
| 2007/0112425 A1 | 5/2007 | Schaller et al. |
| 2007/0118115 A1 | 5/2007 | Artale et al. |
| 2007/0123840 A1 | 5/2007 | Cox |
| 2007/0129605 A1 | 6/2007 | Schaaf |

(56) References Cited

U.S. PATENT DOCUMENTS

| | | |
|---|---|---|
| 2007/0129719 A1 | 6/2007 | Kendale et al. |
| 2007/0129760 A1 | 6/2007 | Demarais et al. |
| 2007/0135709 A1 | 6/2007 | Rioux et al. |
| 2007/0135803 A1 | 6/2007 | Belson |
| 2007/0142706 A1 | 6/2007 | Matsui et al. |
| 2007/0142710 A1 | 6/2007 | Yokoi et al. |
| 2007/0142779 A1 | 6/2007 | Duane et al. |
| 2007/0142780 A1 | 6/2007 | Van Lue |
| 2007/0154460 A1 | 7/2007 | Kraft et al. |
| 2007/0156028 A1 | 7/2007 | Van Lue et al. |
| 2007/0156116 A1 | 7/2007 | Gonzalez |
| 2007/0156127 A1 | 7/2007 | Rioux et al. |
| 2007/0161855 A1 | 7/2007 | Mikkaichi et al. |
| 2007/0162101 A1 | 7/2007 | Burgermeister et al. |
| 2007/0167901 A1 | 7/2007 | Herrig et al. |
| 2007/0173686 A1 | 7/2007 | Lin et al. |
| 2007/0173691 A1 | 7/2007 | Yokoi et al. |
| 2007/0173869 A1 | 7/2007 | Gannoe et al. |
| 2007/0173870 A2 | 7/2007 | Zacharias |
| 2007/0173872 A1 | 7/2007 | Neuenfeldt |
| 2007/0179525 A1 | 8/2007 | Frecker et al. |
| 2007/0179530 A1 | 8/2007 | Tieu et al. |
| 2007/0191904 A1 | 8/2007 | Libbus et al. |
| 2007/0197865 A1 | 8/2007 | Miyake et al. |
| 2007/0198057 A1 | 8/2007 | Gelbart et al. |
| 2007/0203398 A1 | 8/2007 | Bonadio et al. |
| 2007/0203487 A1 | 8/2007 | Sugita |
| 2007/0208336 A1 | 9/2007 | Kim et al. |
| 2007/0208364 A1 | 9/2007 | Smith et al. |
| 2007/0208407 A1 | 9/2007 | Gerdts et al. |
| 2007/0213754 A1 | 9/2007 | Mikkaichi et al. |
| 2007/0225552 A1 | 9/2007 | Segawa et al. |
| 2007/0225554 A1 | 9/2007 | Maseda et al. |
| 2007/0233040 A1 | 10/2007 | Macnamara et al. |
| 2007/0244356 A1 | 10/2007 | Carrillo, Jr. et al. |
| 2007/0244358 A1 | 10/2007 | Lee |
| 2007/0250038 A1 | 10/2007 | Boulais |
| 2007/0250057 A1 | 10/2007 | Nobis et al. |
| 2007/0255096 A1 | 11/2007 | Stefanchik et al. |
| 2007/0255100 A1 | 11/2007 | Barlow et al. |
| 2007/0255273 A1 | 11/2007 | Fernandez et al. |
| 2007/0255303 A1 | 11/2007 | Bakos et al. |
| 2007/0255306 A1 | 11/2007 | Conlon et al. |
| 2007/0260112 A1 | 11/2007 | Rahmani |
| 2007/0260117 A1 | 11/2007 | Zwolinski et al. |
| 2007/0260121 A1 | 11/2007 | Bakos et al. |
| 2007/0260242 A1 | 11/2007 | Dycus et al. |
| 2007/0260273 A1 | 11/2007 | Cropper et al. |
| 2007/0260302 A1 | 11/2007 | Igaki |
| 2007/0265494 A1 | 11/2007 | Leanna et al. |
| 2007/0270629 A1 | 11/2007 | Charles |
| 2007/0270889 A1 | 11/2007 | Conlon et al. |
| 2007/0270895 A1 | 11/2007 | Nobis et al. |
| 2007/0270907 A1 | 11/2007 | Stokes et al. |
| 2007/0282165 A1 | 12/2007 | Hopkins et al. |
| 2007/0282371 A1 | 12/2007 | Lee et al. |
| 2007/0293727 A1 | 12/2007 | Goldfarb et al. |
| 2007/0299387 A1 | 12/2007 | Williams et al. |
| 2008/0004650 A1 | 1/2008 | George |
| 2008/0015409 A1 | 1/2008 | Barlow et al. |
| 2008/0015413 A1 | 1/2008 | Barlow et al. |
| 2008/0015552 A1 | 1/2008 | Doyle et al. |
| 2008/0021416 A1 | 1/2008 | Arai et al. |
| 2008/0022927 A1 | 1/2008 | Zhang et al. |
| 2008/0027387 A1 | 1/2008 | Grabinsky |
| 2008/0033244 A1 | 2/2008 | Matsui et al. |
| 2008/0033451 A1 | 2/2008 | Rieber et al. |
| 2008/0051629 A1 | 2/2008 | Sugiyama et al. |
| 2008/0051735 A1 | 2/2008 | Measamer et al. |
| 2008/0058586 A1 | 3/2008 | Karpiel |
| 2008/0058854 A1 | 3/2008 | Kieturakis et al. |
| 2008/0065169 A1 | 3/2008 | Colliou et al. |
| 2008/0071264 A1 | 3/2008 | Azure |
| 2008/0086172 A1 | 4/2008 | Martin et al. |
| 2008/0091068 A1 | 4/2008 | Terliuc |
| 2008/0097159 A1 | 4/2008 | Ishiguro |
| 2008/0097472 A1 | 4/2008 | Agmon et al. |
| 2008/0097483 A1 | 4/2008 | Ortiz et al. |
| 2008/0103527 A1 | 5/2008 | Martin et al. |
| 2008/0114384 A1 | 5/2008 | Chang et al. |
| 2008/0119870 A1 | 5/2008 | Williams |
| 2008/0119891 A1 | 5/2008 | Miles et al. |
| 2008/0125774 A1 | 5/2008 | Palanker et al. |
| 2008/0125796 A1 | 5/2008 | Graham |
| 2008/0132892 A1 | 6/2008 | Lunsford et al. |
| 2008/0139882 A1 | 6/2008 | Fujimori |
| 2008/0140069 A1 | 6/2008 | Filloux et al. |
| 2008/0140071 A1 | 6/2008 | Vegesna |
| 2008/0147056 A1 | 6/2008 | van der Weide et al. |
| 2008/0150754 A1 | 6/2008 | Quendt |
| 2008/0171907 A1 | 7/2008 | Long et al. |
| 2008/0177135 A1 | 7/2008 | Muyari et al. |
| 2008/0188710 A1 | 8/2008 | Segawa et al. |
| 2008/0188868 A1 | 8/2008 | Weitzner et al. |
| 2008/0200755 A1 | 8/2008 | Bakos |
| 2008/0200762 A1 | 8/2008 | Stokes et al. |
| 2008/0200911 A1 | 8/2008 | Long |
| 2008/0200933 A1 | 8/2008 | Bakos et al. |
| 2008/0200934 A1 | 8/2008 | Fox |
| 2008/0208213 A1 | 8/2008 | Benjamin et al. |
| 2008/0208280 A1 | 8/2008 | Lindenthaler et al. |
| 2008/0221587 A1 | 9/2008 | Schwartz |
| 2008/0228213 A1 | 9/2008 | Blakeney et al. |
| 2008/0230972 A1 | 9/2008 | Ganley |
| 2008/0234696 A1 | 9/2008 | Taylor et al. |
| 2008/0243106 A1 | 10/2008 | Coe et al. |
| 2008/0243148 A1 | 10/2008 | Mikkaichi et al. |
| 2008/0243176 A1 | 10/2008 | Weitzner et al. |
| 2008/0249567 A1 | 10/2008 | Kaplan |
| 2008/0262513 A1 | 10/2008 | Stahler et al. |
| 2008/0262524 A1 | 10/2008 | Bangera et al. |
| 2008/0262540 A1 | 10/2008 | Bangera et al. |
| 2008/0275474 A1 | 11/2008 | Martin et al. |
| 2008/0275475 A1 | 11/2008 | Schwemberger et al. |
| 2008/0287737 A1 | 11/2008 | Dejima |
| 2008/0287801 A1 | 11/2008 | Magnin et al. |
| 2008/0287983 A1 | 11/2008 | Smith et al. |
| 2008/0300461 A1 | 12/2008 | Shaw et al. |
| 2008/0300547 A1 | 12/2008 | Bakos |
| 2008/0300571 A1 | 12/2008 | LePivert |
| 2008/0306493 A1 | 12/2008 | Shibata et al. |
| 2008/0309758 A1 | 12/2008 | Karasawa et al. |
| 2008/0312496 A1 | 12/2008 | Zwolinski |
| 2008/0312499 A1 | 12/2008 | Handa et al. |
| 2008/0312500 A1 | 12/2008 | Asada et al. |
| 2008/0312506 A1 | 12/2008 | Spivey et al. |
| 2008/0319436 A1 | 12/2008 | Daniel et al. |
| 2008/0319439 A1 | 12/2008 | Ootsubu |
| 2009/0005636 A1 | 1/2009 | Pang et al. |
| 2009/0030278 A1 | 1/2009 | Minakuchi |
| 2009/0054728 A1 | 2/2009 | Trusty |
| 2009/0062788 A1 | 3/2009 | Long et al. |
| 2009/0062795 A1 | 3/2009 | Vakharia et al. |
| 2009/0069634 A1 | 3/2009 | Larkin |
| 2009/0076499 A1 | 3/2009 | Azure |
| 2009/0078736 A1 | 3/2009 | Van Lue |
| 2009/0082627 A1 | 3/2009 | Karasawa et al. |
| 2009/0082776 A1 | 3/2009 | Cresina |
| 2009/0082779 A1 | 3/2009 | Nakao |
| 2009/0093690 A1 | 4/2009 | Yoshizawa |
| 2009/0112059 A1 | 4/2009 | Nobis |
| 2009/0112063 A1 | 4/2009 | Bakos et al. |
| 2009/0125042 A1 | 5/2009 | Mouw |
| 2009/0131751 A1 | 5/2009 | Spivey et al. |
| 2009/0143639 A1 | 6/2009 | Stark |
| 2009/0143649 A1 | 6/2009 | Rossi |
| 2009/0143794 A1 | 6/2009 | Conlon et al. |
| 2009/0143818 A1 | 6/2009 | Faller et al. |
| 2009/0149710 A1 | 6/2009 | Stefanchik et al. |
| 2009/0163770 A1 | 6/2009 | Torrie et al. |
| 2009/0177031 A1 | 7/2009 | Surti et al. |
| 2009/0177219 A1 | 7/2009 | Conlon |
| 2009/0182325 A1 | 7/2009 | Werneth et al. |
| 2009/0182332 A1 | 7/2009 | Long et al. |

(56) References Cited

U.S. PATENT DOCUMENTS

| | | |
|---|---|---|
| 2009/0192344 A1 | 7/2009 | Bakos et al. |
| 2009/0192534 A1 | 7/2009 | Ortiz et al. |
| 2009/0198212 A1 | 8/2009 | Timberlake et al. |
| 2009/0198231 A1 | 8/2009 | Esser et al. |
| 2009/0198253 A1 | 8/2009 | Omori |
| 2009/0209990 A1 | 8/2009 | Yates et al. |
| 2009/0210000 A1 | 8/2009 | Sullivan et al. |
| 2009/0216248 A1 | 8/2009 | Uenohara et al. |
| 2009/0221873 A1 | 9/2009 | McGrath |
| 2009/0227999 A1 | 9/2009 | Willis et al. |
| 2009/0228001 A1 | 9/2009 | Pacey |
| 2009/0248055 A1 | 10/2009 | Spivey et al. |
| 2009/0259105 A1 | 10/2009 | Miyano et al. |
| 2009/0269317 A1 | 10/2009 | Davalos |
| 2009/0281559 A1 | 11/2009 | Swain et al. |
| 2009/0287206 A1 | 11/2009 | Jun |
| 2009/0287236 A1 | 11/2009 | Bakos et al. |
| 2009/0292164 A1 | 11/2009 | Yamatani |
| 2009/0292167 A1 | 11/2009 | Kimoto |
| 2009/0306470 A1 | 12/2009 | Karasawa et al. |
| 2009/0322864 A1 | 12/2009 | Karasawa et al. |
| 2009/0326332 A1 | 12/2009 | Carter |
| 2010/0010294 A1 | 1/2010 | Conlon et al. |
| 2010/0010298 A1 | 1/2010 | Bakos et al. |
| 2010/0010303 A1 | 1/2010 | Bakos |
| 2010/0023032 A1 | 1/2010 | Granja Filho |
| 2010/0030211 A1 | 2/2010 | Davalos et al. |
| 2010/0036198 A1 | 2/2010 | Tacchino et al. |
| 2010/0042045 A1 | 2/2010 | Splvey |
| 2010/0048990 A1 | 2/2010 | Bakos |
| 2010/0049223 A1 | 2/2010 | Granja Filho |
| 2010/0056862 A1 | 3/2010 | Bakos |
| 2010/0056864 A1 | 3/2010 | Lee |
| 2010/0076451 A1 | 3/2010 | Zwolinski et al. |
| 2010/0076460 A1 | 3/2010 | Taylor et al. |
| 2010/0081875 A1 | 4/2010 | Fowler et al. |
| 2010/0091128 A1 | 4/2010 | Ogasawara et al. |
| 2010/0113872 A1 | 5/2010 | Asada et al. |
| 2010/0121362 A1 | 5/2010 | Clague et al. |
| 2010/0130817 A1 | 5/2010 | Conlon |
| 2010/0152539 A1 | 6/2010 | Ghabrial et al. |
| 2010/0152725 A1 | 6/2010 | Pearson et al. |
| 2010/0152746 A1 | 6/2010 | Ceniccola et al. |
| 2010/0191050 A1 | 7/2010 | Zwolinski |
| 2010/0191267 A1 | 7/2010 | Fox |
| 2010/0198149 A1 | 8/2010 | Fox |
| 2010/0198248 A1 | 8/2010 | Vakharia |
| 2010/0198254 A1 | 8/2010 | Schaeffer |
| 2010/0210906 A1 | 8/2010 | Wendlandt |
| 2010/0217367 A1 | 8/2010 | Belson |
| 2010/0249700 A1 | 9/2010 | Spivey |
| 2010/0256628 A1 | 10/2010 | Pearson et al. |
| 2010/0261994 A1 | 10/2010 | Davalos et al. |
| 2010/0268025 A1 | 10/2010 | Belson |
| 2010/0286791 A1 | 11/2010 | Goldsmith |
| 2010/0298642 A1 | 11/2010 | Trusty et al. |
| 2010/0312056 A1 | 12/2010 | Galperin et al. |
| 2010/0331622 A2 | 12/2010 | Conlon |
| 2010/0331758 A1 | 12/2010 | Davalos et al. |
| 2011/0077476 A1 | 3/2011 | Rofougaran |
| 2011/0087224 A1 | 4/2011 | Cadeddu et al. |
| 2011/0087266 A1 | 4/2011 | Conlon et al. |
| 2011/0087267 A1 | 4/2011 | Spivey et al. |
| 2011/0093009 A1 | 4/2011 | Fox |
| 2011/0098694 A1 | 4/2011 | Long |
| 2011/0098704 A1 | 4/2011 | Long et al. |
| 2011/0106221 A1 | 5/2011 | Neal, II et al. |
| 2011/0112434 A1 | 5/2011 | Ghabrial et al. |
| 2011/0112527 A1 | 5/2011 | Hamilton, Jr. et al. |
| 2011/0115891 A1 | 5/2011 | Trusty |
| 2011/0124964 A1 | 5/2011 | Nobis |
| 2011/0152610 A1 | 6/2011 | Trusty et al. |
| 2011/0152859 A1 | 6/2011 | Long et al. |
| 2011/0152878 A1 | 6/2011 | Trusty et al. |
| 2011/0152888 A1 | 6/2011 | Ho et al. |
| 2011/0152923 A1 | 6/2011 | Fox |
| 2011/0160514 A1 | 6/2011 | Long et al. |
| 2011/0190659 A1 | 8/2011 | Long et al. |
| 2011/0190764 A1 | 8/2011 | Long et al. |
| 2011/0193948 A1 | 8/2011 | Amling et al. |
| 2011/0224665 A1 | 9/2011 | Crosby et al. |
| 2011/0245619 A1 | 10/2011 | Holcomb |
| 2011/0282149 A1 | 11/2011 | Vargas et al. |
| 2011/0284014 A1 | 11/2011 | Cadeddu et al. |
| 2011/0285488 A1 | 11/2011 | Scott et al. |
| 2012/0004502 A1 | 1/2012 | Weitzner et al. |
| 2012/0029335 A1 | 2/2012 | Sudam et al. |
| 2012/0078266 A1 | 3/2012 | Tyson, Jr. |
| 2012/0088965 A1 | 4/2012 | Stokes et al. |
| 2012/0089089 A1 | 4/2012 | Swain et al. |
| 2012/0089093 A1 | 4/2012 | Trusty |
| 2012/0101331 A1 | 4/2012 | Gilad et al. |
| 2012/0101413 A1 | 4/2012 | Beetel et al. |
| 2012/0116155 A1 | 5/2012 | Trusty |
| 2012/0149981 A1 | 6/2012 | Khait et al. |
| 2012/0150172 A1 | 6/2012 | Ortiz et al. |
| 2012/0179148 A1 | 7/2012 | Conlon |
| 2012/0191075 A1 | 7/2012 | Trusty |
| 2012/0191076 A1 | 7/2012 | Voegele et al. |
| 2012/0220998 A1 | 8/2012 | Long et al. |
| 2012/0220999 A1 | 8/2012 | Long |
| 2012/0221002 A1 | 8/2012 | Long et al. |
| 2012/0238796 A1 | 9/2012 | Conlon |
| 2012/0289857 A1 | 11/2012 | Toth et al. |
| 2012/0330306 A1 | 12/2012 | Long et al. |
| 2013/0030430 A1 | 1/2013 | Stewart et al. |
| 2013/0090666 A1 | 4/2013 | Hess et al. |
| 2013/0138091 A1 | 5/2013 | Coe et al. |
| 2013/0158348 A1 | 6/2013 | Nobis et al. |
| 2013/0172672 A1 | 7/2013 | Iddan et al. |
| 2013/0217970 A1 | 8/2013 | Weisenburgh, II et al. |
| 2013/0231530 A1 | 9/2013 | Lien et al. |
| 2013/0245356 A1 | 9/2013 | Fernandez et al. |
| 2013/0331649 A1 | 12/2013 | Khait et al. |
| 2014/0012247 A1 | 1/2014 | Bakos et al. |
| 2014/0031813 A1 | 1/2014 | Tellio et al. |
| 2014/0039491 A1 | 2/2014 | Bakos et al. |
| 2014/0039492 A1 | 2/2014 | Long |
| 2014/0052126 A1 | 2/2014 | Long et al. |
| 2014/0052216 A1 | 2/2014 | Long et al. |
| 2014/0121678 A1 | 5/2014 | Trusty et al. |
| 2014/0243597 A1 | 8/2014 | Weisenburgh, II et al. |
| 2014/0343360 A1 | 11/2014 | Shohat et al. |
| 2015/0032132 A1 | 1/2015 | Harris et al. |
| 2015/0230858 A1 | 8/2015 | Long et al. |
| 2015/0265335 A1 | 9/2015 | Bakos et al. |
| 2015/0265342 A1 | 9/2015 | Long et al. |

FOREIGN PATENT DOCUMENTS

| | | |
|---|---|---|
| DE | 4323585 A1 | 1/1995 |
| DE | 19713797 A1 | 10/1997 |
| DE | 19757056 B4 | 8/2008 |
| DE | 102006027873 B4 | 10/2009 |
| EP | 0086338 A1 | 8/1983 |
| EP | 0286415 A2 | 10/1988 |
| EP | 0499491 A2 | 8/1992 |
| EP | 0589454 A2 | 3/1994 |
| EP | 0464479 B1 | 3/1995 |
| EP | 0529675 B1 | 2/1996 |
| EP | 0773003 A1 | 5/1997 |
| EP | 0621009 B1 | 7/1997 |
| EP | 0724863 B1 | 7/1999 |
| EP | 0760629 B1 | 11/1999 |
| EP | 0818974 B1 | 7/2001 |
| EP | 1281356 A2 | 2/2003 |
| EP | 0947166 B1 | 5/2003 |
| EP | 0836832 B1 | 12/2003 |
| EP | 1402837 A1 | 3/2004 |
| EP | 0744918 B1 | 4/2004 |
| EP | 0931515 B1 | 8/2004 |
| EP | 0941128 B1 | 10/2004 |
| EP | 1411843 B1 | 10/2004 |
| EP | 1150614 B1 | 11/2004 |

(56) References Cited

FOREIGN PATENT DOCUMENTS

| | | |
|---|---|---|
| EP | 1477104 A1 | 11/2004 |
| EP | 1481642 A1 | 12/2004 |
| EP | 1493391 A1 | 1/2005 |
| EP | 0848598 B1 | 2/2005 |
| EP | 1281360 B1 | 3/2005 |
| EP | 1568330 A1 | 8/2005 |
| EP | 1452143 B1 | 9/2005 |
| EP | 1616527 A2 | 1/2006 |
| EP | 1006888 B1 | 3/2006 |
| EP | 1629764 A1 | 3/2006 |
| EP | 1013229 B1 | 6/2006 |
| EP | 1721561 A1 | 11/2006 |
| EP | 1153578 B1 | 3/2007 |
| EP | 1334696 B1 | 3/2007 |
| EP | 1769766 A1 | 4/2007 |
| EP | 1836971 A2 | 9/2007 |
| EP | 1836980 A1 | 9/2007 |
| EP | 1854421 A2 | 11/2007 |
| EP | 1857061 A1 | 11/2007 |
| EP | 1875876 A1 | 1/2008 |
| EP | 1891881 A1 | 2/2008 |
| EP | 1902663 A1 | 3/2008 |
| EP | 1477106 B1 | 6/2008 |
| EP | 1949844 A1 | 7/2008 |
| EP | 1518499 B1 | 8/2008 |
| EP | 1582138 B1 | 9/2008 |
| EP | 1709918 B1 | 10/2008 |
| EP | 1985226 A2 | 10/2008 |
| EP | 1994904 A1 | 11/2008 |
| EP | 1707130 B1 | 12/2008 |
| EP | 0723462 B1 | 3/2009 |
| EP | 1769749 B1 | 11/2009 |
| EP | 2135545 A2 | 12/2009 |
| EP | 1493397 B1 | 9/2011 |
| EP | 2659847 A1 | 11/2013 |
| FR | 2731610 A1 | 9/1996 |
| GB | 330629 A | 6/1930 |
| GB | 2335860 A | 10/1999 |
| GB | 2403909 A | 1/2005 |
| GB | 2421190 A | 6/2006 |
| GB | 2443261 A | 4/2008 |
| JP | 56-46674 | 4/1981 |
| JP | 63309252 A | 12/1988 |
| JP | 4038960 A | 2/1992 |
| JP | H 06-269460 A | 9/1994 |
| JP | 8-29699 A | 2/1996 |
| JP | H 9-75365 | 3/1997 |
| JP | H 10-24049 A | 1/1998 |
| JP | 2000/107197 A | 4/2000 |
| JP | 2000245683 A | 9/2000 |
| JP | 2001-526072 A | 12/2001 |
| JP | 2002-369791 A | 12/2002 |
| JP | 2003-088494 A | 3/2003 |
| JP | 2003-235852 A | 8/2003 |
| JP | 2004-33525 A | 2/2004 |
| JP | 2004-065745 A | 3/2004 |
| JP | 2005-121947 A | 5/2005 |
| JP | 2005-261514 A | 9/2005 |
| JP | 2005-296063 A | 10/2005 |
| JP | 2006297005 A | 11/2006 |
| JP | 2006-343510 A | 12/2006 |
| JP | 2007-20806 A | 2/2007 |
| JP | 2007-125264 A | 5/2007 |
| JP | 2007-516792 A | 6/2007 |
| JP | 2010/503496 A | 2/2010 |
| NL | 1021295 C2 | 2/2004 |
| SU | 194230 | 5/1967 |
| SU | 980703 | 12/1982 |
| WO | WO 84/01707 A1 | 5/1984 |
| WO | WO 86/07543 A1 | 12/1986 |
| WO | WO 92/13494 A1 | 8/1992 |
| WO | WO 93/10850 A1 | 6/1993 |
| WO | WO 93/20760 A1 | 10/1993 |
| WO | WO 93/20765 A1 | 10/1993 |
| WO | WO 94/22383 A1 | 10/1994 |
| WO | WO 95/09666 A1 | 4/1995 |
| WO | WO 96/22056 A1 | 7/1996 |
| WO | WO 96/27331 A1 | 9/1996 |
| WO | WO 96/39946 A1 | 12/1996 |
| WO | WO 97/12557 A1 | 4/1997 |
| WO | WO 98/01080 A1 | 1/1998 |
| WO | WO 99/00060 A1 | 1/1999 |
| WO | WO 99/09919 A1 | 3/1999 |
| WO | WO 99/17661 A1 | 4/1999 |
| WO | WO 99/30622 A2 | 6/1999 |
| WO | WO 00/22996 A1 | 4/2000 |
| WO | WO 00/35358 A1 | 6/2000 |
| WO | WO 00/68665 A1 | 11/2000 |
| WO | WO 01/10319 A1 | 2/2001 |
| WO | WO 01/26708 A1 | 4/2001 |
| WO | WO 01/41627 A2 | 6/2001 |
| WO | WO 01/58360 A2 | 8/2001 |
| WO | WO 02/11621 A2 | 2/2002 |
| WO | WO 02/34122 A2 | 5/2002 |
| WO | WO 02/094082 A2 | 11/2002 |
| WO | WO 03/045260 A2 | 6/2003 |
| WO | WO 03/047684 A2 | 6/2003 |
| WO | WO 03/059412 A2 | 7/2003 |
| WO | WO 03/078721 A2 | 9/2003 |
| WO | WO 03/081761 A2 | 10/2003 |
| WO | WO 03/082129 A2 | 10/2003 |
| WO | WO 2004/006789 A1 | 1/2004 |
| WO | WO 2004/028613 A2 | 4/2004 |
| WO | WO 2004/037123 A1 | 5/2004 |
| WO | WO 2004/037149 A1 | 5/2004 |
| WO | WO 2004/052221 A1 | 6/2004 |
| WO | WO 2004/086984 A1 | 10/2004 |
| WO | WO 2005/009211 A2 | 2/2005 |
| WO | WO 2005/018467 A2 | 3/2005 |
| WO | WO 2005/037088 A2 | 4/2005 |
| WO | WO 2005/048827 A1 | 6/2005 |
| WO | WO 2005/065284 A2 | 7/2005 |
| WO | WO 2005/097019 A2 | 10/2005 |
| WO | WO 2005/097234 A2 | 10/2005 |
| WO | WO 2005/112810 A2 | 12/2005 |
| WO | WO 2005/120363 A1 | 12/2005 |
| WO | WO 2005/122866 A1 | 12/2005 |
| WO | WO 2006/007399 A1 | 1/2006 |
| WO | WO 2006/012630 A2 | 2/2006 |
| WO | WO 2006/040109 A1 | 4/2006 |
| WO | WO 2006/041881 A2 | 4/2006 |
| WO | WO 2006/060405 A2 | 6/2006 |
| WO | WO 2006/110733 A2 | 10/2006 |
| WO | WO 2006/113216 A2 | 10/2006 |
| WO | WO 2007/013059 A2 | 2/2007 |
| WO | WO 2007/014063 A2 | 2/2007 |
| WO | WO 2007/035537 A2 | 3/2007 |
| WO | WO 2007/048085 A2 | 4/2007 |
| WO | WO 2007/063550 A2 | 6/2007 |
| WO | WO 2007/100067 A1 | 9/2007 |
| WO | WO 2007/109171 A2 | 9/2007 |
| WO | WO 2007/135577 A2 | 11/2007 |
| WO | WO 2007/143200 A2 | 12/2007 |
| WO | WO 2007/144004 A1 | 12/2007 |
| WO | WO 2008/005433 A1 | 1/2008 |
| WO | WO 2008/033356 A2 | 3/2008 |
| WO | WO 2008/034103 A2 | 3/2008 |
| WO | WO 2008/041225 A2 | 4/2008 |
| WO | WO 2008/076337 A1 | 6/2008 |
| WO | WO 2008/076800 A2 | 6/2008 |
| WO | WO 2008/079440 A2 | 7/2008 |
| WO | WO 2008/080062 A1 | 7/2008 |
| WO | WO 2008/101075 A2 | 8/2008 |
| WO | WO 2008/101086 A2 | 8/2008 |
| WO | WO 2008/102154 A2 | 8/2008 |
| WO | WO 2008/108863 A2 | 9/2008 |
| WO | WO 2008/151237 A1 | 12/2008 |
| WO | WO 2009/021030 A1 | 2/2009 |
| WO | WO 2009/027065 A1 | 3/2009 |
| WO | WO 2009/029065 A1 | 3/2009 |
| WO | WO 2009/032623 A2 | 3/2009 |
| WO | WO 2009/036457 A1 | 3/2009 |
| WO | WO 2009/121017 A1 | 10/2009 |
| WO | WO 2010/027688 A1 | 3/2010 |

(56) References Cited

FOREIGN PATENT DOCUMENTS

| WO | WO 2010/056716 A2 | 5/2010 |
|---|---|---|
| WO | WO 2010/080974 A1 | 7/2010 |
| WO | WO 2010/088481 A1 | 8/2010 |
| WO | WO 2012/031204 A2 | 3/2012 |
| WO | WO 2012/071526 A2 | 5/2012 |
| WO | WO 2013/044378 A1 | 4/2013 |

OTHER PUBLICATIONS

Collins et al., "Local Gene Therapy of Solid Tumors with GM-CSF and B7-1 Eradicates Both Treated and Distal Tumors," Cancer Gene Therapy, vol. 13, pp. 1061-1071 (2006).
Partial International Search Report for PCT/US2008/053973, Oct. 16, 2008 (2 pages).
International Search Report for PCT/US2008/053973, Dec. 22, 2008 (9 pages).
International Search Report and Written Opinion for PCT/US2008/085771, Oct. 30, 2009 (14 pages).
International Preliminary Report on Patentability for PCT/US2008/053973, Aug. 19, 2009 (12 pages).
Written Opinion for PCT/US2008/053973, Dec. 22, 2008 (12 pages).
Michael S. Kavic, M.D., "Natural Orifice Translumenal Endoscopic Surgery: "NOTES"", JSLS, vol. 10, pp. 133-134 (2006).
Ethicon, Inc., "Wound Closure Manual: Chapter 3 (The Surgical Needle)," 15 pages, (1994).
Guido M. Sclabas, M.D., et al., "Endoluminal Methods for Gastrotomy Closure in Natural Orifice TransEnteric Surgery (NOTES)," Surgical Innovation, vol. 13, No. 1, pp. 23-30, Mar. 2006.
Fritscher-Ravens, et al., "Transgastric Gastropexy and Hiatal Hernia Repair for GERD Under EUS Control: a Porcine Model," Gastrointestinal Endoscopy, vol. 59, No. 1, pp. 89-95, 2004.
Ogando, "Prototype Tools That Go With the Flow," Design News, 2 pages, Jul. 17, 2006.
Kennedy, et al., "High-Burst-Strength, Feedback-Controlled Bipolar Vessel Sealing," Surgical Endoscopy, vol. 12, pp. 876-878 (1998).
K. Sumiyama et al., "Transesophageal Mediastinoscopy by Submucosal Endoscopy With Mucosal Flap Safety Value Technique," Gastrointest Endosc., Apr. 2007, vol. 65(4), pp. 679-683 (Abstract).
K. Sumiyama et al., "Submucosal Endoscopy with Mucosal Flap Safety Valve," Gastrointest Endosc. Apr. 2007, vol. 65(4) pp. 694-695 (Abstract).
K. Sumiyama et al., "Transgastric Cholecystectomy: Transgastric Accessibility to the Gallbladder Improved with the SEMF Method and a Novel Multibending Therapeutic Endoscope," Gastrointest Endosc., Jun. 2007, vol. 65(7), pp. 1028-1034 (Abstract).
K. Sumiyama et al., "Endoscopic Caps," Tech. Gastrointest. Endosc., vol. 8, pp. 28-32, 2006.
"Z-Offset Technique Used in the Introduction of Trocar During Laparoscopic Surgery," M.S. Hershey NOTES Presentation to EES NOTES Development Team, Sep. 27, 2007.
F.N. Denans, Nouveau Procede Pour La Guerison Des Plaies Des Intestines. Extrait Des Seances De La Societe Royale De Medecine De Marseille, Pendant Le Mois De Dec. 1825, et le Premier Tremestre De 1826, Séance Du 24 Fevrier 1826. Recueil De La Societe Royale De Medecin De Marseille. Marseille: Impr. D'Achard, 1826; 1:127-31. (with English translation).
I. Fraser, "An Historical Perspective on Mechanical Aids in Intestinal Anastamosis," Surg. Gynecol. Obstet. (Oct. 1982), vol. 155, pp. 566-574.
M.E. Ryan et al., "Endoscopic Intervention for Biliary Leaks After Laparoscopic Cholecystectomy: A Multicenter Review," Gastrointest. Endosc., vol. 47(3), 1998, pp. 261-266.
C. Cope, "Creation of Compression Gastroenterostomy by Means of the Oral, Percutaneous, or Surgical Introduction of Magnets: Feasibility Study in Swine," J. Vasc Interv Radio!, (1995), vol. 6(4), pp. 539-545.

J.W. Hazey et al., "Natural Orifice Transgastric Endoscopic Peritoneoscopy in Humans: Initial Clinical Trial," Surg Endosc, (Jan. 2008), vol. 22(1), pp. 16-20.
N. Chopita et al., "Endoscopic Gastroenteric Anastamosis Using Magnets," Endoscopy, (2005), vol. 37(4), pp. 313-317.
C. Cope et al., "Long Term Patency of Experimental Magnetic Compression Gastroenteric Anastomoses Achieved with Covered Stents," Gastrointest Endosc, (2001), vol. 53, pp. 780-784.
H. Okajima et al., "Magnet Compression Anastamosis for Bile Duct Stenosis After Duct to Duct Biliary Reconstruction in Living Donor Liver Transplantation," Liver Transplantation (2005), pp. 473-475.
A. Fritscher-Ravens et al., "Transluminal Endosurgery: Single Lumen Access Anastamotic Device for Flexible Endoscopy," Gastrointestinal Endosc, (2003), vol. 58(4), pp. 585-591.
G.A. Hallenbeck, M.D. et al., "An Instrument for Colorectal Anastomosis Without Sutrues," Dis Col Rectum, (1963), vol. 5, pp. 98-101.
T. Hardy, Jr., M.D. et al., "A Biofragmentable Ring for Sutureless Bowel Anastomosis. An Experimental Study," Dis Col Rectum, (1985), vol. 28, pp. 484-490.
P. O'Neill, M.D. et al., "Nonsuture Intestinal Anastomosis," Am J. Surg, (1962), vol. 104, pp. 761-767.
C.P. Swain, M.D. et al., "Anastomosis at Flexible Endoscopy: An Experimental Study of Compression Button Gastrojejunostomy," Gastrointest Endosc, (1991), vol. 37, pp. 628-632.
J.B. Murphy, M.D., "Cholecysto-Intestinal, Gastro-Intestinal, Entero-Intestinal Anastomosis, and Approximation Without Sutures (original research)," Med Rec, (Dec. 10, 1892), vol. 42(24), pp. 665-676.
USGI® EndoSurgical Operating System—g-Prox® Tissue Grasper/Approximation Device; [online] URL: http://www.usgimedical.com/eos/components-gprox.htm—accessed May 30, 2008 (2 pages).
Printout of web page—http://www.vacumed.com/zcom/product/Product.do?compid=27&prodid=852, #51XX Low-Cost Permanent Tubes 2MM ID, Smooth Interior Walls, VacuMed, Ventura, California, Accessed Jul. 24, 2007.
Endoscopic Retrograde Cholangiopancreatogram (ERCP); [online] URL: http://www.webmd.com/digestive-disorders/endoscopic-retrograde-cholangiopancreatogram-ercp.htm; last updated: Apr. 30, 2007; accessed: Feb. 21, 2008 (6 pages).
ERCP; Jackson Siegelbaum Gastroenterology; [online] URL: http://www.gicare.com/pated/epdgs20.htm; accessed Feb. 21, 2008 (3 pages).
D.G. Fong et al., "Transcolonic Ventral Wall Hernia Mesh Fixation in a Porcine Model," Endoscopy 2007; 39: 865-869.
B. Rubinsky, Ph.D., "Irreversible Electroporation in Medicine," Technology in Cancer Research and Treatment, vol. 6, No. 4, Aug. 2007, pp. 255-259.
D.B. Nelson, MD et al., "Endoscopic Hemostatic Devices," Gastrointestinal Endoscopy, vol. 54, No. 6, 2001, pp. 833-840.
CRE™ Pulmonary Balloon Dilator; [online] URL: http://www.bostonscientific.com/Device.bsci?page=HCP_Overview&navRe1Id=1000.1003&method=D . . . , accessed Jul. 18, 2008 (4 pages).
J.D. Paulson, M.D., et al., "Development of Flexible Culdoscopy," The Journal of the American Association of Gynecologic Laparoscopists, Nov. 1999, vol. 6, No. 4, pp. 487-490.
H. Seifert, et al., "Retroperitoneal Endoscopic Debridement for Infected Peripancreatic Necrosis," The Lancet, Research Letters, vol. 356, Aug. 19, 2000, pp. 653-655.
K.E. Mönkemüller, M.D., et al., "Transmural Drainage of Pancreatic Fluid Collections Without Electrocautery Using the Seldinger Technique," Gastrointestinal Endoscopy, vol. 48, No. 2, 1998, pp. 195-200, (Received Oct. 3, 1997; Accepted Mar. 31, 1998).
D. Wilhelm et al., "An Innovative, Safe and Sterile Sigmoid Access (ISSA) for NOTES," Endoscopy 2007, vol. 39, pp. 401-406.
Nakazawa et al., "Radiofrequency Ablation of Hepatocellular Carcinoma: Correlation Between Local Tumor Progression After Ablation and Ablative Margin," AJR, 188, pp. 480-488 (Feb. 2007).
Miklavčič et al., "A validated model of in vivo electric field distribution in tissues for electrochemotherapy and for DNA electrotransfer for gene therapy," Biochimica et Biophysica Acta, 1523, pp. 73-83 (2000).

(56) References Cited

OTHER PUBLICATIONS

Evans, "Ablative and cathether-delivered therapies for colorectal liver metastases (CRLM)," EJSO, 33, pp. S64-S75 (2007).
Wong et al., "Combined Percutaneous Radiofrequency Ablation and Ethanol Injection for Hepatocellular Carcinoma in High-Risk Locations," AJR, 190, pp. W187-W195 (2008).
Heller et al., "Electrically mediated plasmid DNA delivery to hepatocellular carcinomas in vivo," Gene Therapy, 7, pp. 826-829 (2000).
Widera et al., "Increased DNA Vaccine Delivery and Immunogenicity by Electroporation In Vivo," The Journal of Immunology, 164, pp. 4635-4640 (2000).
Weaver et al., "Theory of electroporation: A review," Bioelectrochemistry and Bioenergetics, 41, pp. 135-160 (1996).
Mulier et al., "Radiofrequency Ablation Versus Resection for Resectable Colorectal Liver Metastases: Time for a Randomized Trial?" Annals of Surgical Oncology, 15(1), pp. 144-157 (2008).
Link et al., "Regional Chemotherapy of Nonresectable Colorectal Liver Metastases with Mitoxanthrone, 5-Fluorouracil, Folinic Acid, and Mitomycin C May Prolong Survival," Cancer, 92, pp. 2746-2753 (2001).
Guyton et al., "Membrane Potentials and Action Potentials," W.B. Sanders, ed. Textbook of Medical Physiology, p. 56 (2000).
Guyton et al., "Contraction of Skeletal Muscle," Textbook of Medical Physiology, pp. 82-84 (2000).
"Ethicon Endo-Surgery Novel Investigational Notes and SSL Devices Featured in 15 Presentations at Sages," Apr. 22, 2009 Press Release; URL http://www.jnj.com/connect/news/all/20090422_152000; accessed Aug. 28, 2009 (3 pages).
"Ethicon Endo-Surgery Studies Presented At DDW Demonstrate Potential of Pure NOTES Surgery With Company's Toolbox," Jun. 3, 2009 Press Release; URL http://www.jnj.com/connect/news/product/20090603_120000; accessed Aug. 28, 2009 (3 pages).
Castellvi et al., "Hybrid Transvaginal NOTES Sleeve Gastrectomy in a Porcine Model Using a Magnetically Anchored Camera and Novel Instrumentation," Abstract submitted along with Poster at Sages Annual Meeting in Phoenix, AZ, Apr. 22, 2009 (1 page).
Castellvi et al., "Hybrid Transvaginal NOTES Sleeve Gastrectomy in a Porcine Model Using a Magnetically Anchored Camera and Novel Instrumentation," Poster submitted along with Abstract at Sages Annual Meeting in Phoenix, AZ, Apr. 22, 2009 (1 page).
OCTO Port Modular Laparoscopy System for Single Incision Access, Jan. 4, 2010; URL http://www.medgadget.com/archives/2010/01/octo_port_modular_laparo . . . ; accessed Jan. 5, 2010 (4 pages).
Hakko Retractors, obtained Aug. 25, 2009 (5 pages).
Zadno et al., "Linear Superelasticity in Cold-Worked NI-TI," Engineering Aspects of Shape Memory Alloys, pp. 414-419 (1990).
How Stuff Works "How Smart Structures Will Work," http://science.howstuffworks.com/engineering/structural/smart-structure1.htm; accessed online Nov. 1, 2011 (3 pages).
Instant Armor: Science Videos—Science News—ScienCentral; http://www.sciencentral.com/articles./view.php3?article_id=218392121; accessed online Nov. 1, 2011 (2 pages).
Stanway, Smart Fluids: Current and Future Developments. Material Science and Technology, 20, pp. 931-939, 2004; accessed online Nov. 1, 2011 at http://www.dynamics.group.shef.ac.uk/smart/smart.html (7 pages).
Jolly et al., Properties and Applications of Commercial Magnetorheological Fluids. SPIE 5th Annual Int. Symposium on Smart Structures and Materials, 1998 (18 pages).
Rutala et al. "Guideline for Disinfection and Sterilization in Healthcare Facilities, 2008" (available at http://www.cdc.gov/hicpac/Disinfection_Sterilization/13_11sterilizingPractices.html).
Bewlay et al., "Spinning" in ASM Handbook, vol. 14B, Metalworking: Sheet Forming (2006).
Schoenbach et al. "Bacterial Decontamination of Liquids with Pulsed Electric Fields" IEEE Transactions on Dielectrics and Electrical Insulation. vol. 7 No. 5. Oct. 2000, pp. 637-645.
Davalos, et al., "Tissue Ablation with Irreversible Electroporation," Annals of Biomedical Engineering, 33.2 (2005): 223-231.

\* cited by examiner

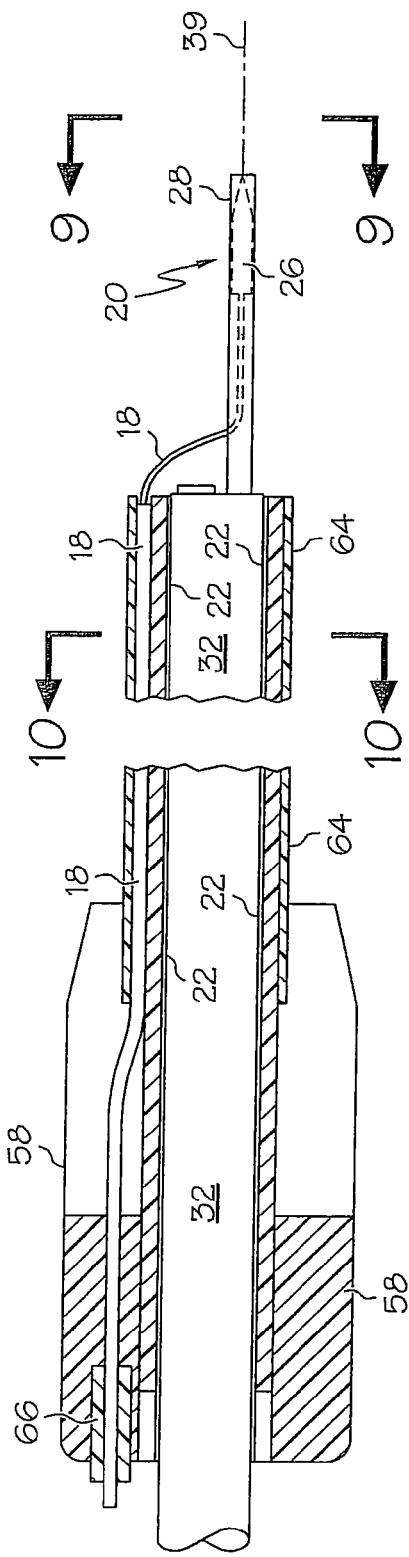
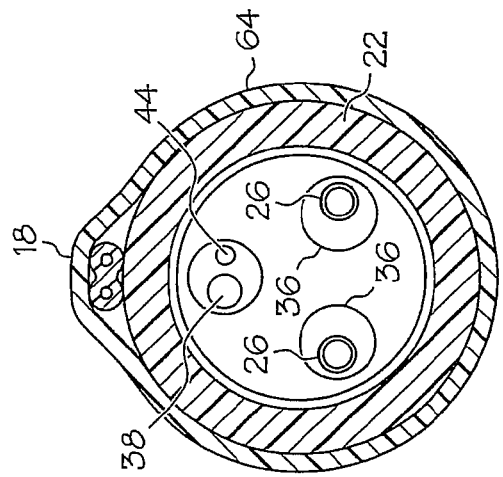
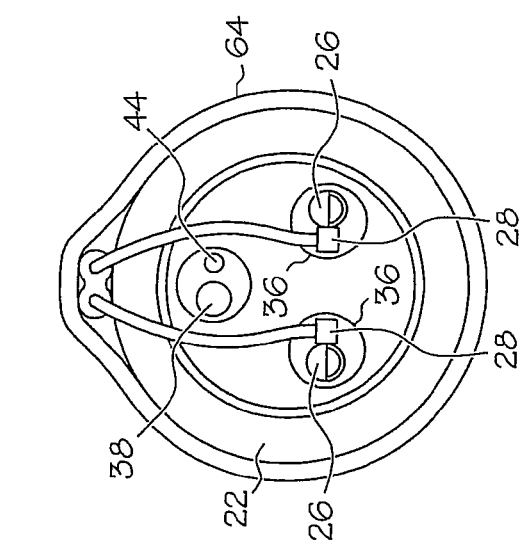
FIG. 8
FIG. 10
FIG. 9

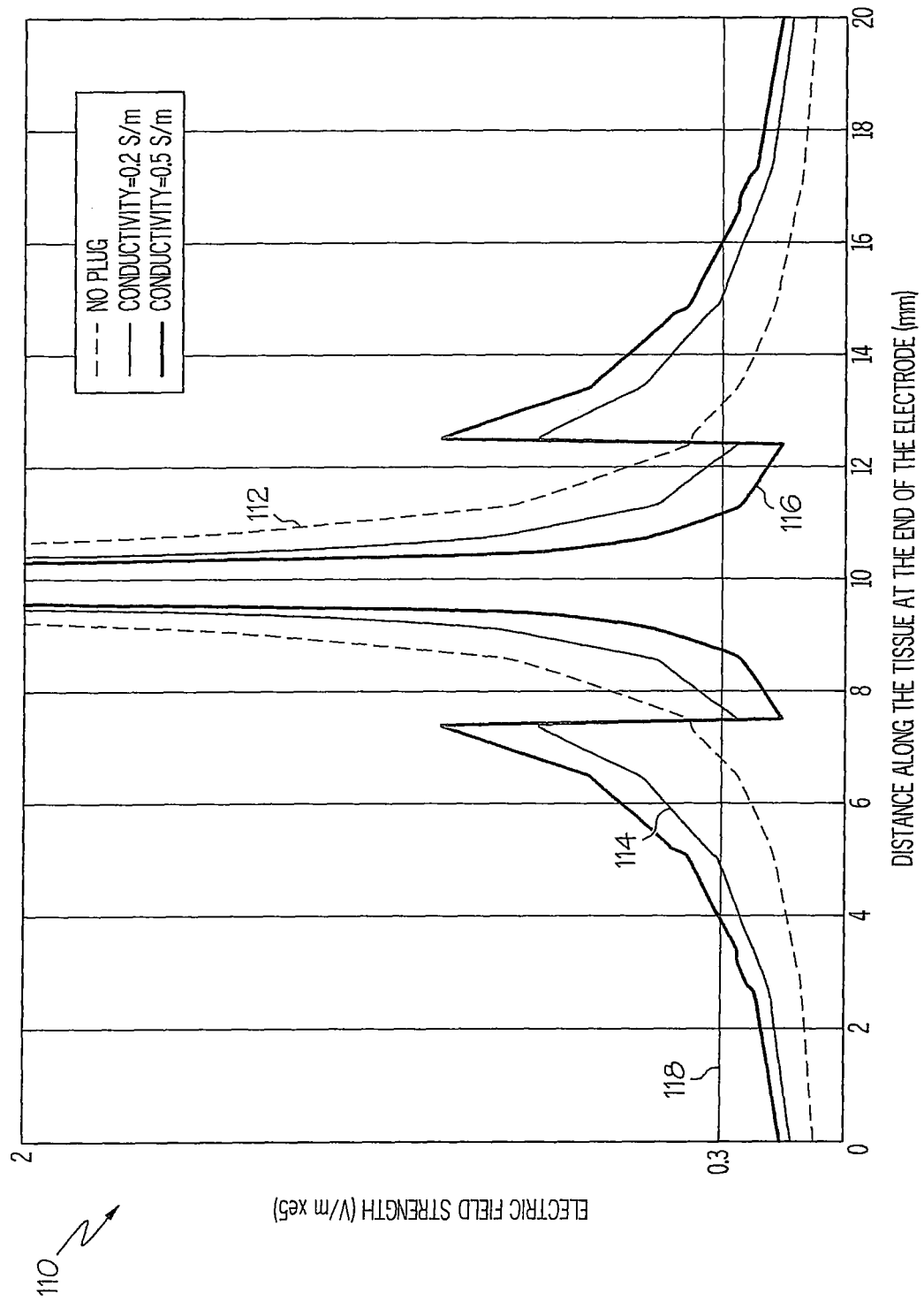

ELECTROPORATION ABLATION APPARATUS, SYSTEM, AND METHOD

CROSS REFERENCE TO RELATED APPLICATIONS

This application is a continuation application of U.S. patent application Ser. No. 12/694,452, filed Jan. 27, 2010, entitled ELECTROPORATION ABLATION APPARATUS, SYSTEM AND METHOD, now U.S. Patent Application Publication No. 2010/0130975, which issued as U.S. Pat. No. 8,449,538 on May 28, 2013, which is a divisional application, under 35 U.S.C. §121, of U.S. patent application Ser. No. 11/706,766, filed Feb. 15, 2007, entitled ELECTROPORATION ABLATION APPARATUS, SYSTEM, AND METHOD, now U.S. Pat. No. 7,655,004, which is related to U.S. patent application Ser. No. 12/635,298, filed Dec. 10, 2009, entitled ELECTROPORATION ABLATION APPARATUS, SYSTEM, AND METHOD, now U.S. Pat. No. 8,029,504, and U.S. patent application Ser. No. 11/706,591, filed Feb. 15, 2007, entitled ELECTRICAL ABLATION APPARATUS, SYSTEM, AND METHOD, now U.S. Patent Application Publication No. 2008/0200911, each of which is incorporated herein by reference in its entirety.

BACKGROUND

Electrical therapy techniques have been employed in medicine to treat pain and other and other conditions. Electrical ablation techniques have been employed in medicine for the removal of diseased tissue or abnormal growths from the body. Nevertheless, there is a need for improved medical instruments to electrically ablate or destroy diseased tissue or abnormal growths from the body, such as cancer tissue. There may be a need for such electrical therapy techniques to be performed endoscopically.

Electrical therapy probes comprising electrodes may be required to electrically treat diseased tissue. The electrodes may be introduced into the patient endoscopically to the tissue treatment region by passing the electrodes through the working channel of an endoscope.

SUMMARY

In one another general aspect, the various embodiments are directed to an apparatus. In at least one embodiment, the apparatus comprises a first channel and a second channel; a first probe positioned at least partially within the first channel, wherein the first probe comprises a first distal portion and defines a first longitudinal axis; and a first rotatable electrode coupled to the first distal portion of the first probe and laterally offset from the first longitudinal axis, wherein the first rotatable electrode is structured to rotate about the first longitudinal axis. The apparatus further comprises a second probe positioned at least partially within the second channel, wherein the second probe comprises a second distal portion and defines a second longitudinal axis; and a second rotatable electrode coupled to the second distal portion of the second probe and laterally offset from the second longitudinal axis, wherein the second rotatable electrode is structured to rotate about the second longitudinal axis, and wherein the first and second rotatable electrodes are configured to couple to an electrical waveform generator and to receive an irreversible electroporation electrical waveform. The apparatus further comprises an adjustable ablation region defined between the first and second rotatable electrodes, wherein the ablation region is adjustable by rotating at least one of the first and second electrodes.

In yet another general aspect, the various embodiments are directed to a system. In at least one embodiment, the system comprises a first channel and a second channel; a first probe positioned at least partially within the first channel, wherein the first probe comprises a first distal portion and defines a first longitudinal axis; and a first rotatable electrode extending from the first distal portion of the first probe and laterally offset from the first longitudinal axis, wherein the first rotatable electrode is structured to rotate about the first longitudinal axis. The system further comprises a second probe positioned at least partially within the second channel, wherein the second probe comprises a second distal portion and defines a second longitudinal axis; and a second rotatable electrode extending from the second distal portion of the second probe and laterally offset from the second longitudinal axis, wherein the second rotatable electrode is structured to rotate about the second longitudinal axis, and wherein the first and second rotatable electrodes are coupled to an electrical waveform generator and structured to receive an irreversible electroporation electrical waveform. The system further comprises an adjustable ablation region defined between the first and second rotatable electrodes, wherein the ablation region is adjustable by rotating at least one of the first and second electrodes.

In another general aspect, the various embodiments are directed to a method. In at least one embodiment, the method comprises positioning an elongate member comprising first and second channels within a body cavity, wherein a first and a second probe are disposed within the respective first and second channels, wherein the first and second probes each define a central axis, wherein a first and second electrode are coupled to the distal ends of the respective first and second probes, and wherein the first and second electrode are laterally offset from the central axes of the respective first and second probes. The method further comprises rotating at least one of the first and second probes about the central axis of the respective at least one first and second probes to adjust an ablation region positioned between the first and second electrodes.

FIGURES

The novel features of the various embodiments of the invention are set forth with particularity in the appended claims. The various embodiments of the invention, however, both as to organization and methods of operation, together with further objects and advantages thereof, may best be understood by reference to the following description, taken in conjunction with the accompanying drawings as follows.

FIG. 8 is a sectional view taken along the longitudinal axis of one embodiment of an endoscopic ablation system shown in FIG. 1.

FIG. 9 is an end view taken along line 9-9 of one embodiment of a therapeutic/diagnostic probe of the endoscopic ablation system shown in FIG. 8.

FIG. 10 is a sectional view taken along line 10-10 of a rotation tube of the endoscopic ablation system shown in FIG. 8.

FIG. 15 is a close up of the graph shown in FIG. 14.

DESCRIPTION

Figure 1:
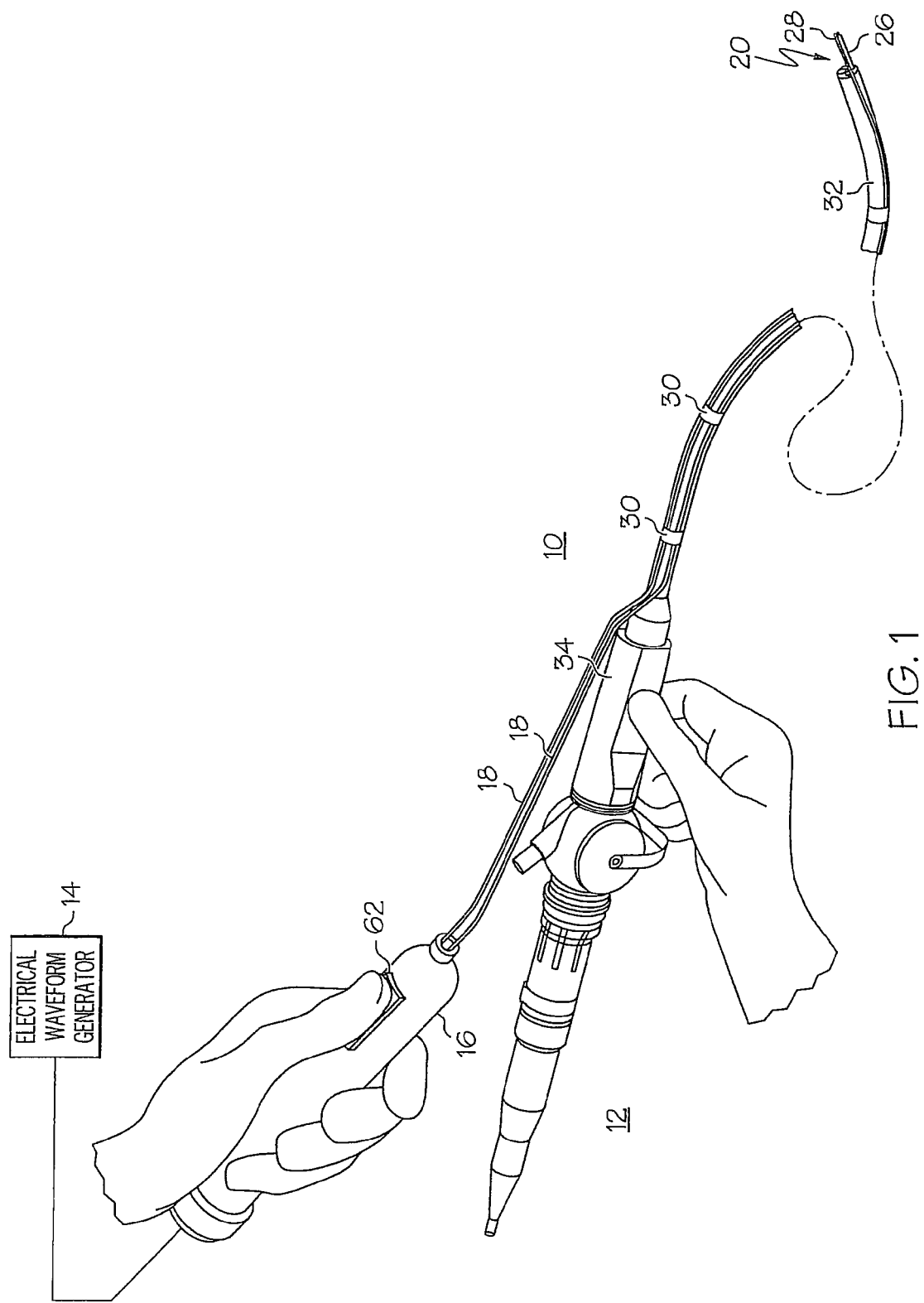
FIG. 1 illustrates one embodiment of an endoscopic ablation system.

The various embodiments described herein are directed to diagnostic and electrical therapy ablation devices. The diagnostic devices comprise biopsy probes. The electrical therapy ablation devices comprise probes and electrodes that can be positioned in a tissue treatment region of a patient endoscopically. An endoscopic electrode is inserted through a working channel of an endoscope. The placement and location of the electrodes can be important for effective and efficient therapy. Once positioned, the electrical therapy electrodes deliver electrical current to the treatment region. The electrical current is generated by a control unit or generator external to the patient and typically has particular waveform characteristics, such as frequency, amplitude, and pulse width. Depending on the diagnostic or therapeutic treatment rendered, the probes may comprise one electrode containing both a cathode and an anode or may contain a plurality of electrodes with at least one serving as a cathode and at least one serving as an anode.

Electrical therapy ablation may employ electroporation, or electropermeabilization, techniques where an externally applied electrical field significantly increases the electrical conductivity and permeability of a cell plasma membrane. Electroporation is the generation of a destabilizing electric potential across biological membranes. In electroporation, pores are formed when the voltage across the cell plasma membrane exceeds its dielectric strength. Electroporation destabilizing electric potentials are generally in the range of several hundred volts across a distance of several millimeters. Below certain magnitude thresholds, the electric potentials may be applied across a biological membrane as a way of introducing some substance into a cell, such as loading it with a molecular probe, a drug that can change the function of the cell, a piece of coding DNA, or increase the uptake of drugs in cells. If the strength of the applied electrical field and/or duration of exposure to it are properly chosen, the pores formed by the electrical pulse reseal after a short period of time, during which extra-cellular compounds have a chance to enter into the cell. Thus, below a certain threshold, the process is reversible and the potential does not permanently damage the cell membrane. This process may be referred to as reversible electroporation (RE).

On the other hand, the excessive exposure of live cells to large electrical fields (or potentials) can cause apoptosis and/or necrosis—the processes that result in cell death. Accordingly, this may be referred to irreversible electroporation (IRE) because the cells die when exposed to excessive electrical potentials across the cell membranes. The various embodiments described herein are directed to electrical therapy ablation devices such as electroporation ablation devices. In one embodiment, the electroporation ablation device may be an IRE device to destroy cells by applying an electric potential to the cell membrane. The IRE potentials may be applied to cell membranes of diseased tissue in order to kill the diseased cells. The IRE may be applied in the form of direct current (DC) electrical waveforms having a characteristic frequency, amplitude, and pulse width.

Electroporation may be performed with devices called electroporators, appliances which create the electric current and send it through the cell. The electroporators may comprise two or more metallic (e.g., Ag, AgCl) electrodes connected to an energy source to generate an electric field having a suitable characteristic waveform output in terms of frequency, amplitude, and pulse width.

Endoscopy means looking inside and refers to looking inside the human body for medical reasons. Endoscopy may be performed using an instrument called an endoscope. Endoscopy is a minimally invasive diagnostic medical procedure used to evaluate the interior surfaces of an organ by inserting a small tube into the body, often, but not necessarily, through a natural body opening. Through the endoscope, the operator is able to see abnormal or diseased tissue such as lesions and other surface conditions. The endoscope may have a rigid or a flexible tube or member and in addition to providing an image for visual inspection and photography, the endoscope enables taking biopsies, retrieving foreign objects, and introducing medical instruments to a tissue treatment region. Endoscopy is the vehicle for minimally invasive surgery.

The embodiments of the electrical therapy ablation devices may be employed for treating diseased tissue, tissue masses, tissue tumors, and lesions (diseased tissue). More particularly, the electrical therapy ablation devices may be employed in minimally invasive therapeutic treatment of diseased tissue. The electrical therapy ablation devices may be employed to deliver energy to the diseased tissue to ablate or destroy tumors, masses, legions, and other abnormal tissue growths. In one embodiment, the electrical therapy ablation devices and techniques described herein may be employed in the treatment of cancer by quickly creating necrosis of live tissue and destroying cancerous tissue in-vivo. These minimally invasive therapeutic treatment of diseased tissue where medical instruments are introduced to a tissue treatment region within the body of a patient through a natural opening are known as Natural Orifice Translumenal Endoscopic Surgery (NOTES)™.

A biopsy is a medical procedure involving the removal of cells or tissues for examination. The tissue is often examined under a microscope and can also be analyzed chemically (for example, using polymerase chain reaction [PCR] techniques). When only a sample of tissue is removed, the procedure is called an incisional biopsy or core biopsy. When an entire lump or suspicious area is removed, the procedure is called an excisional biopsy. When a sample of tissue or fluid is removed with a needle, the procedure is called a needle aspiration biopsy. A procedure called "optical biopsy" may be employed where optical coherence tomography may be adapted to allow high-speed visualization of tissue in a living animal with a catheter-endoscope 1 millimeter in diameter. Optical biopsy may be used to obtain cross-sectional images of internal tissues.

Biopsy specimens may be taken from part of a lesion when the cause of a disease is uncertain or its extent or exact character is in doubt. Vasculitis, for instance, is usually diagnosed on biopsy. Additionally, pathologic examination of a biopsy can determine whether a lesion is benign or malignant, and can help differentiate between different types of cancer.

FIG. 1 illustrates one embodiment of an endoscopic ablation system 10. The endoscopic ablation system 10 may be employed to electrically treat diseased tissue such as tumors and lesions. The endoscopic ablation system 10 may be configured to be positioned within a natural opening of a patient such as the colon or the esophagus and can be passed through the opening to a tissue treatment region. The illustrated endoscopic ablation system 10 may be used to treat diseased tissue via the colon or the esophagus of the patient, for example. The tissue treatment region may be located in the esophagus, colon, liver, breast, brain, and lung, among others. The endoscopic ablation system 10 can be configured to treat a number of lesions and ostepathologies including but not limited to metastatic lesions, tumors, fractures, infected site, inflamed sites, and the like. Once positioned at the target tissue treatment region, the endoscopic ablation system 10 can be configured to treat and ablate diseased tissue in that region. In one embodiment, the endoscopic ablation system 10 may be employed as a diagnostic instrument to collect a tissue sample using a biopsy device introduced into the tissue treatment region via an endoscope (e.g., the endoscopic ablation system 10). In one embodiment, the endoscopic ablation system 10 may be adapted to treat diseased tissue, such as cancers, of the gastrointestinal (GI) tract or esophagus that may be accessed orally. In another embodiment, the endoscopic ablation system 10 may be adapted to treat diseased tissue, such as cancers, of the liver or other organs that may be accessible transanally through the colon and/or the abdomen.

Figure 2:
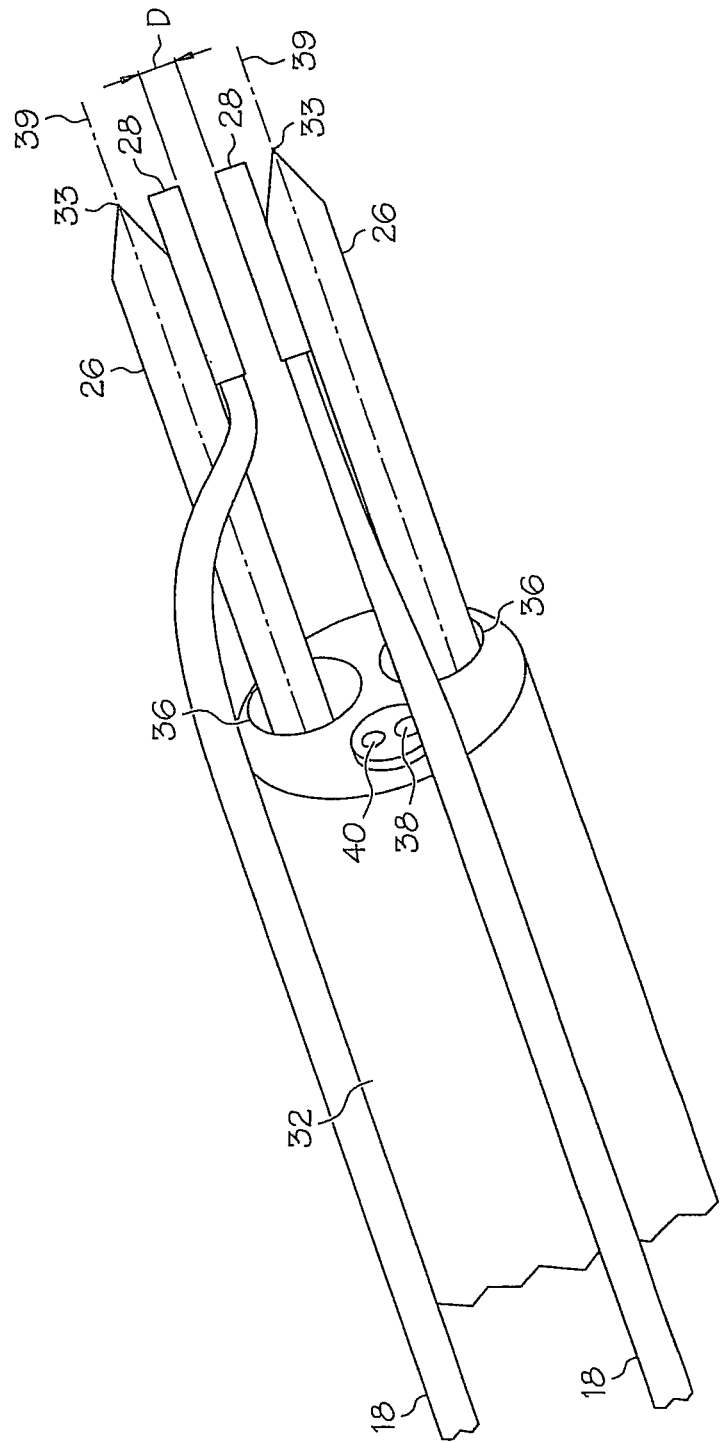
FIG. 2 is an enlarged view of one embodiment of a therapeutic/diagnostic probe of one embodiment of the endoscopic ablation system shown in FIG. 1.

One embodiment of the endoscopic ablation system 10 may be mounted on a flexible endoscope 12 (also referred to as endoscope 12), such as the GIF-100 model available from Olympus Corporation. The flexible endoscope 12 includes an endoscope handle 34 and a flexible shaft 32. The endoscopic ablation system 10 generally comprises one or more therapeutic/diagnostic probe 20, a plurality of conductors 18, a handpiece 16 having a switch 62, and an electrical waveform generator 14. In one embodiment, the electrical waveform generator 14 may be a high voltage direct current (DC) irreversible electroporation (IRE) generator. The therapeutic/diagnostic probe 20 is located at a distal end of the flexible shaft 32 and the conductors 18 attach to the flexible shaft 32 using a plurality of clips 30. The therapeutic/diagnostic probe 20 comprises an elongate member attached to an electrical energy delivery device comprising one or more electrical therapy electrodes 28. In one embodiment, the therapeutic/diagnostic probe 20 extends through a bore in the flexible shaft 32 such as a working channel 36 (FIG. 2). In one embodiment, the therapeutic/diagnostic probe 20 may comprise elongate diagnostic probes 26 attached or joined to the electrodes 28 that extend through the working channel 36. In another embodiment, the flexible shaft 32 may comprise two working channels 36 and a first diagnostic probe 26 joined to a first electrode 28 that extends through the distal end of a first working channels 36 and a second diagnostic probe 26 joined to a second electrode 28 that extends through the distal end of a second working channel 36. In one embodiment, the diagnostic probe comprises one or more diagnostic probes 26 attached or joined in any suitable manner to the electrodes 28. For example, the diagnostic probes 26 may be joined or attached to the electrodes 28 by welding, soldering, brazing or other well known techniques. Many different energy sources may be used for welding, soldering, or brazing such as, for example, a gas flame, an electric arc, a laser, an electron beam, friction, and ultrasound. Thus, in one embodiment, the therapeutic/diagnostic probe 20 may be employed in a diagnostic mode to take a biopsy sample of the diseased tissue using the diagnostic probes 26 and, in one embodiment the therapeutic/diagnostic probe 20 may be employed in a therapeutic mode by treating diseased tissue with electrical current delivered by the electrodes 28. In other embodiments, the therapeutic/diagnostic probe 20 may be employed in a combination of therapeutic and diagnostic modes. The therapeutic/diagnostic probe 20 may be passed though the one or more working channels 36 located within the flexible shaft 32. The therapeutic/diagnostic probe 20 is delivered to the tissue treatment region endoscopically and is located on top of the diseased tissue to be electrically treated. Once the therapeutic/diagnostic probe 20 is suitably located by the operator, manual operation of the switch 62 on the handpiece 16 electrically connects or disconnects the electrodes 28 to the electrical waveform generator 14. Alternatively, the switch 62 may be mounted on, for example, a foot switch (not shown).

In one embodiment, the electrical waveform generator 14 may be a conventional, bipolar/monopolar electrosurgical generator (ICC200 Erbe Inc.) or an IRE generator such as one of many models commercially available, including Model Number ECM800, available from BTX Boston, Mass. The IRE generator generates electrical waveforms having predetermined frequency, amplitude, and pulse width. The application of these electrical waveforms to the cell membrane causes the cell to die. The IRE electrical waveforms are applied to the cell membranes of diseased tissue in order to kill the diseased cells and ablate the diseased tissue. IRE electrical waveforms suitable to destroy the cells of diseased tissues energy are generally in the form of direct current (DC) electrical pulses delivered at a frequency in the range of 1-20 Hz, amplitude in the range of 100-1000 VDC, and pulse width in the range of 0.01-100 ms. For example, an electrical waveform having amplitude of 500 VDC and pulse duration of 20 ms may be delivered at a pulse repetition rate or frequency of 10 HZ can destroy a reasonably large volume of diseased tissue. Unlike RF ablation systems which require high power and energy input into the tissue to heat and destroy the tissue, IRE requires very little energy input into the tissue, rather the destruction of the tissue is caused by high electric fields. It has been determined that in order to destroy living tissue, the waveforms have to generate an electric field of at least 30,000 V/m in the tissue treatment region. In one embodiment, the IRE generator 14 may generate voltages from about 100-1000 VDC. The IRE generator 14 may generate voltage pulses from 0.01-100 ms. These pulses may be generated at a suitable pulse repetition rate. The electrical current depends on the voltage amplitude, pulse width, pulse repetition rate, and the volume of tissue being treated. In one embodiment, the IRE generator 14 generates 20 ms pulses of 500 VDC amplitude between the electrodes 28. The embodiments, however, are not limited in this context.

When using the IRE generator 14 in monopolar mode with two or more electrical therapy electrodes 28, a grounding pad is not needed on the patient. Because a generator will typically be constructed to operate upon sensing connection of ground pad to the patient when in monopolar mode, it can be useful to provide an impedance circuit to simulate the connection of a ground pad to the patient. Accordingly, when the electrical ablation system 10 is used in monopolar mode without a grounding pad, an impedance circuit can be assembled by one skilled in the art, and electrically connected in series with one of the electrical therapy electrodes 28 that would otherwise be used with a grounding pad attached to a patient during monopolar electrosurgery. Use of an impedance circuit allows use of the IRE generator 14 in monopolar mode without use of a grounding pad attached to the patient.

FIG. 2 is an enlarged view of one embodiment of the therapeutic/diagnostic probe 20 of one embodiment of the endoscopic ablation system 10 shown in FIG. 1. The therapeutic/diagnostic probe 20 extends through the distal end of the flexible shaft 32. In one embodiment, the therapeutic/diagnostic probe 20 protrudes from the distal end of an internal lumen extending between the proximal and distal ends of the flexible endoscope 12. In one embodiment, the therapeutic/diagnostic probe 20 may comprise a biopsy device adapted and configured to remove sample tissue using an incisional, core, needle aspiration, or optical biopsy techniques. In one embodiment, the biopsy device comprises one or more diagnostic probes 26. As previously discussed, the electrical therapy electrodes 28 may be joined or attached to the diagnostic probes 26 in any suitable manner.

As previously discussed, the electrical therapy electrodes 28 are connected to the diagnostic probes 26 in any known suitable manner and are located in a spaced-apart relationship so as to define a distance D between the electrodes. The distance D is adjustable and can be increased or decreased by rotating one or both of the diagnostic probes 26. The therapeutic/diagnostic probe 20 are rotatable about a central axis 39. Thus, the diagnostic probes 26 and the electrodes 28 are rotatable about the central axis 39. The electrodes 28 may be rotated to increase or decrease the relative distance D between the electrode 28 either to focus the energy in a smaller tissue region or to enlarge the tissue treatment region. In this manner, the operator can surround the diseased tissue such as a cancerous lesion, a polyp, or a tumor. The electrodes 28 are energized with the electrical waveform generator 14 to treat the diseased tissue. The diagnostic probes 26 have a sharp tooth 33 at the distal end and are moveable from the distal end to the proximal end of the flexible shaft 32 capable of slicing a thin section of the tissue to obtain a biopsy sample (shown in more detail below). The diagnostic probes 26 may comprise a bore 35 (FIGS. 3A, B) at the distal end extending from a proximal end to the distal end of the diagnostic probes 26. Suction may be applied at the proximal end of the probes to remove a tissue sample before and/or after treatment through the bore 35 (FIGS. 3A, B) formed through the diagnostic probes 26.

The electrical therapy electrodes 28 may be positioned in any orientation relative to the diagnostic probes 26. The electrodes 28 and the diagnostic probes 26 may have any suitable shape. In the illustrated embodiment, the electrodes 28 may have a generally cuboidal shape and the diagnostic probes 26 may have an elongate cylindrical shape with a sharp tooth 33 and a bore 35 formed therein at the distal end. The electrical conductors 18 are electrically insulated from each other and surrounding structure except for the electrical connections the electrodes 28. The distal end of the flexible shaft 32 of the flexible endoscope 12 may comprise a light source 40, a viewing port 38, and one or more working channels 36. The viewing port 38 transmits an image within its field of view to an optical device such as a charge coupled device (CCD) camera within the flexible endoscope 12 so that an operator may view the image on a display monitor (not shown). In the embodiment shown in FIG. 2, the distal end of flexible shaft 32 is proximal to the electrodes 28 and is within the viewing field of the flexible endoscope 12 to enable the operator to see the diseased tissue to be treated between the electrodes 28.

Figure 3A:
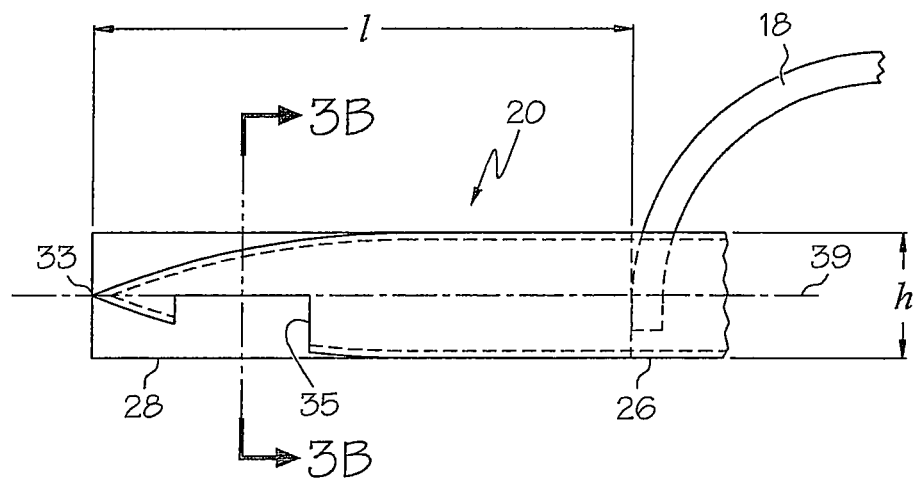
FIG. 3A is a side view of a distal end of one embodiment of a therapeutic/diagnostic probe comprising a biopsy probe and an electrical therapy electrode assembly.
Figure 3B:
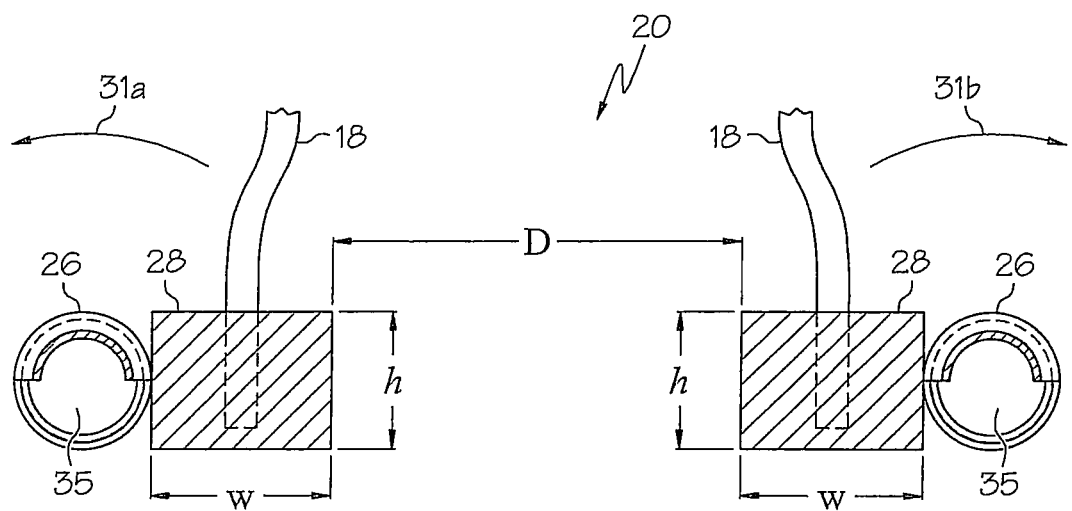
FIG. 3B is a sectional view of one embodiment of a therapeutic/diagnostic probe taken along section line 3B-3B showing the geometric relationship between the electrodes and the diagnostic probes.

FIG. 3A is a side view of the distal end of one embodiment of the therapeutic/diagnostic probe 20 comprising a biopsy probe 26 and an electrical therapy electrode 28 assembly. FIG. 3B is a sectional view of one embodiment of a therapeutic/diagnostic probe 20 taken along section line 3B-3B showing the geometric relationship between the electrodes 28 and the diagnostic probes 26. In the embodiment illustrated in FIGS. 3A, B, the cuboidal electrodes 28, each have a width "w," a length "l," and a thickness or height "h." The electrodes 28 have parallel, adjacent edges 8 separated by a distance "D." This geometry of the electrodes 28, the distance D between them, and the electrical waveform may be used to calculate an ablation index, which has particular significance to the location, size, shape, and depth of ablation achievable, as will be described later. The diagnostic probes 26 may be juxtaposed with the electrodes 28. In this embodiment, the two cylindrically elongate diagnostic probes 26 have a bore 35 for removing ablated tissue or taking biopsy samples of the tissue by way of suction. The length of the diagnostic probes 26 may extend through the entire length of the flexible endoscope 12. The conductors 18 are attached to the electrodes 28 in any suitable manner including welding, soldering, or brazing and may employ many different energy sources such as, for example, a gas flame, heat source, an electric arc, a laser, an electron beam, friction, and ultrasound. The electrodes 28 are attached to the diagnostic probes 26 and may be rotated about the central axis 39 in the directions indicated by arrows 31$a$ and 31$b$.

Figure 4:
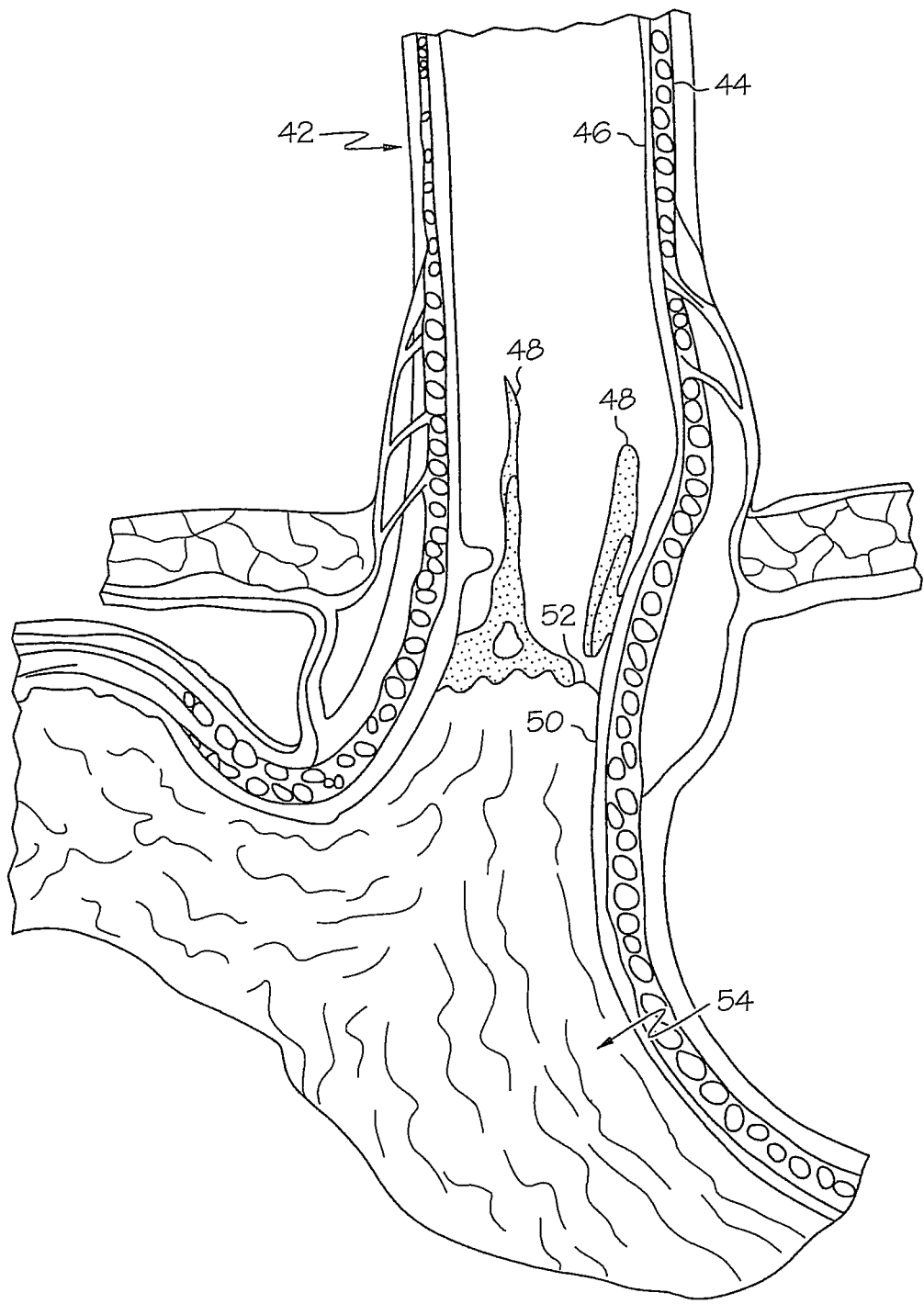
FIG. 4 is a sectional view of the lower end of an esophagus and the upper portion of a stomach of a human being.

FIG. 4 is a sectional view of the lower end of an esophagus 42 and the upper portion of a stomach 54 of a human being. The esophagus 42 has a mucosal layer 46, a muscular layer 44, and a region of diseased tissue 48. The boundary between the mucosal layer 46 of the esophagus 42 and a gastric mucosa 50 of the stomach 54 is a gastro-esophageal junction 52, which is approximately the location for the lower esophageal sphincter (LES). The LES allows food to enter the stomach 54 while preventing the contents of the stomach 54 from refluxing into the lower esophagus 42 and damaging the mucosal layer 46. The diseased tissue 48 can develop when chronic reflux is not treated. In one form, the diseased tissue 48 may be, for example, intestinal metaplasia, which is an early stage of Barrett's esophagus. As can be seen in FIG. 4, the esophagus 42 is relatively flaccid and contains numerous folds and irregularities on the interior lining.

Figure 5:
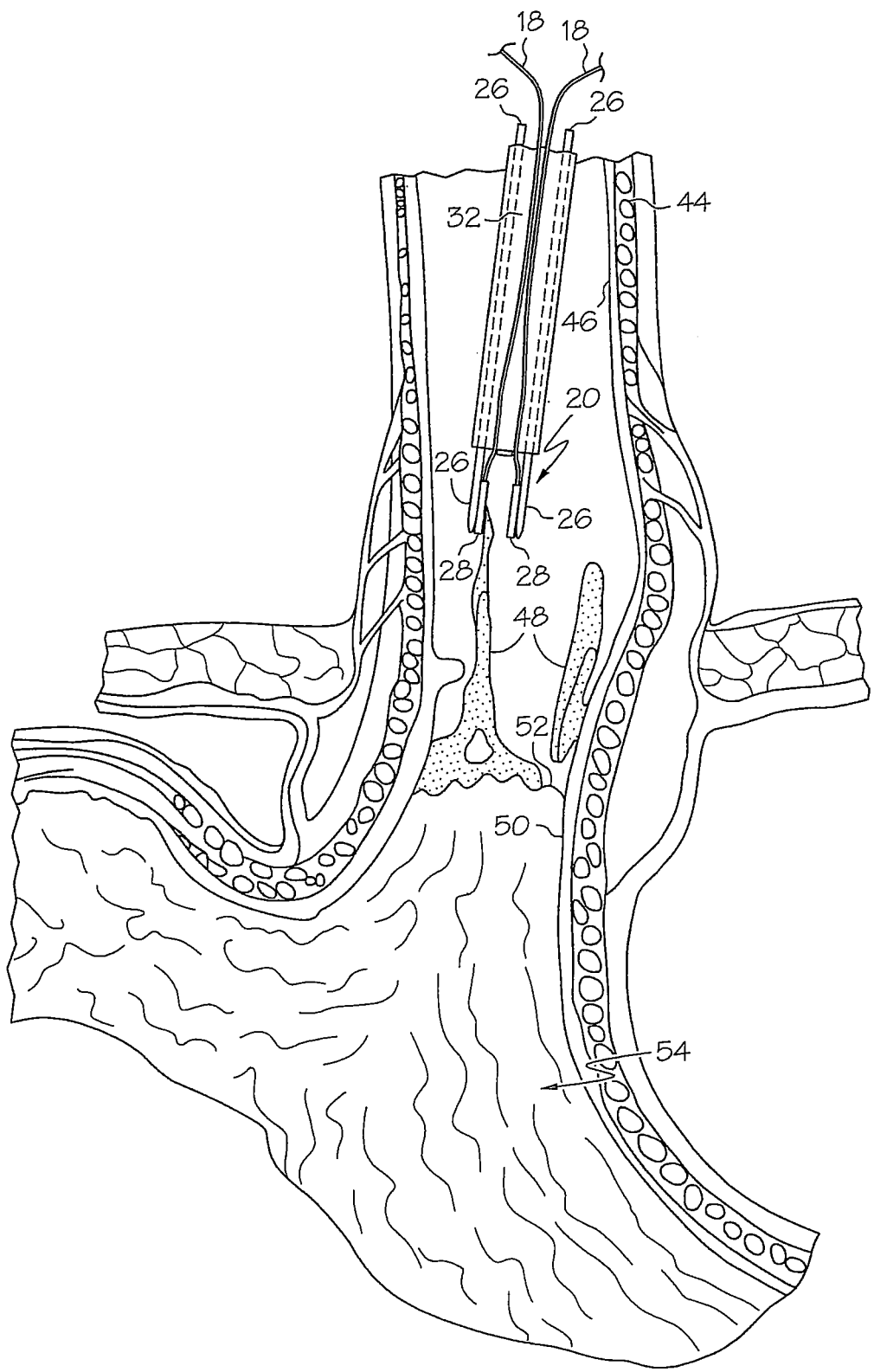
FIG. 5 illustrates the use of one embodiment of an endoscopic ablation system to treat diseased tissue in the lower esophagus.

FIG. 5 illustrates the use of one embodiment of the endoscopic ablation system 10 to treat the diseased tissue 48 in the lower esophagus 42. The operator positions the therapeutic/diagnostic probe 20 using endoscopic visualization so that the diseased tissue 48 to be treated is within the field of view of the flexible endoscope 12. Once the operator positions the therapeutic/diagnostic probe 20 such that the electrical therapy electrodes 28 are located above the diseased tissue 48, the operator may energize the electrodes 28 with the electrical waveform generator 14 to destroy the diseased tissue 48 in the tissue treatment region. For example, the electrodes 28 may be energized with an electrical waveform having amplitude of approximately 500 VDC and a pulse width of approximately 20 ms at a frequency of approximately 10 Hz. In this manner, the diseased tissue 48 in the tissue treatment region may be destroyed. This procedure may take very little time and may be repeated to destroy relatively larger portions of the diseased tissue 48. Suction may be applied to remove the treated tissue sample through the bore 35 formed in the diagnostic probes 26.

Figure 6:
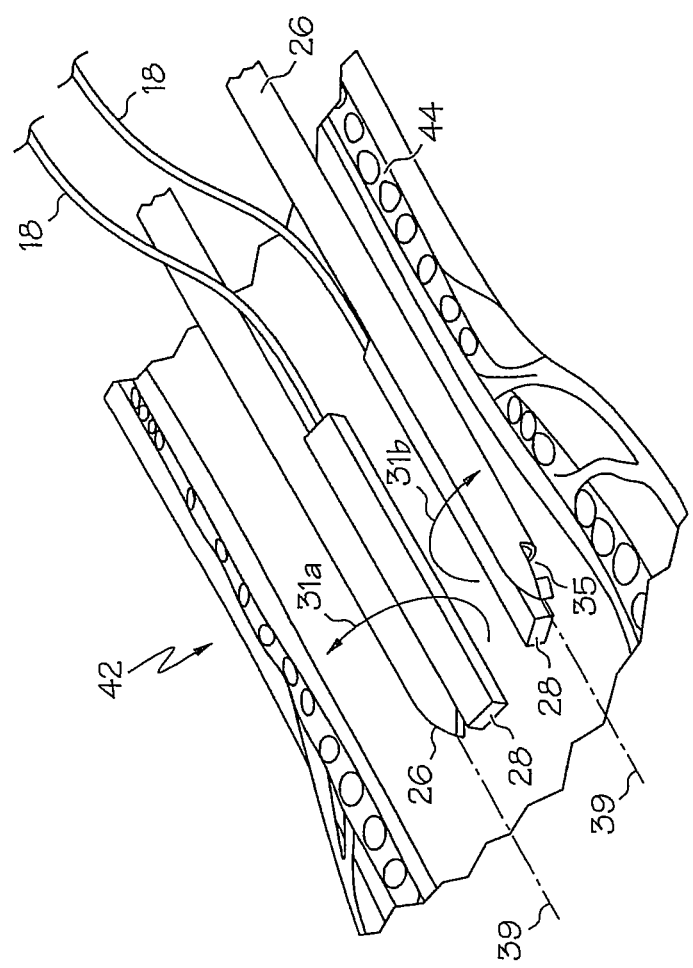
FIG. 6 illustrates the use of one embodiment of an endoscopic ablation system to treat diseased tissue in the lower esophagus.

FIG. 6 illustrates the use of the endoscopic ablation system 10 to treat the diseased tissue 48 in the lower esophagus 42. As shown in the illustrated embodiment, the electrical therapy electrodes 28 can be rotated about the central axis 39 in the direction indicated by arrows 31a and 31b. The treated tissue can be sucked into the bore 35 of the biopsy probe 26 by applying suction to thereto.

Figure 7:
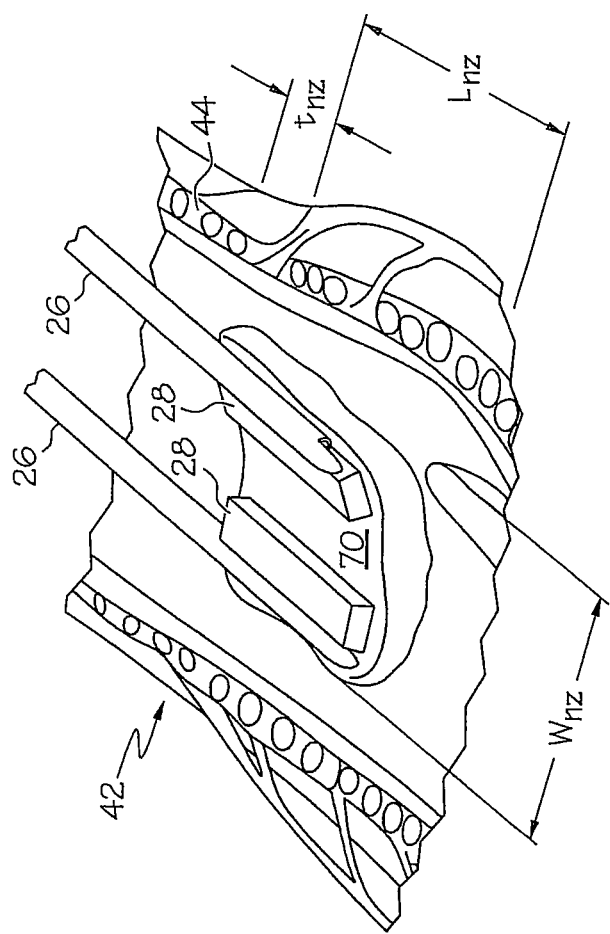
FIG. 7 illustrates one embodiment of a necrotic zone defined by the geometry and placement of the electrical therapy electrodes.

FIG. 7 illustrates one embodiment of a necrotic zone 70 defined by the geometry and placement of the electrical therapy electrodes 28. The energy delivered by the waveform to the electrodes 28 in terms of frequency, amplitude, and pulse width should be suitable to destroy the tissue in the necrotic zone 70. Based on the location and geometry of the electrodes 28, and the energy delivered thereto, the necrotic zone 70 in the illustrated embodiment may be approximated generally as a volume of width "wnz," a thickness "tnz," and a length "lnz." Energizing the electrodes 28 destroys the diseased tissue 48 within the necrotic zone 70. In one embodiment, electrodes 28 with a width "w=0.5 mm," a length "l=10 mm," and a thickness "h=0.5 mm" (as shown in FIGS. 3A, B) and a waveform of approximately 500 VDC, a pulse width of 20 ms, and a frequency of 10 Hz, would define a necrotic zone 70 with dimensions of approximately wnz=6 mm wide, lnz=10 mm long, and hnz=2 mm deep. If a biopsy indicates that the treatment region includes dysplastic or malignant cells, or if the treatment region is larger than the necrotic zone 70, the process may be repeated until all the diseased tissue 48 is destroyed in the treatment region and clean margins are recorded. In one embodiment, optical biopsy may be used as an alternative to the vacuum diagnostic probes 26 shown in the illustrated embodiments.

FIG. 8 is a sectional view taken along the longitudinal axis of one embodiment of an endoscopic ablation system 10 shown in FIG. 1. The distal portion of the flexible shaft 32 is located inside a rotation tube 22 of the endoscopic ablation system 10. The pair of electrical conductors 18 pass through a strain relief 66 of a rotation knob 58. In the illustrated embodiment an external tube 64 may be located over the flexible shaft 32 such that the conductors 18 pass between the external tube 64 and the rotation tube 22. Each of the conductors 18 connect electrically to the electrical therapy electrodes 28 in the therapeutic/diagnostic probe 20. The rotation tube 22 rotatably joins the rotation knob 58. The operator can rotatably orient the electrodes 28, even after insertion into the esophagus, by remotely rotating the diagnostic probes 26 about the central axis 39 of each of the therapeutic/diagnostic probe 20. The therapeutic/diagnostic probe 20 is within the field of view of the flexible endoscope 12, thus enabling the operator to see on a display monitor the tissue that is located between the electrodes 28. Optionally, in one embodiment, a valve element (not shown) may extend from the distal end of therapeutic/diagnostic probe 20 to prevent tissue or fluids from entering the therapeutic/diagnostic probe 20.

FIG. 9 is an end view taken along line 9-9 of one embodiment of the therapeutic/diagnostic probe 20 of the endoscopic ablation system 10 shown in FIG. 8. The electrical conductors 18 connect to the electrical therapy electrodes 28. The rotation tube 22 retains the flexible shaft 32. The inside diameter of the rotation tube 22 is larger than the outer diameter of the flexible endoscope 12 to allow rotation of the rotation tube 22 while holding the flexible endoscope 12 stationary, or vice versa. Each of the therapeutic/diagnostic probe 20 comprising the diagnostic probes 26 attached to the electrodes 28 extend outwardly from the distal end of the flexible shaft 32 through each of the working channels 36. In this embodiment, the operator may endoscopically view the tissue between the electrodes 28. The flexible endoscope 12 includes the light source 40, the viewing port 38, and the one or more working channels 36.

FIG. 10 is a sectional view taken along line 10-10 of the rotation tube 22 of the endoscopic ablation system 10 shown in FIG. 8. The external tube 64 and the rotation tube 22 assemble and retain the electrical conductors 18 as already described. The light source 40, the viewing port 38, and the one or more working channels 36 of the flexible endoscope 12 are shown.

Figure 11:
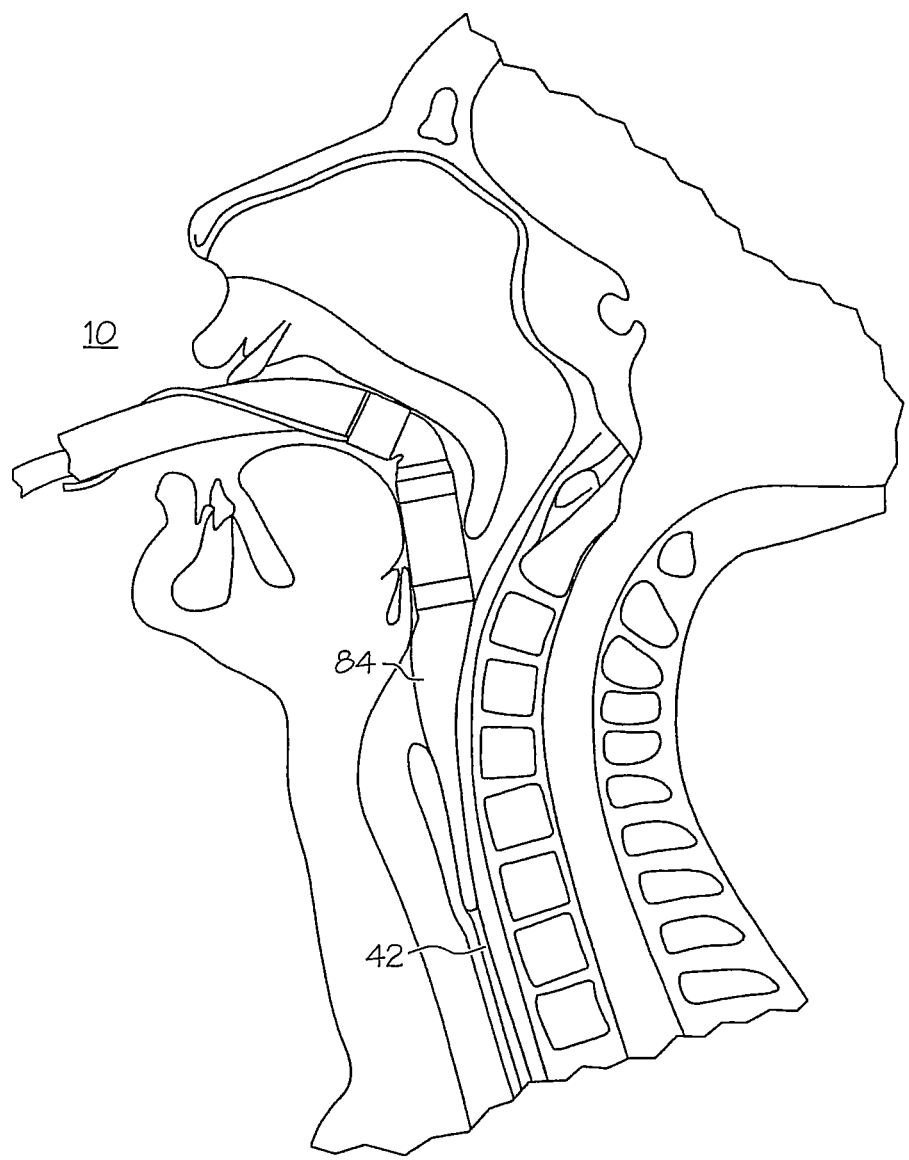
FIG. 11 shows one embodiment of a distal portion of an endoscopic ablation system shown in FIG. 1 partially inserted into the esophagus of a patient.

FIG. 11 shows one embodiment of the distal portion of the endoscopic ablation system 10 shown in FIG. 1 partially inserted into the esophagus 42 of a patient. A tapered end cover 84 dilates the esophagus 42 as the operator gently inserts the therapeutic/diagnostic probe 20 for positioning near the diseased tissue 48 to be ablated. A flexible coupling 88 flexes as shown, reducing the required insertion force and minimizing trauma (and post-procedural pain).

The operator may treat the diseased tissue 48 using the embodiment of the endoscopic ablation system 10 comprising the therapeutic/diagnostic probe 20 shown in FIGS. 1-3 and 5-11 as follows. The operator inserts the flexible shaft 32 of the endoscope 12 into the lower esophagus 42 trans-orally. A rigid support member at the distal end of the endoscope 12 holds the lower esophagus 42 open as the operator uses endoscopic visualization through the therapeutic/diagnostic probe 20 to position the electrical therapy electrodes 28 next to the diseased tissue 48 to be treated. The rigid support member opens and supports a portion of the flaccid, lower esophagus 42 and helps to bring the diseased tissue 48 to be treated into intimate contact with the electrodes 28 and within the field of view of the flexible endoscope 12. While watching through the viewing port 38, the operator actuates the switch 62, electrically connecting the electrodes 28 to the electrical waveform generator 14 through the electrical conductors 18. Electric current then passes through the portion of the diseased tissue 48 positioned between the electrodes 28 and within the field of view. When the operator observes that the tissue in the field of view has been ablated sufficiently, the operator deactuates the switch 62 to stop the ablation. The operator may reposition the electrodes 28 for subsequent tissue treatment, or may withdraw the therapeutic/diagnostic probe 20 (together with the flexible endoscope 12).

Figure 12:
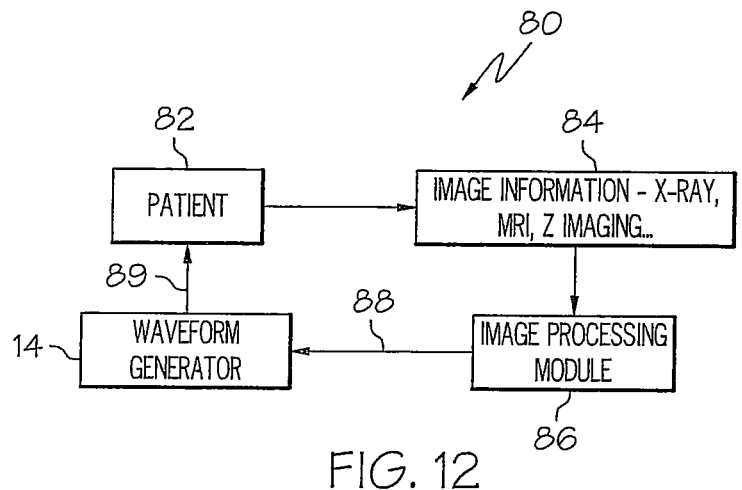
FIG. 12 is a diagram of one embodiment of a control loop for one embodiment of an irreversible electroporation therapy procedure to treat diseased tissue as described herein.

FIG. 12 is a diagram of one embodiment of a control loop 80 for one embodiment of an IRE therapy procedure to treat diseased tissue as described herein. As previously discussed, the IRE therapy may be effective in quickly creating necrosis of live tissue and destroying diseased (e.g., cancerous) tissue in-vivo. Real time information feedback about the size in volume of a necrotic zone may be helpful during an IRE therapy procedure for focal treatment of diseased tissue 48.

Prior to an IRE therapy procedure, a patient 82 will have an image of the diseased tissue 48 taken for clinical purposes in an effort to reveal, diagnose, or examine the diseased tissue 48 and to identify its location more precisely. The image information 84 will generally include geometric information about the volume of the diseased tissue 48. The image information 84 is provided to an image processing module 86 to calculate the volume of the diseased tissue 48 and to display a virtual model of the diseased tissue 48 on a monitor. The image processing module 86 may comprise, for example, image processing software applications such as Comsol Multiphysics available by Comsol, Inc. to receive the image information 84, extract the geometric information, and determine (e.g., calculate) the voltage required to treat the proper volume and outline of the necrotic zone required to treat the diseased tissue 48. The image processing module 86 creates a virtual model of a treatment zone necessary to treat the diseased tissue 48. The image processing module 86 then determines waveform parameters 88 of a suitable electrical waveform necessary to destroy the diseased tissue 48. The waveform parameters 88 include the frequency, amplitude, and pulse width of the electrical waveform to be generated by the waveform generator 14. The waveform generator 14 would then generate the suitable electrical waveform to destroy the diseased tissue 48 based on the calculated waveform parameters 88.

The image processing module 86 also comprises image processing software applications such as Matlab available by MathWorks, Inc. to receive the image information 84 and the virtual model and display an image of the diseased tissue 48 overlaid with an image of the virtual model. The overlaid images enable the operator to determine whether the calculated electrical waveform parameters 88 are suitable for destroying the diseased tissue 48, whether too strong or too weak. Thus, the IRE waveform parameters 88 may be adjusted such that the virtual model image substantially overlays the entire diseased tissue image. The calculated parameters 88 are provided to the waveform generator 14 and the diseased tissue may be treated with an electrical waveform 89 based on the calculated parameters 88 as discussed herein. After the diseased tissue 48 is treated with the electrical waveform 89, a new image of the diseased tissue 48 can be generated to determine the extent or effectiveness of the treatment. The cycle may be repeated as necessary to ablate the diseased tissue 48 as much as possible.

Figure 13:
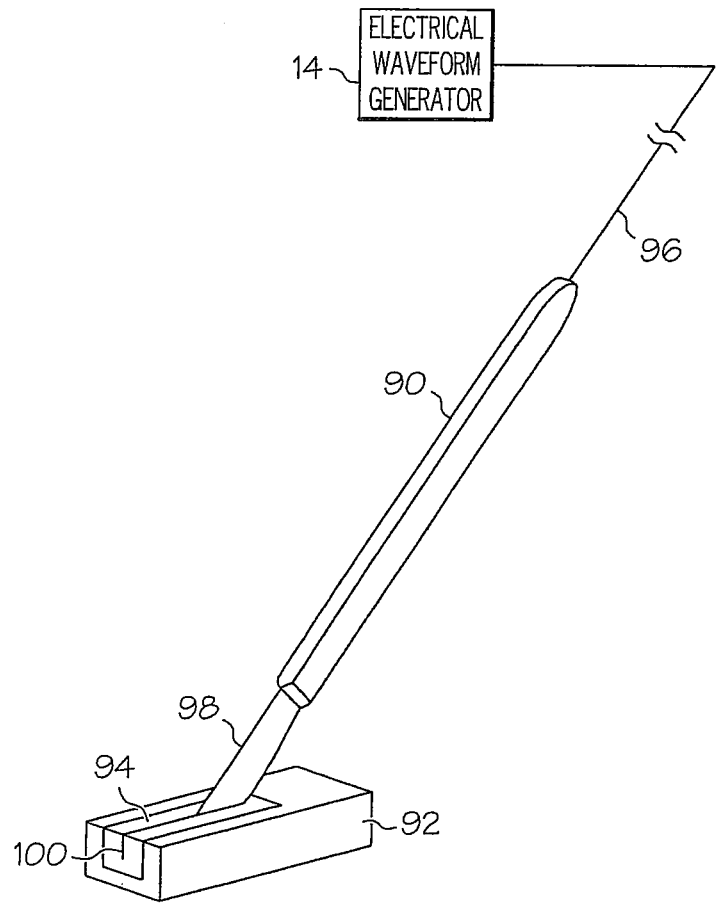
FIG. 13 illustrates one embodiment of an electrical scalpel for dissecting tissue.

FIG. 13 illustrates one embodiment of an electrical scalpel 90 for dissecting tissue 92. In one embodiment, the electrical scalpel 90 may be driven by an IRE waveform previously described. The scalpel 90 comprises a blade 98 that is formed of metal such as hardened and tempered steel (and/or stainless in many applications). The blade 98 is connected to the electrical waveform generator 14 by multiple electrical conductors 96. The electrical waveform generator 14 may generate an IRE waveform (e.g., 10 Hz frequency, 500 VDC amplitude, and 20 ms pulse). As the blade 98 dissects the tissue 92 along an incision 100, the electrical waveform generator 14 may be activated or pulsed to create a tissue destruction zone 94 surrounding the blade 98. Accordingly, as the blade 98 dissects the diseased tissue 92 it generates the tissue destruction zone 94 beyond the incision 100. This may help to ensure the destruction of any diseased tissue cells left behind. The pulse repetition rate or frequency of the electrical waveform generated by the generator 14 may be selected to provide a continuous zone of tissue destruction 94 as the blade 98 moves through the diseased tissue 92. In one embodiment, a feedback signal (e.g., audio, visual, or cut-off of electrical power to the blade 98) may be provided to the operator to indicate that the scalpel 90 is moving too quickly.

Figure 14:
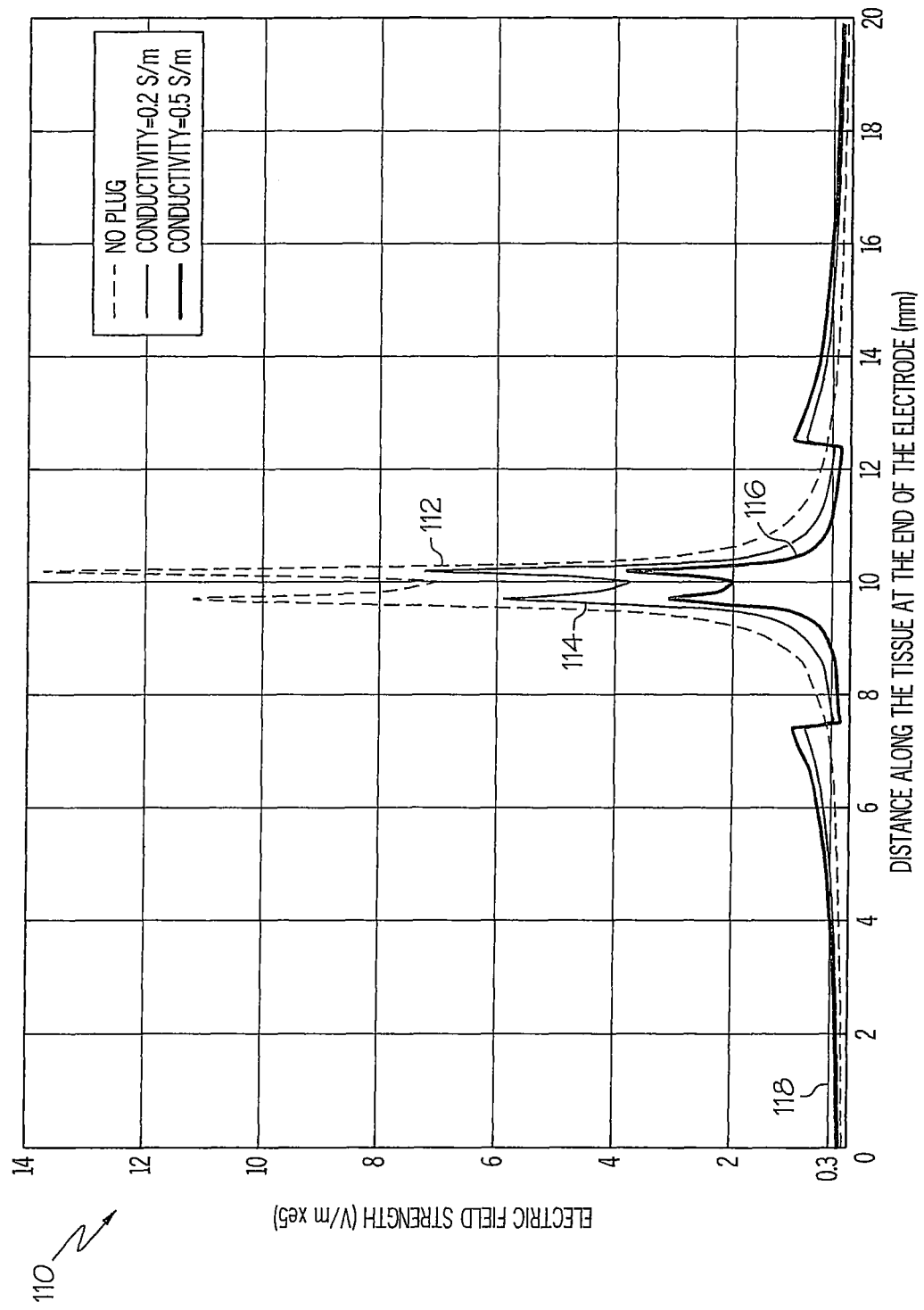
FIG. 14 is a graphical representation (graph) of electric field strength (along the y-axis) as a function of distance from an electrical therapy electrode under various conductivity environments near diseased tissue.

FIG. 14 is a graphical representation 110 (graph) of electric field strength (along the y-axis) as a function of distance from an electrical therapy electrode 28 under various conductivity environments near the diseased tissue 48. FIG. 15 is a close up of the graph 110 shown in FIG. 14A. In electrical therapy of diseased tissue 48, the volume of tissue that can be destroyed by an electrical waveform (e.g., the necrotic zone) may be defined by a minimum electric field strength applied to the tissue treatment region. The electric field strength in the tissue treatment region varies throughout the tissue as a function of the applied electrical waveform parameters frequency, amplitude, and pulse width as well as the conductivity of the tissue in the treatment region. When a single electrical therapy electrode 28 is located in a first position in the tissue treatment region of interest and a return pad is placed at a distance relatively far from the first position, an electric field is generated around the electrode 28 when it is energized with a particular electrical waveform. The magnitude of the electric field, however, diminishes rapidly in the radial direction away from the electrode 28. When two electrodes 28 are placed relatively close together, a larger pattern of tissue can be destroyed. Injecting a fluid having a higher conductivity than the tissue into the tissue treatment region extends the electric field of sufficient strength to destroy the tissue radially outwardly from the electrode 28. Thus, the addition of a fluid having higher conductivity than the tissue to be treated creates a larger tissue destruction zone by extending the electric field radially outwardly from the electrodes 28.

The graph 110 illustrates the electric field strength, along the y-axis, as a function of the radial distance from the electrical therapy electrode 28. The y-axis is labeled in units of volts/meter (V/m×$e^5$) and the x-axis is labeled in units of mm. The graph 110 illustrates a family of three functions with conductivity as a parameter. A first function 112 illustrates the electric field strength as a function of the radial distance from one of the electrodes 28 with no conductivity plug introduced into the tissue treatment region. A second function 114 illustrates the electric field strength as a function of the radial distance from one of the electrodes 28 with a conductivity plug of 0.2 S/m introduced in the tissue treatment region. A third function 116 illustrates the electric field strength as a function of the radial distance from one of the electrodes 28 with a conductivity plug of 0.5 S/m introduced in the tissue treatment region. As shown in the graph 110, the peak electric field strength of each of the functions 112, 114, 116 decreases with increased conductivity in the tissue treatment region in proximity to the electrode 28. However, the threshold 118 of each of the functions 112, 114, 116 where the electric field strength drops below the minimum threshold 118 of electric field strength required to destroy tissue becomes wider as the conductivity increases. In other words, increasing the conductivity of the tissue in the tissue treatment region extends the range of an effective electric field to destroy tissue or creates a larger necrotic zone. In one embodiment, the minimum electric field strength threshold 118 is approximately 30,000 V/m.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the various embodiments of the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that the device is sterilized. This can be done by any number of ways known to those skilled in the art including beta or gamma radiation, ethylene oxide, steam.

Although the various embodiments of the invention have been described herein in connection with certain disclosed embodiments, many modifications and variations to those embodiments may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An apparatus, comprising:
an elongate shaft;
a first channel and a second channel defined in the elongate shaft;
a first probe positioned at least partially within the first channel, wherein the first probe comprises a first distal-most portion and defines a first longitudinal axis extending to the first distal-most portion, wherein the first distal-most portion is laterally aligned with the first longitudinal axis, and wherein the first probe is rotatable within the first channel;
a first electrode coupled to the first distal-most portion of the first probe and laterally offset from the first longitudinal axis, wherein the first electrode is structured to rotate about the first longitudinal axis via the first probe, and wherein the first electrode is configured to couple to a bipolar electrical waveform generator;
a first conductor external to the first channel, wherein the first conductor is electrically coupled to the first electrode, and wherein the first conductor extends from a positive pole of the bipolar electrical waveform generator to the first electrode;
a second probe positioned at least partially within the second channel, wherein the second probe comprises a second distal-most portion and defines a second longitudinal axis extending to the second distal-most portion, and wherein the second distal-most portion is laterally aligned with the second longitudinal axis;
a second electrode coupled to the second distal-most portion of the second probe and laterally offset from the second longitudinal axis, wherein the second electrode is configured to couple to the bipolar electrical waveform generator;
a second conductor external to the second channel, wherein the second conductor is electrically coupled to the second electrode, and wherein the second conductor extends from a negative pole of the bipolar electrical waveform generator to the second electrode; and
an adjustable ablation region defined between the first and second electrodes, wherein the ablation region is adjustable by rotating the first probe.

2. The apparatus of claim 1, further comprising a strain reliever, wherein the first and second conductors extend through the strain reliever.

3. The apparatus of claim 1, wherein the first and second electrodes are configured to receive an irreversible electroporation electrical waveform, and wherein the irreversible electroporation electrical waveform generates an electrical field of at least 30,000 V/cm in the adjustable ablation region.

4. The apparatus of claim 1, wherein the second probe is rotatable within the second channel and wherein the ablation region is adjustable by rotating the first and second electrodes.

5. The apparatus of claim 1, further comprising an endoscope, wherein the endoscope comprises the first channel and the second channel.

6. The apparatus of claim 5, further comprising:
an illuminator positioned to illuminate tissue; and
an image sensor positioned to image tissue therethrough.

7. The apparatus of claim 1, wherein the first and second electrodes are configured to access a tissue treatment region in a lung.

8. An apparatus, comprising:
an elongate shaft;
a first channel and a second channel defined in the elongate shaft;
a first probe positioned at least partially within the first channel, wherein the first probe comprises a first distal-most portion and defines a first longitudinal axis, wherein the first distal-most portion is aligned with the first channel, and wherein the first probe is rotatable within the first channel;
a first electrode extending from the first distal-most portion of the first probe and laterally offset from the first longitudinal axis, wherein the first electrode is structured to rotate about the first longitudinal axis via the first probe, and wherein the first electrode is configured to couple to a bipolar electrical waveform generator;
a first conductor in electrical communication with the first electrode, wherein the first conductor is positioned outside the elongate shaft, and wherein the first conductor extends from one of a positive pole or a negative pole of the bipolar electrical waveform generator to the first electrode;
a second probe positioned at least partially within the second channel, wherein the second probe comprises a second distal-most portion and defines a second longitudinal axis, and wherein the second distal-most portion is aligned with the second channel;
a second electrode extending from the second distal-most portion of the second probe and laterally offset from the second longitudinal axis, wherein the second electrode is configured to couple to the bipolar electrical waveform generator;
a second conductor in electrical communication with the second electrode, wherein the second conductor is positioned outside the elongate shaft, and wherein the second conductor extends from the other of the positive pole or the negative pole of the bipolar electrical waveform generator to the second electrode;

wherein the first and second electrodes are configured to receive an irreversible electroporation electrical waveform through the respective first and second conductors; and an adjustable ablation region defined between the first and second electrodes, wherein the ablation region is adjustable by rotating the first probe.

9. The apparatus of claim 8, further comprising a strain reliever, wherein the first and second conductors extend through the strain reliever.

10. The apparatus of claim 8, wherein the irreversible electroporation electrical waveform generates an electric field of at least 30,000 V/m in the adjustable ablation region.

11. The apparatus of claim 8, comprising:
an illuminator positioned to illuminate tissue; and
an image sensor positioned to image tissue therethrough.

12. The apparatus of claim 8, wherein the second probe is rotatable within the second channel and wherein the ablation region is adjustable by rotating the first and second electrodes.

13. A method, comprising:
positioning an elongate member comprising first and second channels within a body cavity, wherein a first and a second probe are disposed within the respective first and second channels, wherein the first and second probes each define a central axis, wherein the first and second probes each comprise a distal-most end aligned with the respective central axis, wherein a first and a second electrode are coupled to the distal-most ends of the respective first and second probes, wherein the first and second electrodes are laterally offset from the central axes of the respective first and second probes, and wherein a first and a second conductor disposed external to the respective first and second channels are electrically coupled to the respective first and second electrodes; and rotating at least one of the first and second probes within the respective first and second channels about the central axis of the respective at least one first and second probes to adjust an ablation region positioned between the first and second electrodes; and applying an irreversible electroporation (IRE) electrical waveform sufficient to ablate tissue positioned within the ablation region with a bipolar electrical waveform generator electrically coupled to the first and second electrodes through the respective first and second conductors that extend from a respective positive and negative pole of the bipolar electrical waveform generator to the respective first and second electrodes.

14. The method of claim 13, wherein the IRE electrical waveform is suitable to destroy diseased tissue in the ablation region, and wherein the IRE electrical waveform parameters comprise amplitude, frequency, and pulse width.

15. The method of claim 13, further comprising generating an electric field of at least 30,000 V/m in the ablation region.

16. The method of claim 13, further comprising injecting a fluid into the ablation region, wherein the fluid has a higher conductivity than diseased tissue in the ablation region.

17. The method of claim 13, further comprising:
illuminating the ablation region with at least one illuminator positioned to illuminate tissue; and
imaging the ablation region with an image sensor positioned to image tissue therethrough.

18. The method of claim 17, further comprising modifying the IRE electrical waveform based on the imaged tissue in the ablation region.

19. The method of claim 13, further comprising positioning the elongate member in a tissue treatment region located in a lung.

* * * * *